(12) United States Patent
Hunter

(10) Patent No.: US 6,707,545 B1
(45) Date of Patent: Mar. 16, 2004

(54) OPTICAL SIGNAL ROUTING METHOD AND APPARATUS PROVIDING MULTIPLE INSPECTION COLLECTION POINTS ON SEMICONDUCTOR MANUFACTURING SYSTEMS

(75) Inventor: Reginald Hunter, Round Rock, TX (US)

(73) Assignee: Applied Materials, Inc., Santa Clara, CA (US)

( * ) Notice: Subject to any disclaimer, the term of this patent is extended or adjusted under 35 U.S.C. 154(b) by 345 days.

(21) Appl. No.: 09/684,733

(22) Filed: Oct. 6, 2000

Related U.S. Application Data

(63) Continuation-in-part of application No. 09/391,341, filed on Sep. 7, 1999.

(51) Int. Cl.⁷ ............................................. G01N 21/88
(52) U.S. Cl. ............................... 356/237.5; 250/559.45
(58) Field of Search .................... 356/237.5, 237.2, 356/630; 250/559.27, 559.45

(56) References Cited

U.S. PATENT DOCUMENTS

| | | |
|---|---|---|
| 4,441,124 A | 4/1984 | Heebner et al. |
| 4,449,818 A | 5/1984 | Yamaguchi et al. |
| 4,499,595 A | 2/1985 | Masaitis et al. ................ 382/9 |
| 4,626,101 A | 12/1986 | Ogawa et al. ............... 356/237 |
| 4,732,473 A * | 3/1988 | Bille et al. ................ 356/237.5 |
| 4,772,126 A | 9/1988 | Allemand et al. |
| 4,893,932 A | 1/1990 | Knollenberg |
| 4,898,471 A | 2/1990 | Stonestrom et al. ........ 356/394 |
| 4,920,385 A | 4/1990 | Clarke et al. ................ 356/237 |
| 4,941,980 A | 7/1990 | Halavee et al. |
| 4,969,748 A | 11/1990 | Crowley et al. |
| 4,977,330 A * | 12/1990 | Batchelder et al. .... 250/559.27 |
| 4,989,973 A | 2/1991 | Noso et al. .................. 356/239 |
| 5,058,178 A | 10/1991 | Ray ............................... 382/8 |
| 5,120,034 A | 6/1992 | Van Engelen et al. |

(List continued on next page.)

FOREIGN PATENT DOCUMENTS

| | | | |
|---|---|---|---|
| EP | 0 206 709 A2 | 12/1986 | ............ G06K/9/00 |
| EP | 0 398 781 A3 | 11/1990 | .......... G01N/21/88 |
| EP | 0 638 801 A | 2/1995 | .......... G01N/21/88 |
| EP | 0 821 085 A1 | 1/1998 | .......... C30B/31/10 |
| EP | 1 030 173 A1 | 8/2000 | .......... G01N/21/89 |
| EP | 1030173 A1 | 8/2000 | .......... G01N/21/89 |
| EP | 1 083 424 A2 | 3/2001 | .......... G01N/21/94 |
| JP | 09196859 | 7/1997 | .......... G01N/21/88 |
| WO | 99/00661 | 1/1999 | .......... G01N/21/64 |
| WO | 99/49500 | 9/1999 | ........... H01L/21/00 |
| WO | WO 99/56113 | 11/1999 | .......... G01N/21/89 |

OTHER PUBLICATIONS

Written Opinion for PCT/US01/31293, dated Dec. 31, 2002.
PCT International Preliminary Examination Report, May 30, 2003.

(List continued on next page.)

*Primary Examiner*—Zandra V. Smith
(74) *Attorney, Agent, or Firm*—Moser Patterson & Sheridan

(57) ABSTRACT

The present invention generally provides an apparatus and a method for inspecting a substrate in a processing system. More specifically, optical signal routing methods and apparatus provide multiple inspection collection points on a semiconductor processing system. In one aspect, an optical inspection system comprises a light source and an optical receiving device, such as a CCD camera, to illuminate and inspect a substrate for various optical signatures. A plurality of optical inspection systems are connected to a signal switching device, such as a multiplexer, which operates to route a particular signal to a detector.

32 Claims, 41 Drawing Sheets

U.S. PATENT DOCUMENTS

| | | | |
|---|---|---|---|
| 5,164,603 A | * | 11/1992 | Hartman et al. ........ 250/559.46 |
| 5,177,559 A | | 1/1993 | Batchelder et al. |
| 5,186,718 A | | 2/1993 | Tepman et al. ............. 29/25.01 |
| 5,233,191 A | | 8/1993 | Noguchi et al. ............ 250/306 |
| 5,274,434 A | | 12/1993 | Morioka et al. ............ 356/237 |
| 5,317,656 A | * | 5/1994 | Moslehi et al. ............... 385/12 |
| 5,416,594 A | | 5/1995 | Gross et al. ................ 356/237 |
| 5,463,459 A | | 10/1995 | Morioka et al. ............ 356/237 |
| 5,465,152 A | | 11/1995 | Bilodeau et al. ............ 356/371 |
| 5,479,252 A | | 12/1995 | Worster et al. ............. 356/237 |
| 5,483,138 A | | 1/1996 | Shmookler et al. |
| 5,486,919 A | | 1/1996 | Tsuji et al. .................. 356/349 |
| 5,563,798 A | | 10/1996 | Berken et al. |
| 5,637,881 A | | 6/1997 | Burghard et al. ........... 250/573 |
| 5,644,393 A | | 7/1997 | Nakamura et al. .......... 356/237 |
| 5,646,725 A | | 7/1997 | Hagiwara ................... 356/237 |
| 5,659,172 A | | 8/1997 | Wagner et al. |
| 5,663,569 A | | 9/1997 | Hayano ................. 250/559.45 |
| 5,694,214 A | | 12/1997 | Watanabe et al. ........... 356/237 |
| 5,699,447 A | | 12/1997 | Alumot et al. .............. 382/145 |
| 5,737,072 A | | 4/1998 | Emery et al. ................. 356/73 |
| 5,748,305 A | | 5/1998 | Shimono et al. |
| 5,774,222 A | | 6/1998 | Maeda et al. ............... 356/394 |
| 5,781,230 A | | 7/1998 | Nguyen et al. ............. 348/128 |
| 5,797,317 A | | 8/1998 | Lahat et al. |
| 5,801,824 A | | 9/1998 | Henley ....................... 356/237 |
| 5,805,278 A | | 9/1998 | Danko ........................ 356/237 |
| 5,808,735 A | | 9/1998 | Lee et al. .................... 356/237 |
| 5,818,576 A | | 10/1998 | Morishige et al. .......... 356/237 |
| 5,822,213 A | | 10/1998 | Huynh |
| 5,834,758 A | | 11/1998 | Trulson et al. ........... 250/201.2 |
| 5,861,952 A | | 1/1999 | Tsuji et al. .................. 356/349 |
| 5,864,394 A | | 1/1999 | Jordan, III et al. ......... 356/237 |
| 5,883,710 A | | 3/1999 | Nikoonahad et al. .... 356/237.2 |
| 5,889,593 A | | 3/1999 | Bareket ...................... 356/445 |
| 5,900,633 A | * | 5/1999 | Solomon et al. ........ 250/339.08 |
| 5,903,342 A | | 5/1999 | Yatsugake et al. ....... 356/237.4 |
| 5,909,276 A | | 6/1999 | Kinney et al. .............. 356/237 |
| 5,940,175 A | | 8/1999 | Sun ......................... 356/237.3 |
| 6,012,966 A | | 1/2000 | Ban et al. ...................... 451/8 |
| 6,020,957 A | | 2/2000 | Rosengaus et al. ...... 356/237.4 |
| 6,236,903 B1 | | 5/2001 | Kim et al. ................... 700/121 |
| 6,342,704 B1 | * | 1/2002 | Jen et al. .................. 250/559.4 |
| 6,373,565 B1 | * | 4/2002 | Kafka et al. ............. 356/237.4 |

OTHER PUBLICATIONS

International Search Report for PCT/US01/42483, dated Oct. 14, 2002.

International Search Report for PCT/US01/31426, dated Nov. 27, 2002.

International Search Report for PCT/US01/31094, dated Nov. 27, 2002.

U.S. patent application Ser. No. 09/173,669, *Detection of Wafer Fragments in a Wafer Processing Apparatus*, filed on Oct. 15, 1998.

Search Report from EPO Appl. No. 00307704.7, dated Mar. 1, 2001.

European Search Report Dated Dec. 12, 2000.

Written Opinion (Form PCT/IPEA/408), dated Jan. 10, 2003 for PCT/US01/42470.

Written Opinion, International Application No. PCT/US01/31094. Jul. 11, 2003.

* cited by examiner

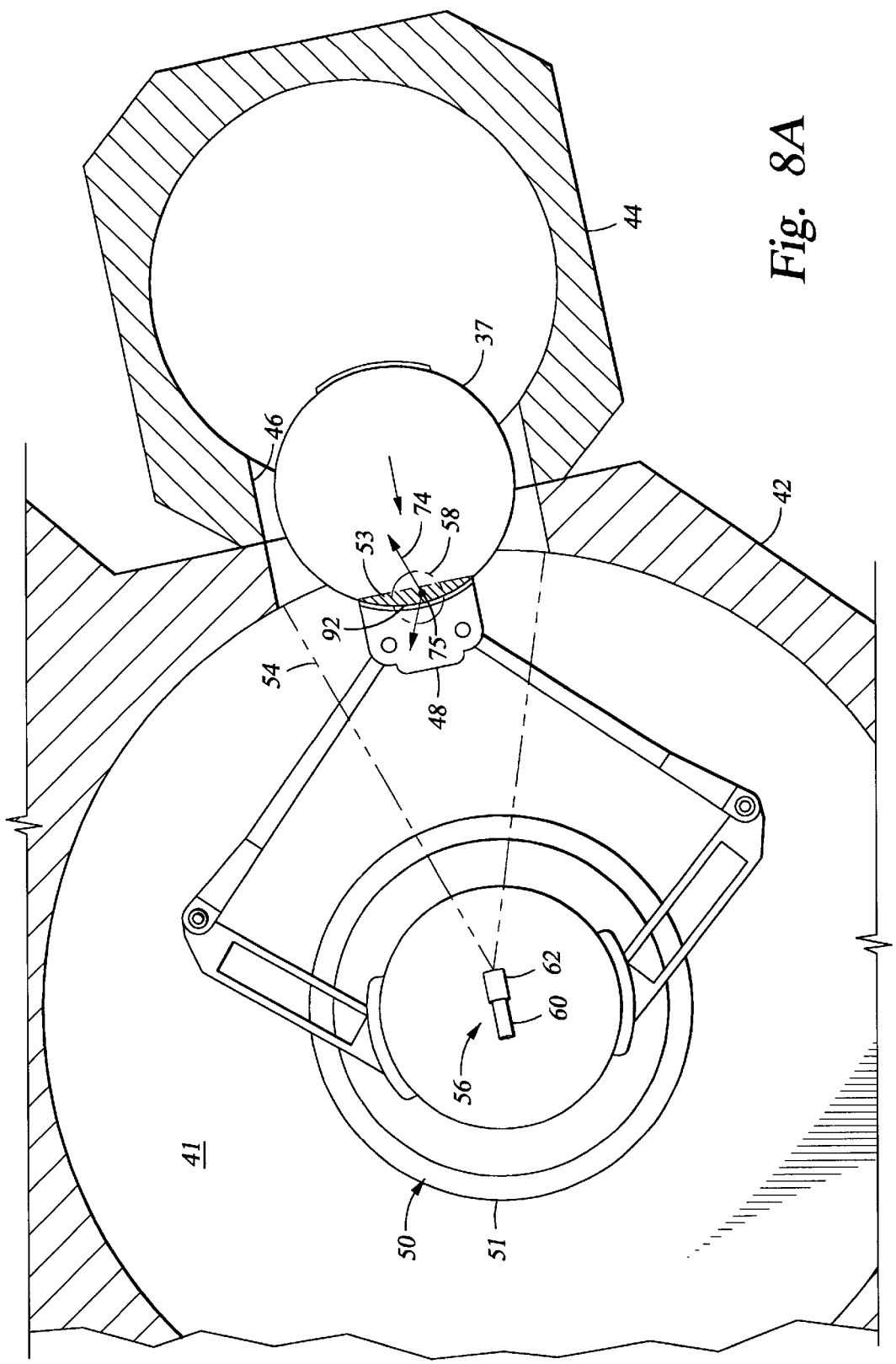

OPTICAL SIGNAL ROUTING METHOD AND APPARATUS PROVIDING MULTIPLE INSPECTION COLLECTION POINTS ON SEMICONDUCTOR MANUFACTURING SYSTEMS

This application is a continuation-in-part of U.S. application Ser. No. 09/391,341 filed on Sep. 7, 1999, entitled "Particle Detection and Embedded Vision System to Enhance Substrate Yield and Throughput."

BACKGROUND OF THE INVENTION

1. Field of the Invention

The invention relates to inspection methods and apparatus. More particularly, the invention relates to a method and apparatus for inspection of substrates to identify process and handling related defects and conditions.

2. Background of the Related Art

A chip manufacturing facility is composed of a broad spectrum of technologies. Cassettes containing semiconductor substrates are routed to various stations in the facility where they are either processed or inspected.

Semiconductor processing generally involves the deposition of material onto and removal ("etching") of material from substrates. Typical processes include chemical vapor deposition (CVD), physical vapor deposition (PVD), electroplating, chemical mechanical planorization (CMP) etching and others. During the processing and handling of substrates, the substrates undergo various structural and chemical changes. Illustrative changes include the thickness of layers disposed on the substrate, the material of layers formed on the substrate, surface morphology, changes in the device patterns, etc. These changes must be controlled in order to produce the desired electrical characteristics of the devices formed on the substrate. In the case of etching, for example, end-point detection methods are used to determine when the requisite amount of material has been removed from the substrate. More generally, successful processing requires ensuring the correct process recipe, controlling process excursions (e.g., gas flow, temperature, pressure, electromagnetic energy, duration, etc) and the like.

In addition, the processing environment must be sufficiently stable and free from contamination. Sources of contamination include wear from mechanical motion, degradation of seals, contaminated gases, other contaminated substrates, flaking of deposits from processing chambers, nucleation of reactive gases, condensation during chamber pumpdown, arcing in plasma chambers and so forth. Such sources of contamination produce particles that contact the substrates and can result in defective devices. As the geometries of device features shrink, the impact of contamination increases. Thus, current semiconductor manufacturing routinely includes inspection of substrates for particles to identify "dirty" processes or equipment.

Additionally, substrate centerfinding and orientation necessary steps during processing to generate positional information regarding substrates. In conventional systems such procedures are performed at designated locations in the processing system. Thus, a substrate must be shuttled to the designated locations in order to undergo each procedure, thereby decreasing system throughput.

Another situation which can cause increased processing costs is improper substrate routing in the chip manufacturing facility. Occasionally, a substrate may be improperly routed to a process chamber where the processing conditions cause a volatile reaction, thereby damaging the substrate and/or the processing chamber. For example, consider the case of a substrate with a photoresist layer that has been inadvertently routed to a PVD chamber. Processing this substrate in the PVD chamber is known to cause severe damage to the chamber, resulting in substantial repair and/or replacement costs. Because current processing systems are not equipped to prevent misrouting, the cost of ownership is increased.

Currently, comprehensive testing and analysis of substrates for process integrity and contamination requires the periodic or often constant removal of one or more substrates from the processing environment into a testing environment. Thus, production flow is effectively disrupted during transfer and inspection of the substrates. Consequently, conventional metrology inspection methods can drastically increase overhead time associated with chip manufacturing. Further, because such an inspection method is conducive only to periodic sampling due to the negative impact on throughput, many contaminated substrates can be processed without inspection resulting in fabrication of defective devices. Problems are compounded in cases where the substrates are re-distributed from a given batch making it difficult to trace back to the contaminating source.

Thus, what is needed is an integrated metrology and process inspection system, a "gate-keeper" apparatus and method, capable of examining a substrate for selected characteristics which include particles, processing flaws, orientation, centerfinding, reflectivity, substrate type, discontinuity, etc. as an integral part of the processing system. Preferably, such an inspection can be performed prior to, during, and after substrate processing, thereby determining real time pre- and post-processing conditions of the substrate.

Other functions routinely performed in conventional processing systems and inspection systems include calibration of robots and the inspection equipment. Current methods of calibration negatively impact throughput because the production must be halted in order to perform the calibration. Degradation usually goes undetected until a catastrophic failure occurs. A preferred processing system would include an integrated, or embedded, device capable of continuously monitoring the status of the robot and inspection system and facilitate automatic corrective action. Thus, the processing system could be further integrated and throughput can be increased. In addition, it would be preferable for such an integrated device to be capable of monitoring robot behavior. Robot behavior of interest includes acceleration, speed, repeatability, stability, etc. Additionally, it would be preferable for such an integrated device to determine the presence of contamination on the robot blade which supports substrates during transfer. The presence of such contamination indicates that the backsides of substrates are being scratched during a substrate handling step or the accumulation of processing byproduct. Heretofore, however, no such integral devices or methods have been known to exist in processing systems.

Another disadvantage with conventional inspection systems is the prohibitive cost of the systems. Current systems are typically expensive stand-alone platforms that occupy clean-room space. As a result of the large area, or "footprint," required by the stand-alone inspection platforms, the cost of owning and operating such a system is high. With regard to particle detection, the cost is further increased because of the electro-optics equipment utilized. This equipment is configured to produce high-resolution detection of small-scale particles and requires high-fidelity mechanisms, which are expensive to operate. Additionally, considerations of reduced throughput described above further increase the cost of conventional inspection systems.

Therefore, there is a need for an integrated system capable of rapidly inspecting semiconductor substrates and determining one or more conditions of the substrate in order to detect anomalies and facilitate a subsequent substrate handling decision.

SUMMARY OF THE INVENTION

The present invention generally provides a substrate inspection system for use in substrate processing systems. In one aspect of the invention, at least one optical inspection system is used to inspect the surface topography of processed substrates. The optical inspection system transmits signals representing surface topographical characteristics of the substrate, at a particular process, to a process monitoring controller configured to operate one or more optical inspection systems.

In one embodiment, the process monitoring controller determines the state of the particular substrate surface with respect to a reference substrate value. If the substrate characteristics exceed a predetermined value, the substrate may be sent to a secondary metrology inspection step for a more refined and in-depth analysis. Moreover, the process monitoring controller may also utilize the information to optimize or alter the processing system substrate manufacturing processes.

In another embodiment, a plurality of optical inspection systems are used to monitor the substrate surface topography at various inspection locations positioned along a plurality of substrate transfer paths in conjunction with a process monitoring controller. Such a process monitoring system can optimize the throughput of the substrate processing through continued monitoring and analysis. The integrated inspection allows the optimization of process recipes through near real-time monitoring of process recipe changes and subsequent effects upon the process.

One embodiment of the invention involves a system for software control of the process inspection and system throughput enhancement. The system comprises a data-processing system comprising a controller containing a program for process monitoring. The program when executed on the data-processing system is configured to perform the steps comprising configuring a optical inspection system in response to a system configuration event; providing adjustment settings for the optical inspection system; receiving, from the optical inspection system, topographical information of the substrate surface, determining if the substrate topographical condition has exceeded predetermined values; and if the substrate surface has exceeded the predetermined values, determining if the substrate requires additional more in-depth analysis.

One embodiment of the invention includes a program product containing a program for optical character recognition and particle and defect detection, the program when executed by a controller comprises configuring a system in response to a system configuration event, providing adjustment settings for the system, providing a signal from a signal source to a receiver wherein the signal illuminates a substrate and the signal receiver receives reflections and/or scattered signal from the substrate surface to detect surface topographical defects.

Preferably, the program product is adapted to provide substrate positional information, substrate reflectivity information, specular information, spectral information, three-dimensional images, substrate defect information, substrate damage information, particle contamination information for the substrate support member and a substrate disposed thereon, alphanumeric character information, robot behavior information, calibration information for a robot, a transmitter unit and/or a receiver unit, and any combination thereof.

BRIEF DESCRIPTION OF THE DRAWINGS

A more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

FIGS. 8A–C are top views of the processing system of FIG. 6 showing various positions of a substrate disposed on a blade during linear movement of the blade.

DETAILED DESCRIPTION OF THE PREFERRED EMBODIMENT

I. Processing System

Embodiments of the invention have particular advantages in a multi-chamber processing system (e.g., a cluster tool). One exemplary multi-chamber processing system commonly used in the semiconductor industry, well suited for supporting the detection apparatus described herein, is known as a cluster tool. A cluster tool is a modular system comprising multiple chambers which perform various functions including substrate center-finding and orientation, degassing, annealing, deposition and/or etching. The multiple chambers are mounted to a central transfer chamber which houses a robot adapted to shuttle substrates between the chambers. The transfer chamber is typically maintained at a vacuum condition and provides an intermediate stage for shuttling substrates from one chamber to another and/or to a load lock chamber positioned at a front end of the cluster tool.

Figure 1A:
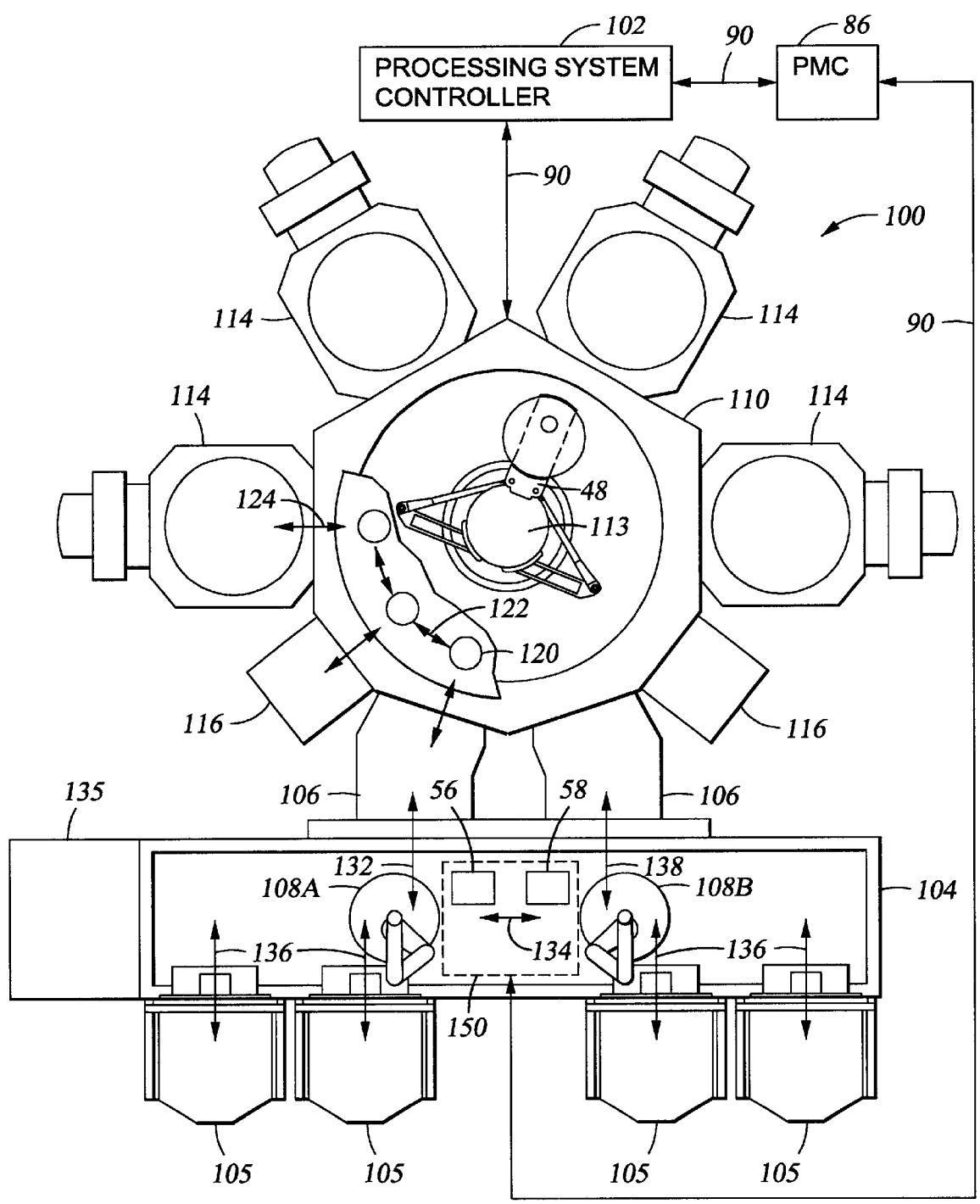
FIG. 1A is a plan view of a typical processing system for semiconductor processing wherein the present invention may be used to advantage.

FIG. 1A is a plan view of a typical processing system 100 for semiconductor processing wherein the present invention may be used to advantage. Two such platforms are the Centura® and the Endura® both available from Applied Materials, Inc., of Santa Clara, Calif. The details of one such staged-vacuum substrate processing system is disclosed in U.S. Pat. No. 5,186,718, entitled "Staged-Vacuum Wafer Processing System and Method," Tepman et al., issued on Feb. 16, 1993, which is incorporated herein by reference. The exact arrangement and combination of chambers may be altered for purposes of performing specific steps of a fabrication process.

In accordance with the present invention, the processing system 100 generally comprises a plurality of chambers and robots and is preferably equipped with a processing system controller 102 programmed to carry out the various processing methods performed in the processing system 100. A front-end environment 104 (also referred to herein as a Factory Interface or FI) is shown positioned in selective communication with a pair of load lock chambers 106. Pod loaders 108A–B disposed in the front-end environment 104 are capable of linear, rotational, and vertical movement to shuttle substrates between the load locks 106 and a plurality of pods 105 which are mounted on the front-end environment 104. The load locks 106 provide a first vacuum interface between the front-end environment 104 and a transfer chamber 110. Two load locks 106 are provided to increase throughput by alternatively communicating with the transfer chamber 110 and the front-end environment 104. Thus, while one load lock 106 communicates with the transfer chamber 110, a second load lock 106 communicates with the front-end environment 104. A robot 113 is centrally disposed in the transfer chamber 110 to transfer substrates from the load locks 106 to one of the various processing chambers 114 and service chambers 116. The processing chambers 114 may perform any number of processes such as physical vapor deposition, chemical vapor deposition, and etching while the service chambers 116 are adapted for degassing, orientation, cool down and the like. A number of view ports 120 provide visual access into the transfer chamber 110.

Embodiments of the invention include Optical Inspection Sub-Systems (OIS) 150 configured for gathering optical data. As will be described below, an OIS 150 generally comprises a transmitter unit adapted to provide a signal and a receiver unit adapted to receive reflected (bright field illumination) and/or scattered portions of the signal (dark field illumination) from the substrate surface.

A plurality of OISs 150 may be located anywhere on and/or coupled to the processing system 100 for process monitoring, for example within the factory interface 104, the transfer chamber 110, processing chamber 114, service chambers 116, and the like. The information received from each OIS 150 can then be processed to determine various conditions of substrates moving within the processing system 100.

Embodiments of the OIS 150 include various receivers and transmitters. In one embodiment, the receiver is a charge coupled device (CCD) camera used to detect light in the visible spectrum. Another receiver can be a spectrometer used to receive incoming light and to output data indicating the various light wavelengths and their intensity. For example, a red light would have greater light component intensities grouped within the lower wavelengths of the visible spectrum. The spectrometer typically includes an optical prism (or grating) interface to optically split the incoming signal into its components, which in turn is projected onto a linear CCD detector array. One embodiment of a spectrometer may comprise a CCD detector array comprising thousands of individual detector elements to receive the resultant spectrum from the prism (or grating). The relative intensity of the light spectrum components represents the overall color of, for example, a substrate surface, substrate surface pattern, or plasma process.

In another embodiment, the receiver is an optical character recognition receiver (OCR). OCR receivers are used to detect and discriminate between optical characters and substrate patterns. Substrates often include identifying information inscribed on a surface of the substrate. Typically, the identifying information is a series of alphanumeric characters. In one embodiment, an OCR receiver is used to advantage to detect the characters and determine whether a substrate having a specific OCR marking, is being handled properly (e.g., routed to the proper chamber for processing). In another embodiment, the OCR is used to associate related metrology information.

Each of the receivers may comprise optical devices to focus and collect the reflected/and or scattered signals from the substrate. For example, the spectrometer may utilize a fiber optic collector to receive and direct the light spectrum, or may use a "lens perspective system" such as a "fish-eye" to collect a large amount of light, or special lenses that can modify the field of view for a specific substrate inspection. Lens arrangements may be used to increase or concentrate light. Collecting more light over a greater field of view averages out local substrate surface variations.

The transmitters of the OIS 150 may be of various configurations adapted for a particular purpose during process inspection. For example, a line-light source may be used to only illuminate a portion of the substrate, or a flash device may be used to strobe the substrate during the process to gather spectral information. Each of the transmitters may incorporate a beam-focusing optical system to concentrate and project energy on to the substrate.

The various receiver and transmitter embodiments may be used individually or in combination to collect process data throughout the processing system 100. Data collected from the various embodiments is used to monitor the substrate processing status at various stages of the manufacturing process. The operation of the OISs 150 is controlled by an Process Monitoring Controller (PMC) 86. As shown in FIG. 1A, the PMC 86 is electrically coupled to each OIS 150 by an IO (input-output) cable 90 adapted to provide command signals to the respective OIS 150. Further, the PMC 86 receives output signals from the respective OISs 150 by the IO cable 90. Although the processing system controller 102 for the processing system 100 is preferably separate from the PMC 86, in one embodiment the PMC 86 may serve as the control unit for the processing system 100, thereby eliminating the need for an additional control unit.

Upon initiation by a user, the PMC 86 continues to monitor substrates which enter the field of view of the OIS 150. If the PMC 86 detects a condition being monitored (e.g., a contaminated substrate), the user may be alerted by a warning message displayed on a display unit (not shown). Additionally or alternatively, the processing system controller 102 can be instructed by the PMC 86 to transfer the substrate to a particular location for eventual disposition, cleaning or further inspection. For example, in one embodiment, the processing system 100 includes an inspection platform 135 for particle detection but the inspection platform 135 function could be expanded to include OISs 150 on the FI 104, and elsewhere on the processing system 100.

The inspection platform 135 could be adapted to perform various metrology tasks such as surface anomaly detection, pattern recognition, spectral/spectrum analysis, and the like in conjunction with particle detection. Illustratively, the inspection platform 135 is an integrated particle monitoring (IPM) system which is configured for embodiments of the present invention. In general, an IPM is a particle inspection platform commonly used on cluster tools. One IPM which can be used to advantage is known as Excite™ available from Applied Materials, Inc, of Santa Clara, Calif. When implemented according to the present invention, the IPM operates as a process monitoring device capable any of the present inventive processes, including any equivalents. Accordingly, the inspection platform 135 is capable or more than mere particle detection.

In one embodiment, the particular location for an OIS 150 is determined by the routing of substrates within the processing system 100 (in order to use the robots to advantage) as well as accessibility of the location. For example, the view ports 120 provide suitable locations for an OIS 150 because the view ports 120 provide a field of view of the robot blade 48 entering or exiting a chamber (e.g., the load lock 106, cooldown chamber 116 or processing chamber 114) or moving between locations within the transfer chamber 110. Illustratively, arrows 122, 124 indicate points where optical inspection of a substrate may be performed using the ports 120. Arrows 122 represent points where the robot blade 48 is rotated and arrows 124 represent points where the robot blade 48 is extended or retracted. One embodiment wherein an OIS 150 is located on the transfer chamber 110 is described below with reference to FIG. 6.

In some embodiments, the OIS 150 has application at any position in the processing system 100 where substrates are in motion. In one embodiment, the factory interface 104 provides additional inspection sites. Illustrative inspection sites are represented by arrows 132, 134, and 138. Arrows 132, 134, 136, and 138 additionally illustrate the substrate transfer paths. Arrows 136 indicates the movement of substrates between the factory interface 104 and the pods 105. Arrows 132 and 138 indicate the movement of substrates between the factory interface 104 and the load locks 106. Arrows 134 indicate the movement of substrates within the factory interface 104 and, in particular, between the pod loaders 108A and 108B. OISs 150 may be located along each of the transfer paths 132, 134, and 138, to monitor the manufacturing process. However, as will be described below, embodiments are also contemplated in which the substrate being inspected is not moving.

Figure 1B:
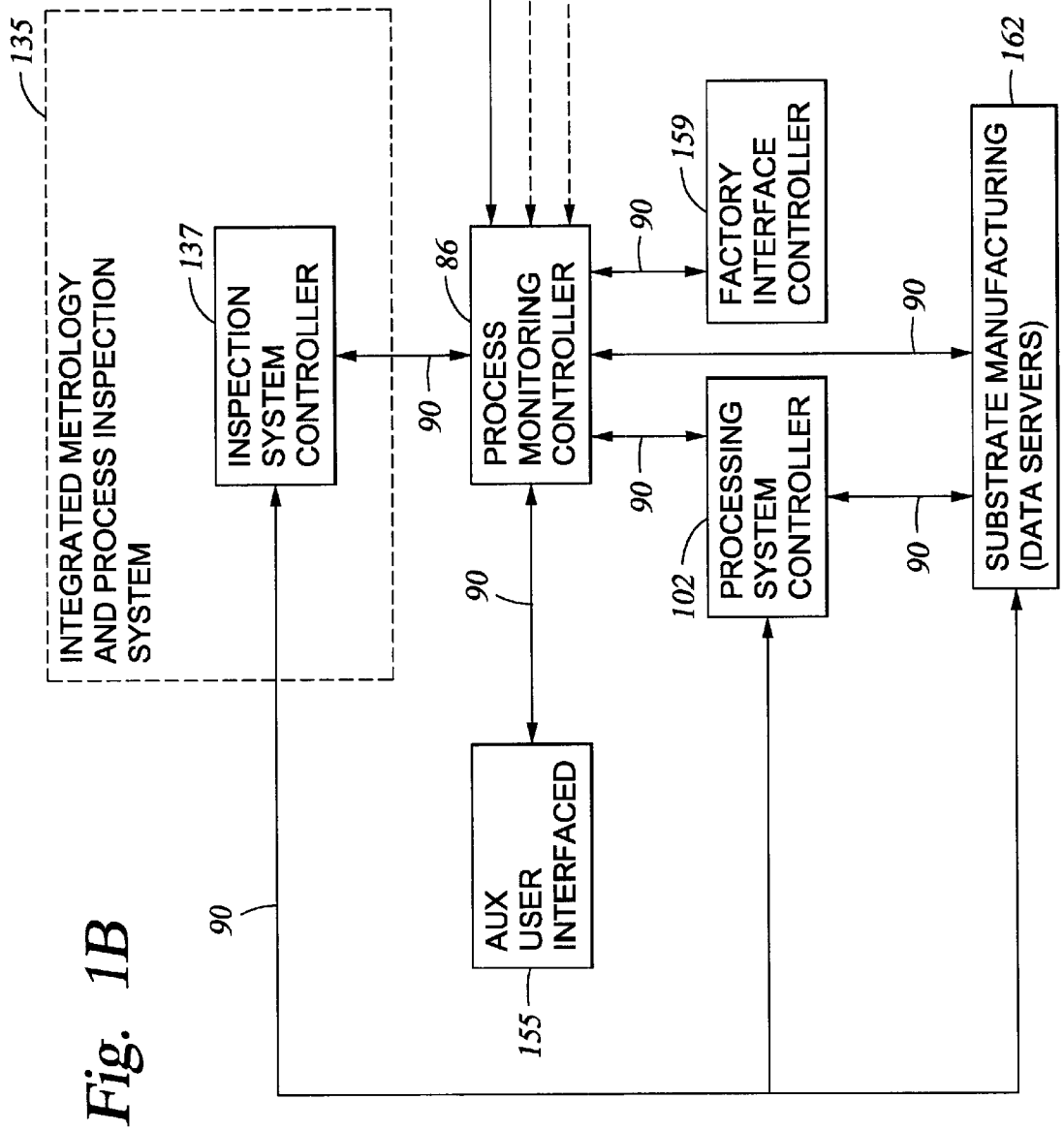
FIG. 1B is a high-level system view of a processing inspection system.

FIG. 1B illustrates a high level view of a substrate inspection system. In one embodiment, the inspection system comprises a PMC 86, coupled to a processing system controller 102, a factory interface controller 159, a plurality of OISs 150 and a inspection system 135. The PMC 86 is used to control the process monitoring of the OISs 150. The auxiliary user interface 152 allows for stand alone operation allowing an operator to control PMC 86. In one embodiment, interface 152 may be a Graphical User Interface (GUI). The process monitoring information obtained may be directed to substrate manufacturing data servers 162 via cable 90.

Figure 1C:
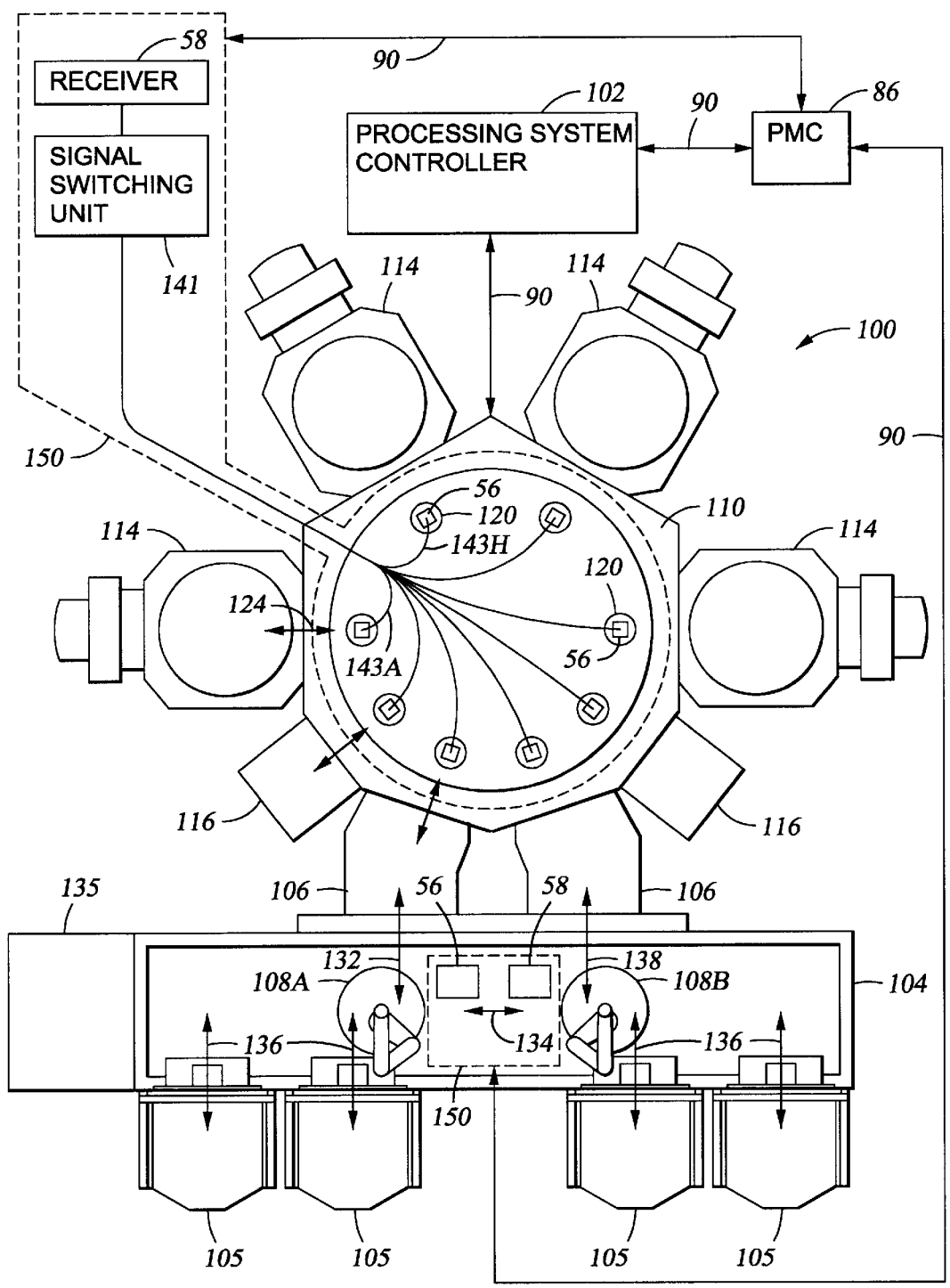
FIG. 1C illustrates a process inspection system comprising one embodiment of the invention having a plurality of optical inspection systems coupled to an optical signal multiplexer that is in communication with receiver for use with the present invention.

For example, in one embodiment, the OIS 150 may include a cluster of light sources and one receiver. FIG. 1C illustrates a plurality of light sources 56 and fiber optic cables 143A–H coupled to an optical signal multiplexer 141 that is in communication with receiver 58. The optical cables are positioned to collect reflected and/or scattered light through windows 120 and then send optical signals to multiplexer 141. Mutliplexer 141 sends optical data to the spectrum analyzer 58 in multiplexed form allowing a single receiver to effectively monitor a multitude of inspection sites. In one embodiment, the receiver 58 is a spectrometer.

Figure 2:
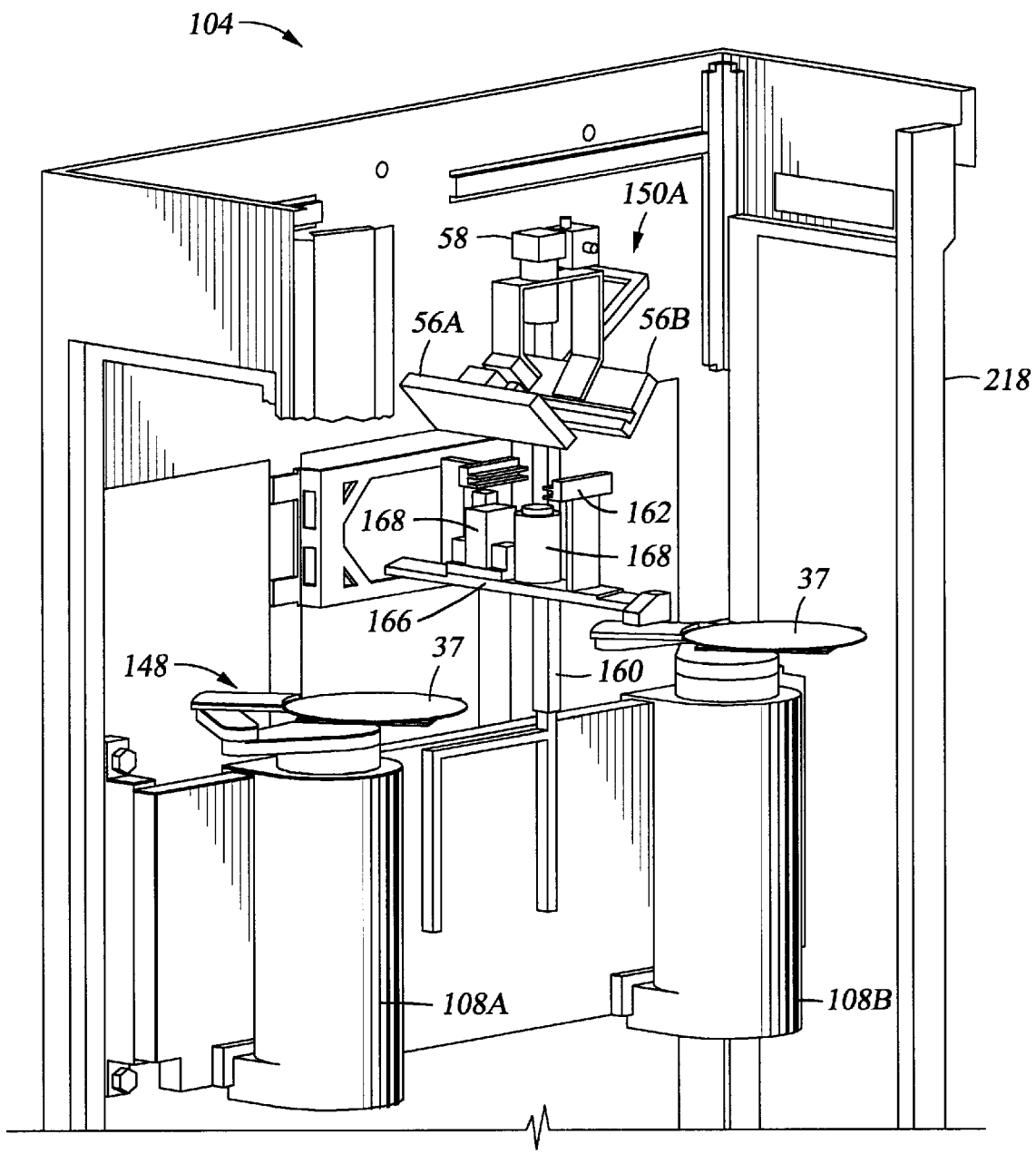
FIG. 2 is a perspective view of a Factory Interface used with the present invention comprising one embodiment of the present invention comprising two transmitter units and a receiver unit for use with the present invention.
Figure 4:
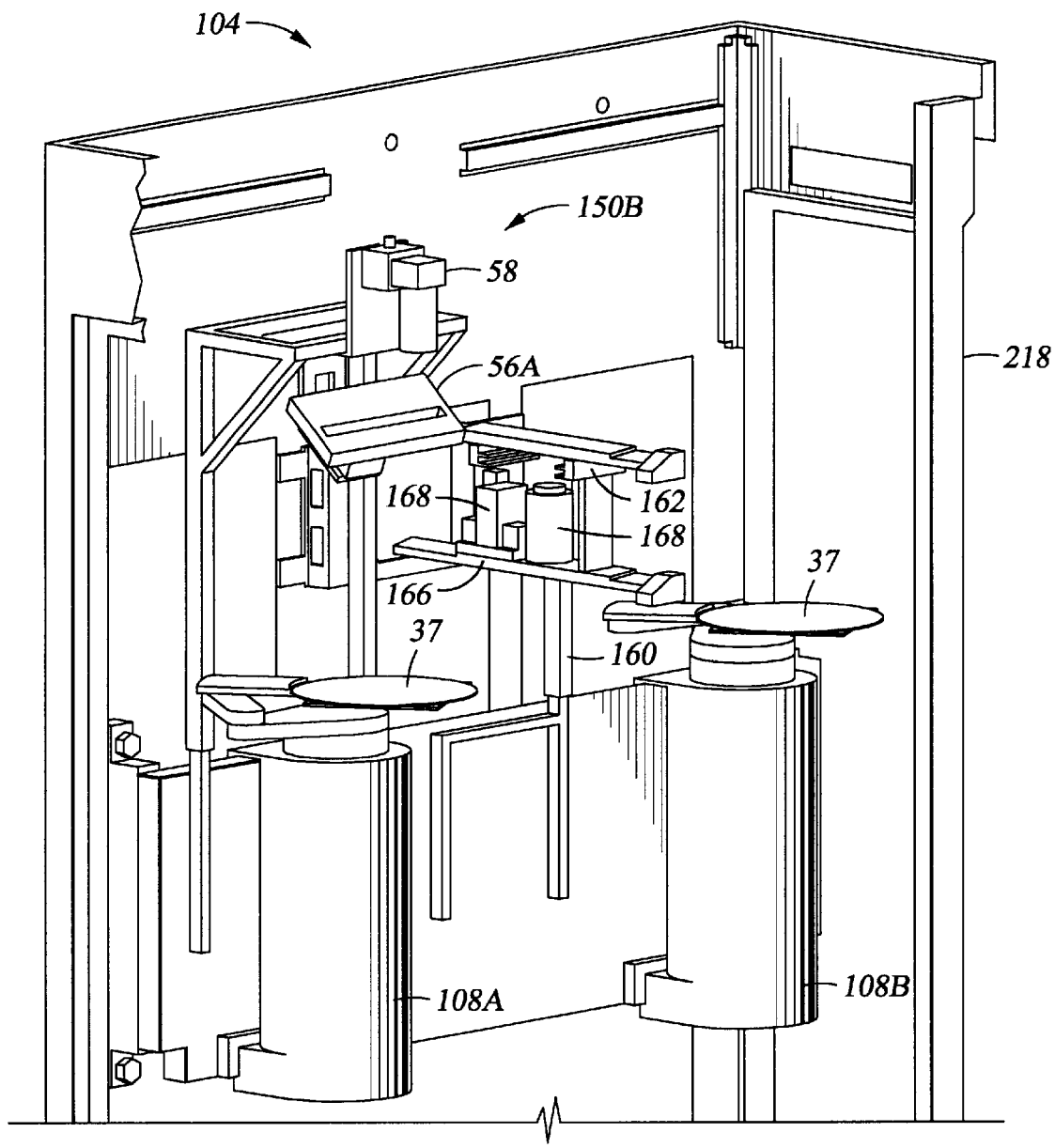
FIG. 4 is a perspective view of a Factory Interface used with the present invention comprising one embodiment of the present invention comprising one transmitter unit and a receiver unit.

II. Factory Interface:

FIGS. 1, 2, 4 illustrate embodiments wherein the transmitter unit and the receiver unit of the OIS 150 are disposed on or in the FI 104 along the various paths of substrate movement as illustrated by arrows 132, 134, 136, 138, other embodiments may be used to advantage. FIG. 2 shows is an illustrative view of the FI 104 comprising the pod loaders 108A and 108B, OIS 150A, mounting member 160, a transfer support member 166 including a substrate alignment detector 168, and a substrate holder 162. The FI further comprises a frame 218. The mounting member 160 is fastened to the frame 218 by conventional means such as bolts, clamps or other fasteners as are known in the art.

FIG. 2 illustrates one embodiment of the OIS 150 used for substrate scanning along process arrow 134. An OIS 150A comprising a pair of light sources 56A and 56B (i.e., transmitters), and a receiver 58A are disposed upon mounting member 160. The light sources 56A and 56B are angled to provide two angles of illumination. Illustratively, light source 56A provides front substrate illumination and light source 56B provides rear substrate illumination. In one embodiment, the angle between the light sources 56A and 56B is at about orthogonal to provide the least amount of illumination overlap (i.e. illumination cross-talk). Although not shown, the light sources 56A and 56B may include beam-shaping optics (e.g., lenses and the like) to allow for refinement and adjustment of the optical beams provided by the respective light sources. The light receiver 58 is positioned to receive reflected and/or scattered portion of the light from the surface of the substrate 37. The light receiver 58 is selected according to the data to be collected. In illustrative embodiments, the light receiver 58 comprises a CCD device, a time delay integration (TDI) camera, a photo-multiplier tube (PMT) a spectrometer, an OCR camera and the like. The light receiver 58 may further include optics devices adapted to assist in the collection of information. For example, in one embodiment, the light receiver 58A includes a fiber optics bundle to capture and route the received light from an inspection point to the receiver 58.

In operation, the substrate 37 is moved between locations in the F1 by the pod loaders 108A and 108B. The OIS 150A then scans the substrate 37 such that the reflected and/or scattered light is received by the light receiver 58 for processing as described below.

Illustratively, the substrate 37 is positioned by either pod loader 108A or 108B under the OIS 150A for scanning as the substrate 37 is being shuttled between the load locks 106 and substrate holder 162. Preferably, the substrate 37 is scanned during a normal substrate handling. For example, during a normal substrate exchange step between pod loaders 108A and 108B, the substrate 37 may be scanned by OIS 150A while in transit.

Figure 3A:
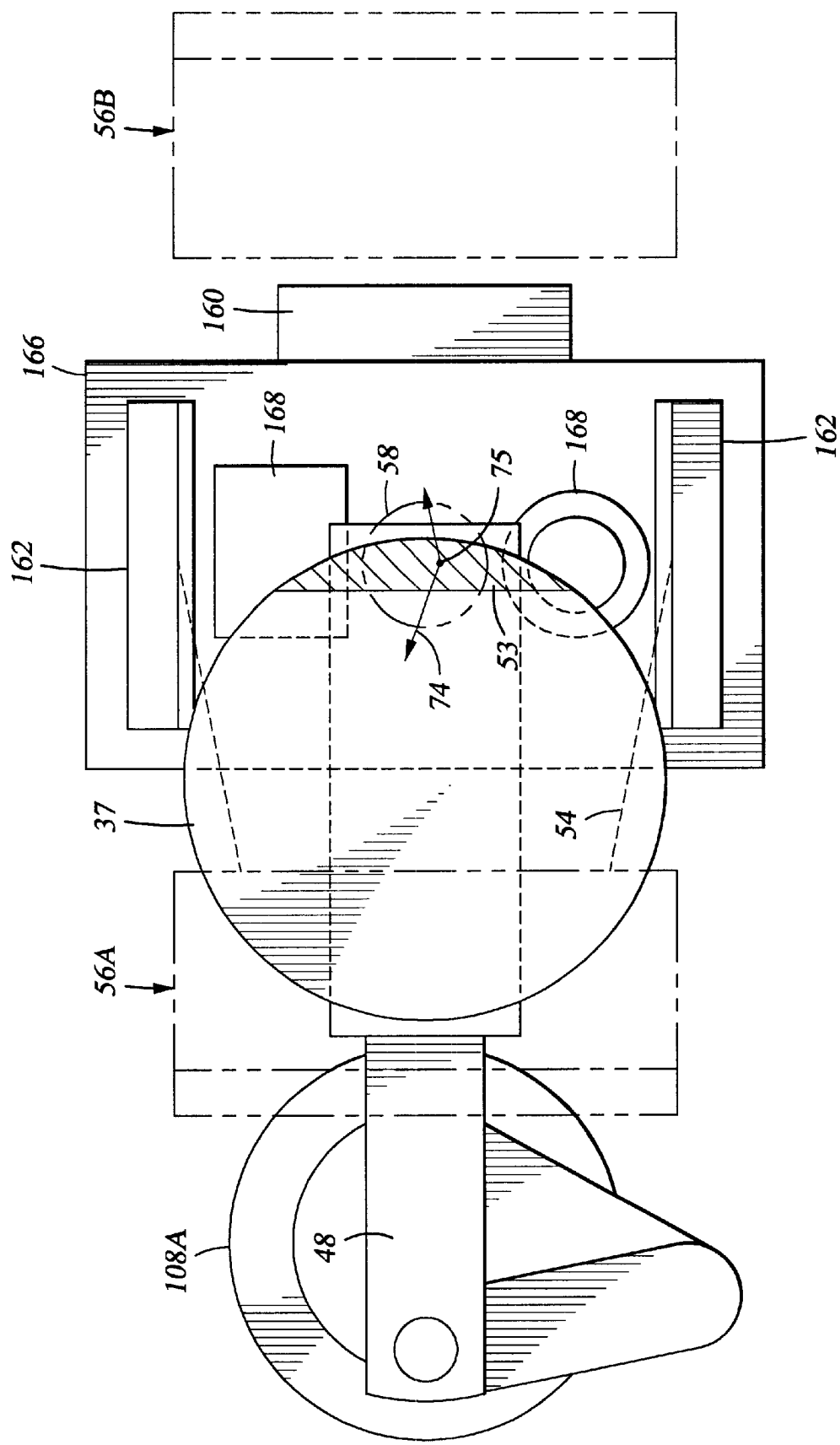
FIGS. 3A–C are top views of the processing system of FIG. 2 showing various positions of a substrate disposed on a blade during linear movement of the pod blades.
Figure 3B:
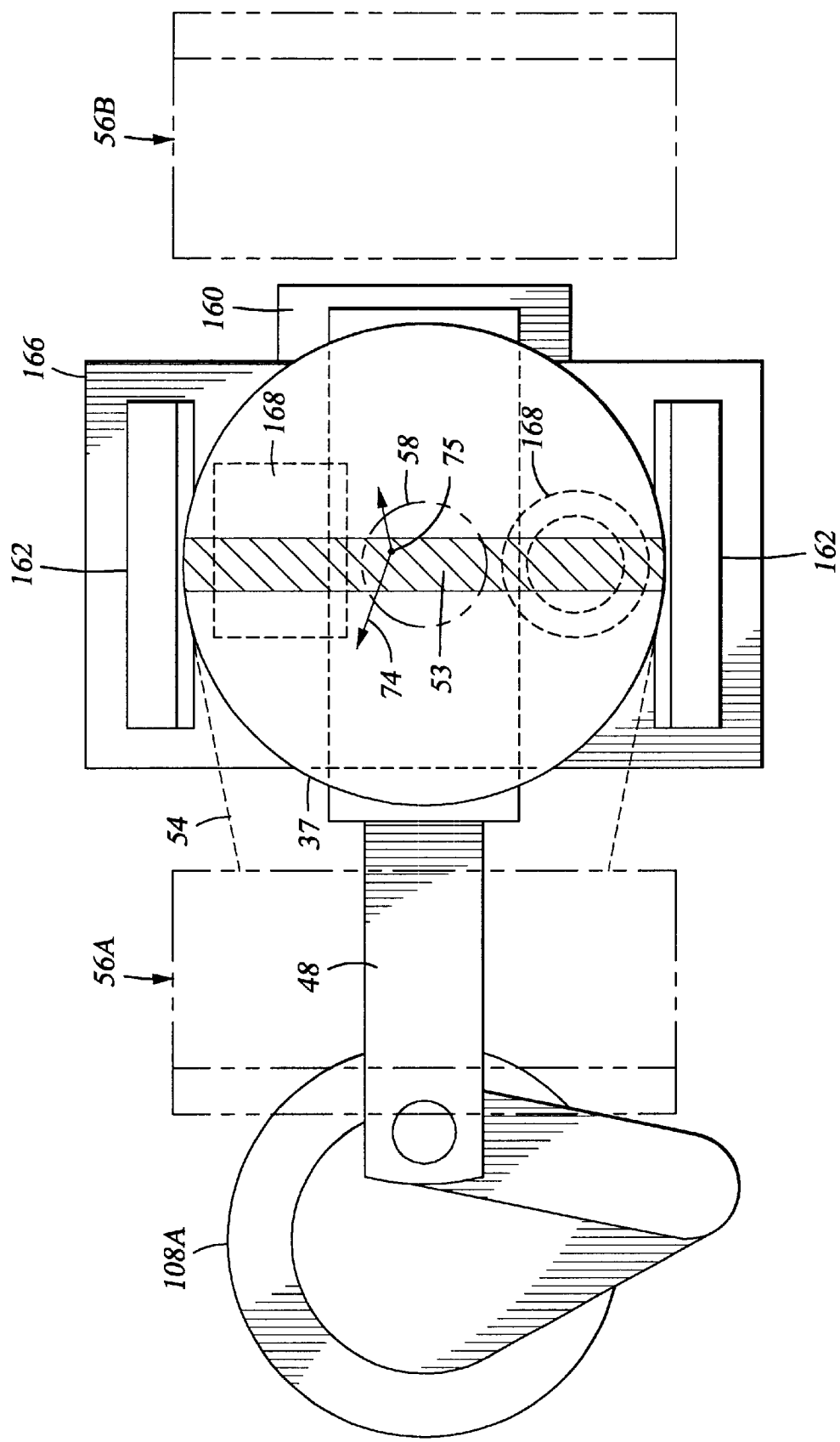
Figure 3C:
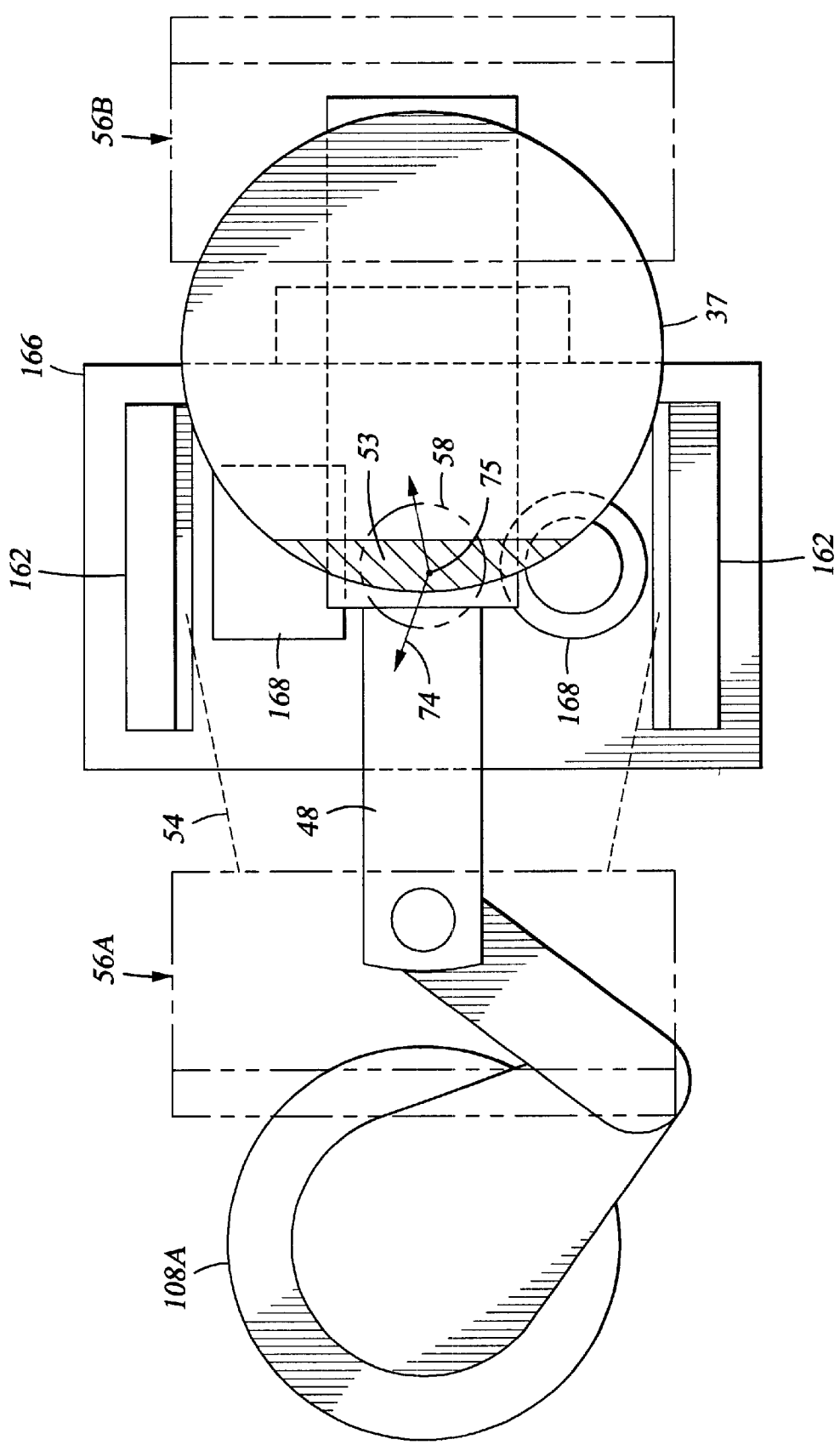

For example, consider the case where the substrate 37 is being moved from pod loader 108A to the pod loader 108B. Initially, the substrate 37 is carried by pod loader 108A and placed in substrate holder 162. Substrate holder 162 facilitates the passthrough/exchange between the pod loaders 108A-B. During this movement, the substrate 37 can be scanned by the front illumination light 56A. In one embodiment, the substrate is moved beyond midpoint for a full substrate scan. 3A-C illustrates the movement of the substrate 37 as it is scanned with the front illumination light 56A. FIG. 3A shows the pod blade 48 immediately after initiating the movement of the substrate 37 toward the substrate holder 162 so that the leading edge of the substrate 37 is positioned in the path of the signal 54. Thus, a portion of the light projection 53 formed by light source 56A, represented by the shaded area, is shown intersecting the leading edge of the substrate 37. During the continued movement of the pod blade 48 as shown in FIGS. 3B-C, the light projection 53 scans the upper surface of the substrate 37. Reflected and/or scattered light is received by receiver 58 for processing as described below. Pod loader 108B may use the identical process as described above to scan the substrate 37.

In another embodiment, it is contemplated that a single pod loader 108 may be used for movement utilized by the two light sources 56A and 56B. For example, OIS 150A scans the substrate using the front illumination light source 56A and receiver 58 as the substrate is loaded into substrate holder 162 by pod loader 108A. When the substrate is withdrawn from the substrate holder 162 by pod loader 108A, light source 56B is activated to provide rear illumination for scanning the substrate as the substrate is withdrawn from the substrate holder 162. Receiver 58A receives the reflected and/or scattered light from the substrate as it is being placed upon substrate holder 162 and withdrawn by pod loader 108A.

FIG. 4 illustrates another embodiment of an OIS 150B used when the substrate follows the transfer path as illustrated by arrows 132, 138. OIS 150B comprises a single light source 56A which may include beam-shaping optics, and a light receiver 58. OIS 150C is disposed upon mounting member 160. The light source 56A provides substrate illumination and may include beam-shaping optics. In one embodiment, as the substrate 37 is moved from the factory interface 104 into the load locks 106, the reflected and/or scattered light is received by receiver 58 which sends signals to the PMC 86 for processing as described below.

Figure 5A:
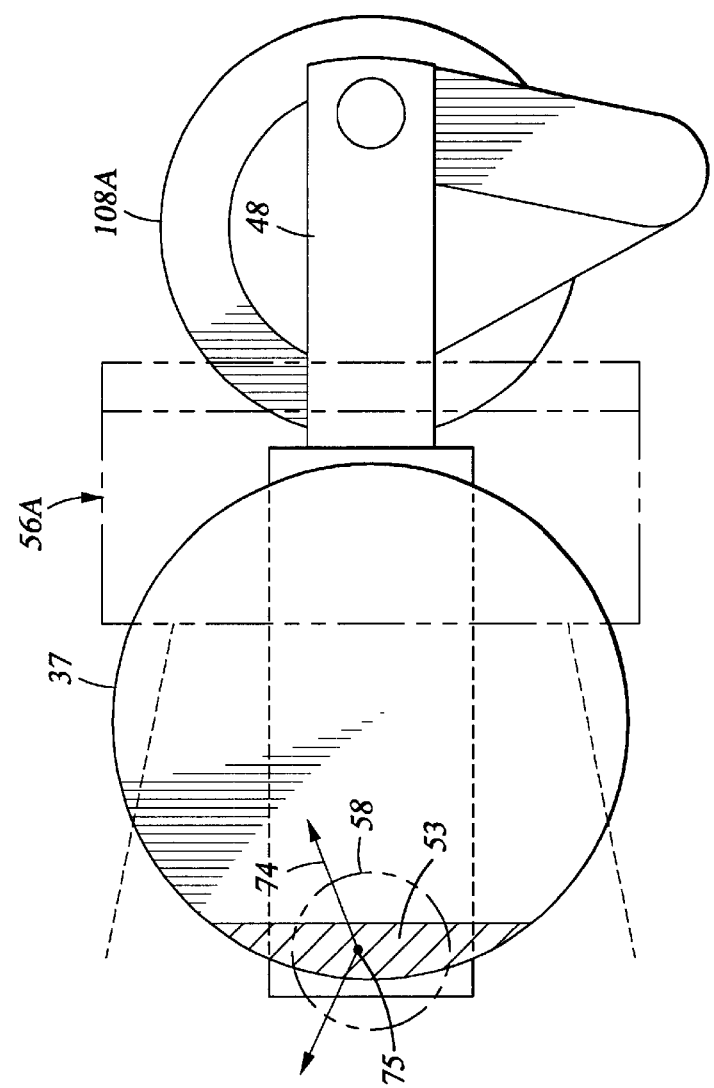
FIGS. 5A–C are top views of the processing system of FIG. 4 showing various positions of a substrate disposed on a blade during extension movement of the pod blade.
Figure 5A:
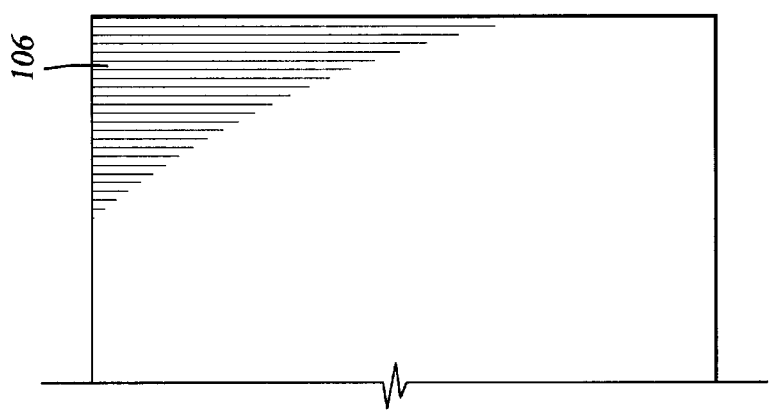
Figure 5B:
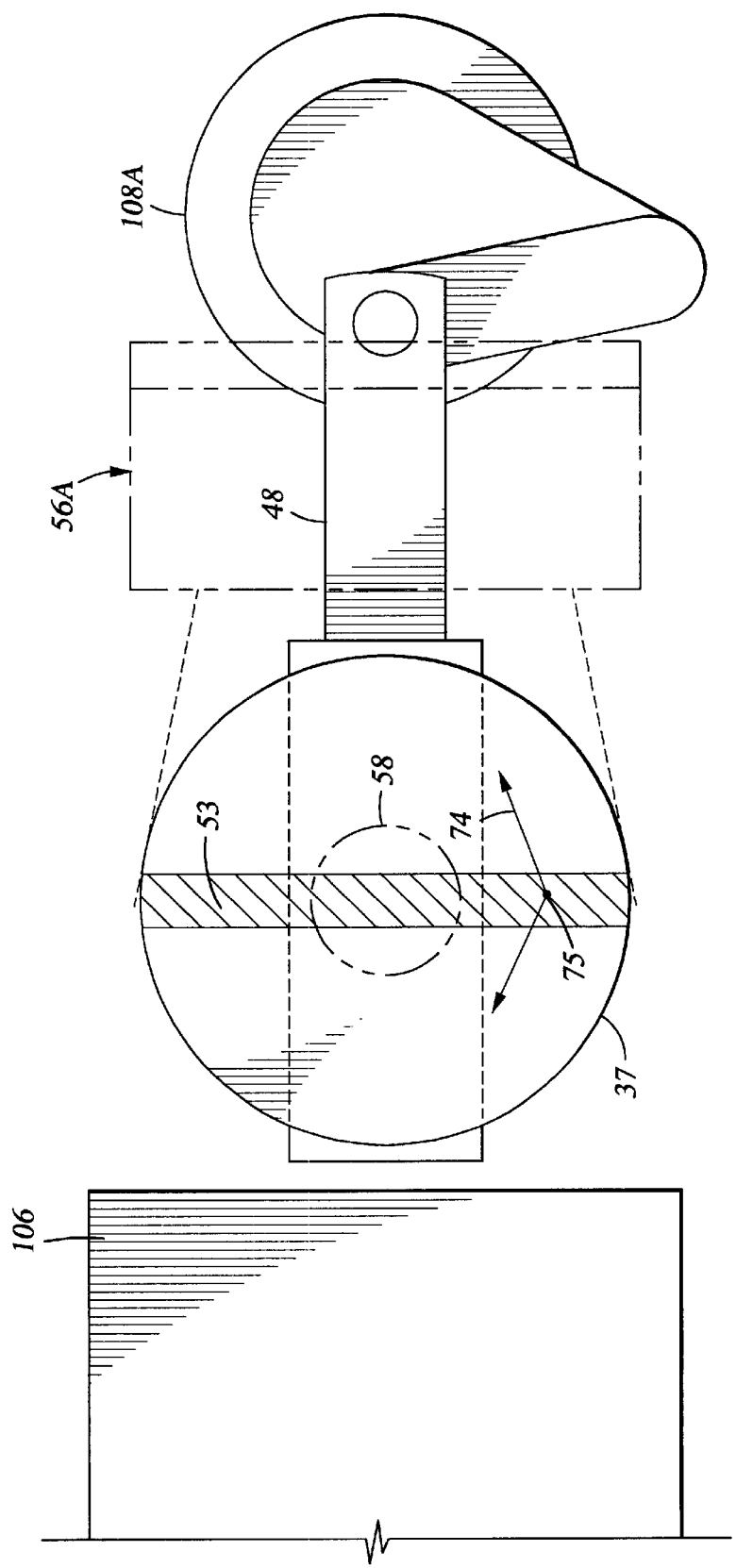
Figure 5C:
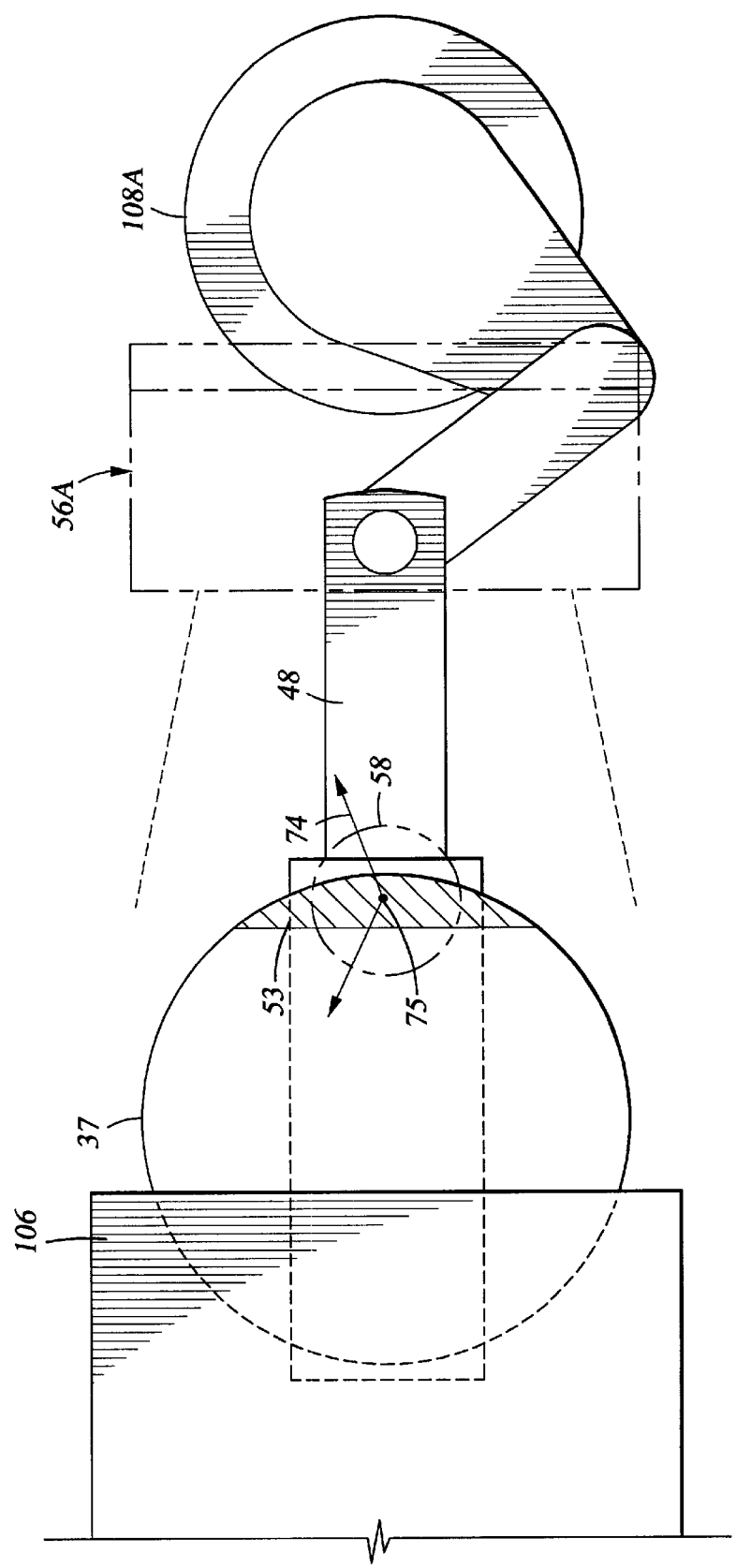

FIGS. 5A-C illustrate the sequence of the scan using OIS 150B. FIG. 5A shows the pod blade 48 immediately after initiating the movement of the pod 108A toward the load lock 106 so that the leading edge of the substrate is positioned in the path of the signal 54. Thus, a portion of the light projection 53, represented by the shaded area is shown intersecting the leading edge of the substrate 37. During the continued movement of the pod blade 48 as shown in FIGS. 5B-C, the light projection 53 scans the upper surface of the substrate 37. Reflected and/or scattered light is received by receiver 58 for processing as described below.

As noted above, the receiver in each embodiment of the OIS 150 may be selected from any of a CCD device, a time delay integration (TDI) camera, a photo-multiplier tube (PMT), a spectrometer, an OCR camera and the like. In general, CCDs, TDIs and PMTs are configured to collect image intensity variations across the substrate for specular signature analysis and variances associated flake/particle contamination. The spectrometer is configured to gather the light signal reflected/scattered from surface of the substrate 37 and generate an output representing the color spectrum components of the signal. The OCR gathers the light signal reflected/scattered from surface of the substrate 37 and generates an output representing the optical characters disposed on the upper surface of the substrate 37. In any case, optics devices may be utilized to advantage. For example, in the case of the spectrometer, the received light signals may be propagated from a collection point to the spectrometer via a fiber optics bundle. Additionally, a diffuser lens may be coupled to the fiber-optic bundle to be used to effectively increase the field of view and send the spectrometer an averaged light spectrum of the image.

Alternatively, the receiver of the OIS 150 may include a combination of detector devices. For example, one embodiment of the receiver comprises a spectrometer and a CCD camera. In such a case, the spectrometer may be positioned adjacent to the CCD camera in a manner to allow both devices to share the same field of view of the substrate 37. Such embodiments allow for multiple methods of process monitoring without significant increases to the data acquisition time. Illustrative process monitoring methods are described in more detail below.

It should be understood that the relationship of the transmitters (i.e., the light sources) and the receivers are merely illustrative. In each embodiment described above, the positions of the receivers and the transmitters may be reversed. For example, with regard to FIG. 2, the OIS 150A may comprise a pair of receivers mounted where the light sources 56A–B are shown. A light source can then be mounted where the receiver 58A is shown. In such an embodiment, the receivers are about obliquely angled with respect to the upper surface of a substrate positioned directly below the light source. In operation, the receivers are positioned to receive reflected and/or scattered portion of the light from the surface of the substrate 37. As the substrate 37 is moved between pod loaders 108A and 108B, the OIS 150A scans the substrate 37, the reflected and/or scattered light is then received by the receivers for processing as described below. The movement of the substrate 37 between pod loaders is identical to that shown in FIGS. 3A–C.

Figure 6:
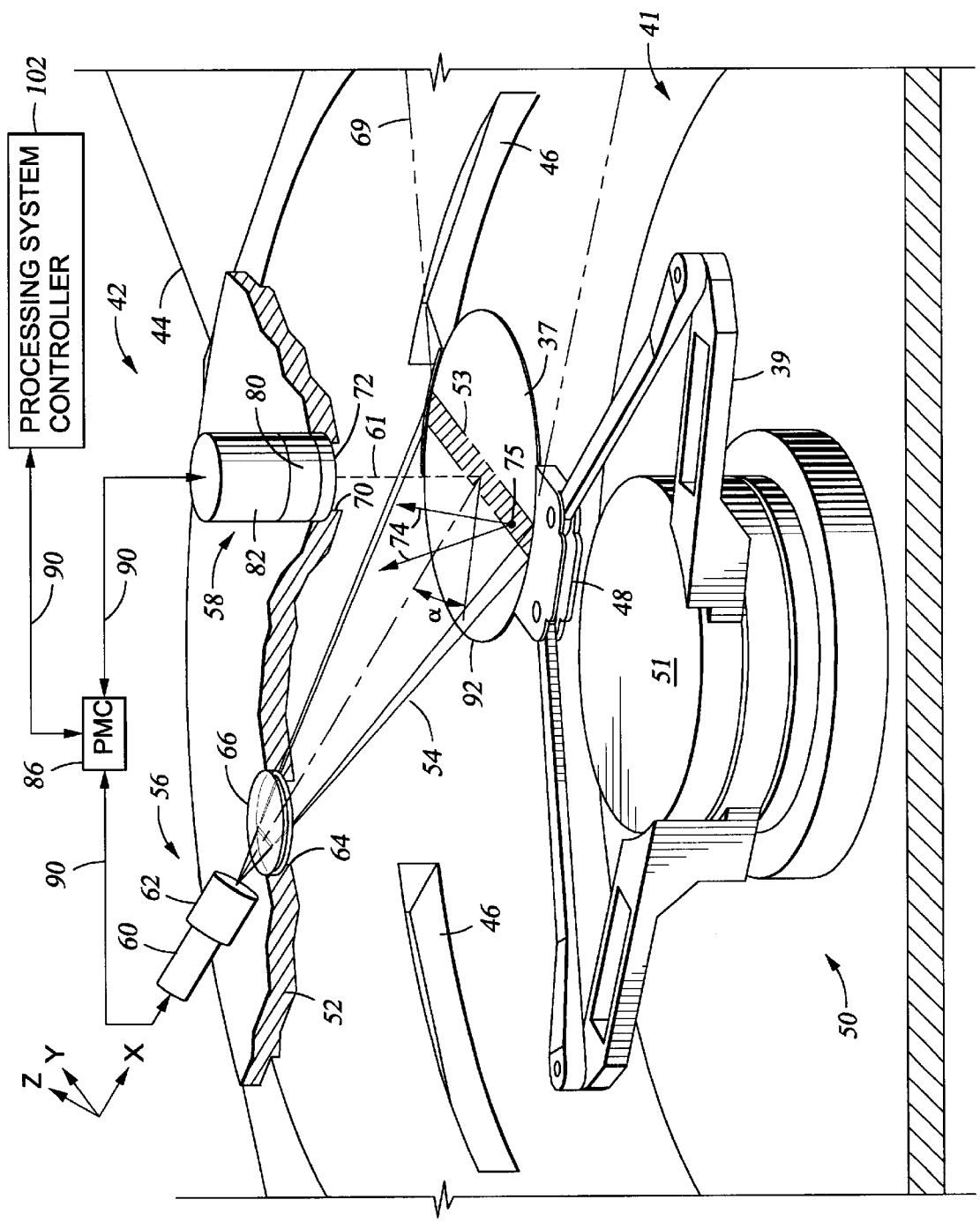
FIG. 6 is a partial perspective view of a transfer chamber used with the present invention comprising one embodiment of the present invention comprising one transmitter unit and a receiver unit.

III. Transfer Chamber:

FIG. 6 is a perspective cutaway of a processing system 100 of the present invention comprising a transfer chamber 42 and a vacuum chamber 44 mounted thereon (see FIG. 3A–C). The transfer chamber 42 and the vacuum chamber 44 are selectively communicable through an aperture 46 which can be sealed by a conventional apparatus such as a slit valve door window located above the slit valve door (not shown). The aperture 46 is sized to accommodate the transfer of substrates there through. A robot 50 is centrally disposed in the transfer chamber 42 and comprises a blade 48 configured to hold the substrate 37 coupled to the robot hub 51 by frog-leg type linkage 39. The robot 50 enables rotational and radial movement of the blade 48 along a transfer plane, thereby shuttling substrates between various positions within the system. The transfer chamber 42 and the vacuum chamber 44 are preferably components of a processing system 100 such as the one shown in FIG. 1A. Thus, the vacuum chamber 44 may be a load lock chamber 106 providing an interfacing chamber between a front-end environment and the transfer chamber 42, while the transfer chamber 42 provides a vacuum environment communicable with various peripheral chambers. Alternatively, the vacuum chamber 44 may be a process chamber, such as a cooldown chamber or orientation chamber as shown in the embodiment described below in reference to FIGS. 12A–C.

As shown in FIG. 6 a transmitter unit 56 and a receiver unit 58 are externally mounted to a lid 52 of the transfer chamber 42. In one embodiment, the transmitter unit 56 includes a light source 60 and beam-shaping optics 62 and is positioned to emit a signal 54 into the cavity 41 of the transfer chamber 42 via a view port 64. The view port 64 comprises an opening formed in the lid 52 and is hermetically sealed with plate 66 made of a material transparent to the signal 54 of the light source 60. In one embodiment, the plate 66 may comprise Quartz Glass™, for example, or any energy transparent medium such as glass, transparent polymers, GaAr, and the like, adapted to allow the transmission of the light.

In operation, the signal 54 propagates parallel to the x-axis shown in FIG. 2 and is directed onto an upper surface of a substrate 37 rotating (or otherwise moving relative to the signal 54) through the cavity 41 of the transfer chamber 42. The signal defines a light projection 53 upon falling on the substrate 37. As described in detail below, the spot size of the light projection 53 may be varied according to the substrate size by adjusting the beam shaping optics 62 and the position of the light source 60.

In one embodiment the light source 60 can be, for example, a coherent light source such as a laser, a non-coherent broad-spectrum light source, or other non-coherent narrow spectrum source such as infrared. In other embodiments, the light source 60 may include illumination signals such as radio frequencies, microwaves, and the like. In general, the light source 60 is selected according to scattering intensity, brightness and cost. Where a laser source is used, the laser source is preferably operable at about 808 nm. However, other laser sources, such as 650 nm or 680 nm wavelength laser sources, may also be used.

In general, the spot size of the light projection 53 is substantially determined by the beam-shaping optics 62 and the position of the transmitter unit 56 relative to the substrate surface plane. The beam-shaping optics 62 is selected to provide a spot size according to the dimensions of the substrate. In one embodiment, the spot is concentrated into a tight light-line. The width of the line allows for accommodating the blade movement (e.g., vertical movement) across the light-line. For a 260 mm substrate, for example, the spot size of the light projection 53 is preferably at about 1 mm (width) and at about the width of the substrate 260 mm (length, y-axis) on the upper surface of a substrate. Thus, in operation, the entire breadth of a 260 mm substrate is exposed to the signal 54 after a single scan. However, in other embodiments, only a portion of the substrate is exposed to the signal 54. With regard to particle detection, for example, typical sources of catastrophic process chamber contamination, such as flaking (also known as chamber excursions), provide hundreds of particles that may settle on the processing surface of a substrate. Although it is preferable to inspect the full substrate, successful process inspection often requires that only a portion of the contamination be to confirm the presence of a contaminated substrate. Process monitoring for other substrate characteristics (e.g., film thickness, end point confirmation, etc.) may also be accomplished with a limited surface inspection.

The receiver unit 58 is shown mounted in a view port 70 formed in the lid 52 and defines a signal path 61 toward the substrate 37 moving through the cavity 41. The receiver unit 58 is secured above an energy transparent plate 72 made of a material selected according to the operating wavelength of the signal 54 and preferably is made of the same material as the plate 66 disposed in view port 64. For example, where the signal source 60 is a laser source operating at about 808 nm, the material for the plates 66, 72 is selected to accommodate an 808 nm signal. The receiver unit 58 is positioned to receive a scattered portion 74 of the signal 54 from the substrate 37 during operation. The scattered and/or reflected portion 74 is represented by a multiplicity of arrows oriented at various angles relative to the upper surface of the substrate 37 and indicates the presence of an obstruction, such as particulate contamination or a device pattern disposed on the upper surface of the substrate 37. A reflected portion 69 of the signal 54 propagates at angles relative to the substrate 37 substantially equal to the angle of incidence $\alpha$. The reflected portion 69 represents the portion of the signal 54 substantially unobstructed upon intercepting the upper surface of the substrate 37.

The receiver unit 58 includes an optics assembly 80 comprising one or more lens and a detector 82. The detector 82 of the receiver unit 58 preferably comprises a charge-coupled device (CCD) line camera. A CCD line camera is a preferred detector because the angular relationship between the source and the receiver can be maintained across the full substrate thus producing a consistent illuminated receiving environment. By using a CCD line camera to successively scan a substrate in motion in the receiving environment, an image is formed. However, while CCD detectors are preferred, other detectors, including time delay integration (TDI) cameras, or photo-multiplier tubes (PMT's) may be used to advantage in embodiments of the invention. In other embodiments, the receiver unit 58 is selected from one or more of a spectrometer and an OCR receiver.

The foregoing description for positioning the transmitter unit 56 and receiver unit 58 is merely illustrative and other embodiments are possible. For instance, while FIG. 6 shows the transmitter unit 56 and the receiver unit 58 disposed outside the cavity 41 of the transfer chamber 42, in another embodiment the transmitter unit 56 and the receiver unit 58 are positioned inside the cavity 41, and thus, under vacuum conditions. In another embodiment, mirror surfaces can be located in the cavity 41 to allow more critical angles to be achieved.

Figure 7A:
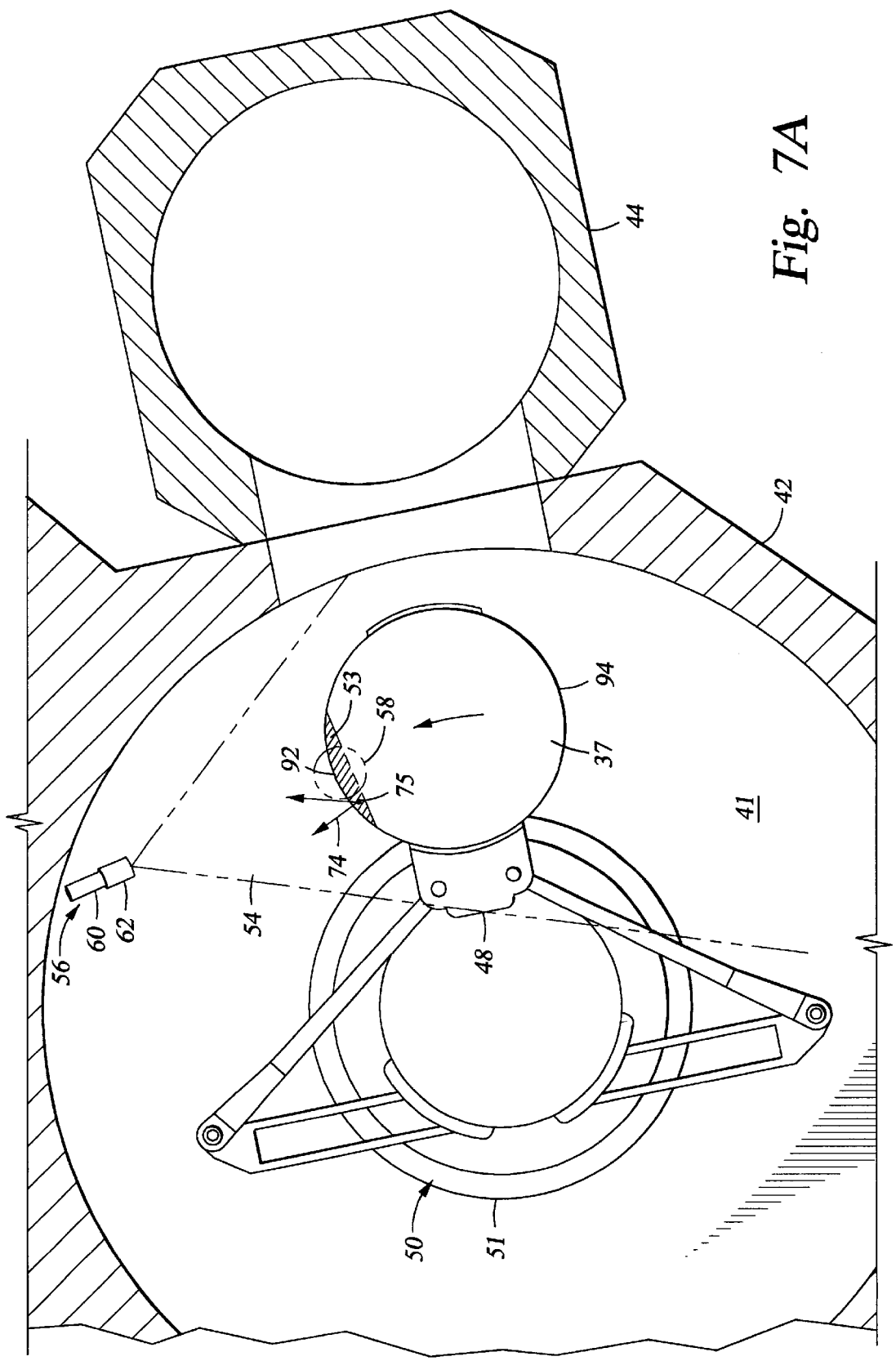
FIGS. 7A–C are top views of the processing system of FIG. 6 showing various positions of a substrate disposed on a blade during rotation of the blade.
Figure 7B:
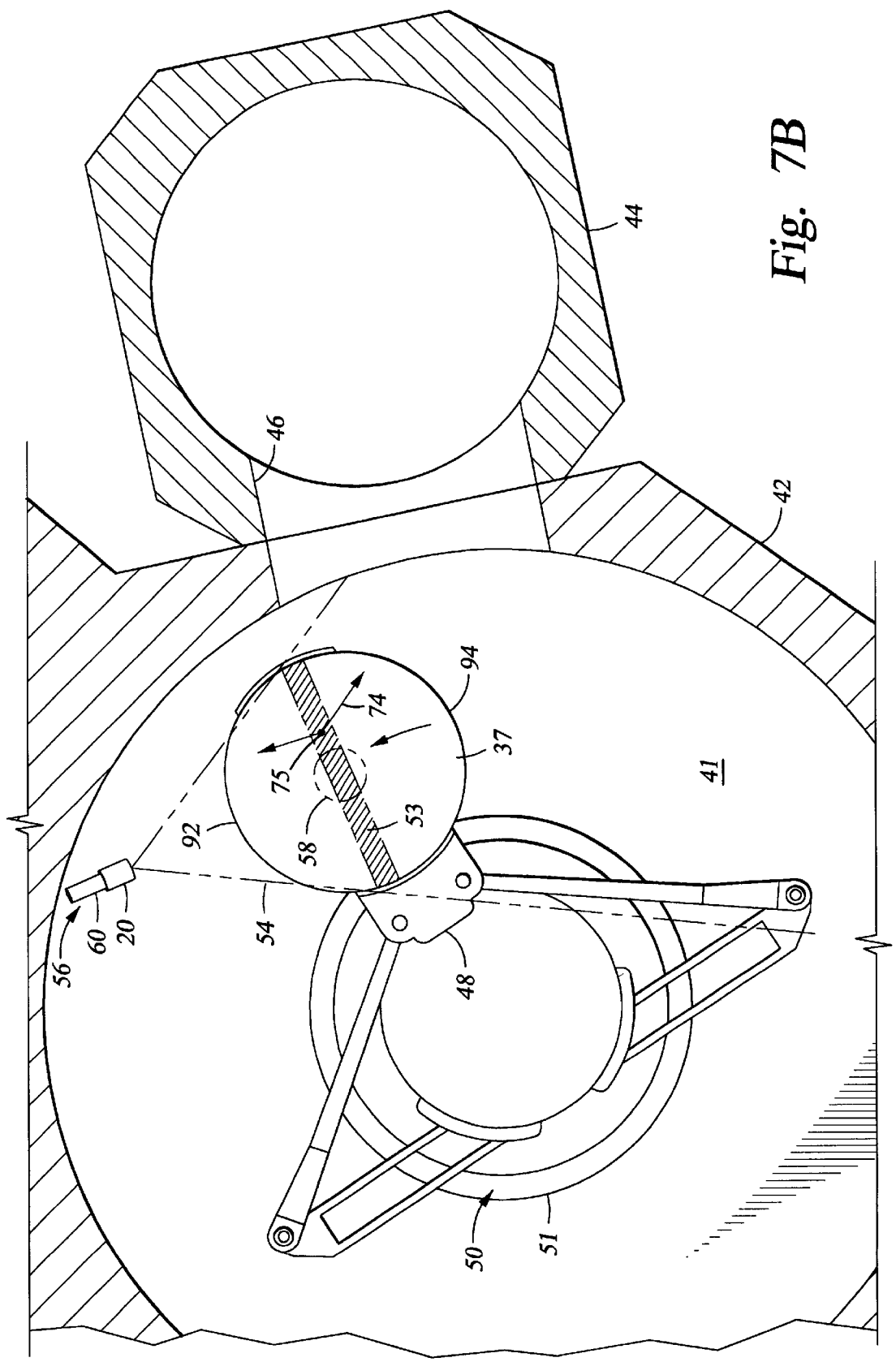
Figure 7C:
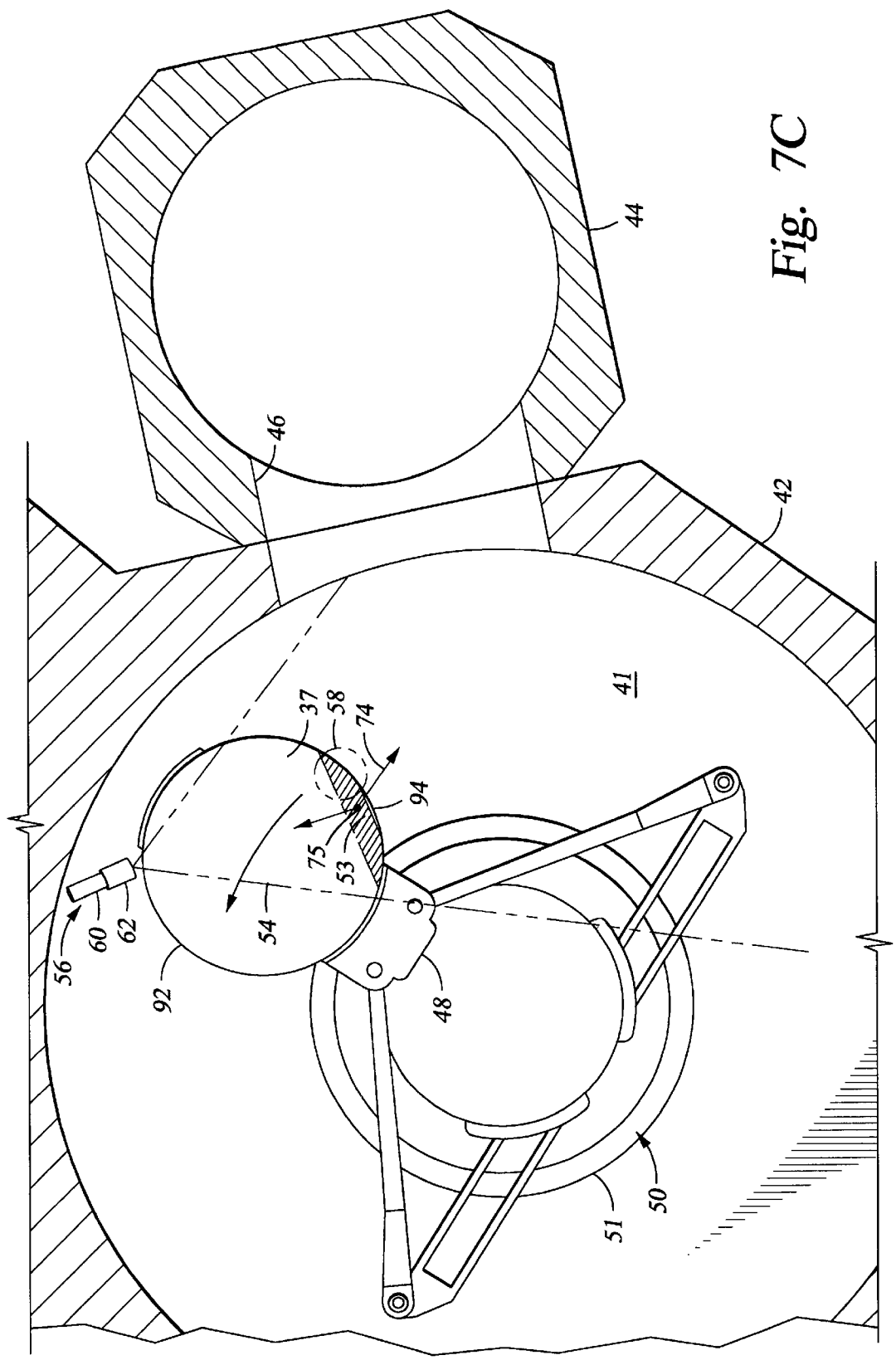

The operation of embodiment shown in FIG. 6 is illustrated by FIGS. 7A–C which are top views of the processing system 100 showing the blade 48 and substrate 37 in various positions during rotation through the transfer chamber 42. FIG. 3A shows the blade 48 immediately after initiating counter-clockwise rotation so that the leading edge 92 of the substrate 37 is positioned in the path of the signal 54. Thus, a portion of the light projection 53, represented by the shaded area, is shown intercepting the leading edge 92 of the substrate 37. During the continued rotation of the blade 48, shown by FIGS. 3B–C, the light projection 53 scans the upper surface of the substrate 37. The light projection 53 illuminates obstruction 75 on the substrate 37 which causes scattering and/or reflection of the signal 54. Although the obstruction 75 may be in the micrometer range it is shown greatly exaggerated for clarity. Obstruction 75 may be a process chamber flake, a surface defect (erosion, dishing, etc.), or an intended device feature. The scattered and/or reflected portion 74 of the signal 54 is then collected by the receiver unit 58. Where the detector 82 is a CCD, the scattered and/or reflected portion 74 is focused by the receiver optics 80, imaged onto the elements of the CCD, converted into an electrical signal and transmitted to the PMC 86 for processing.

It is understood that the foregoing sequence may be performed before and/or after the substrate 37 undergoes a processing cycle in a processing chamber. For example, FIGS. 3A–C may represent a substrate being transferred from a load lock chamber to a processing chamber along process inspection routes 122 and 124. Alternatively, FIGS. 7A–C may represent a processed substrate being transferred to a cooldown chamber or being returned to a load lock 106 after it has been processed.

Figure 8B:
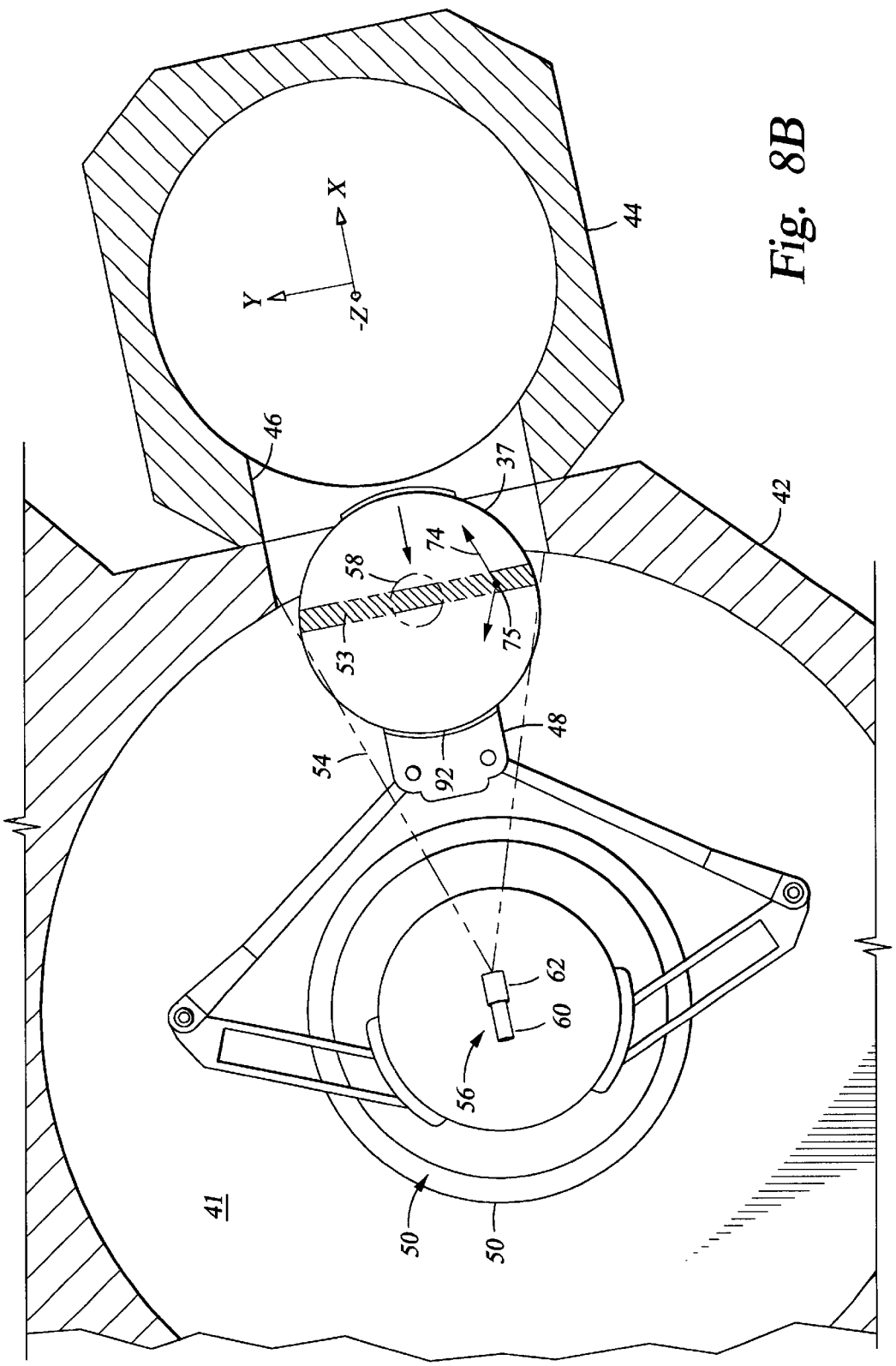
Figure 8C:
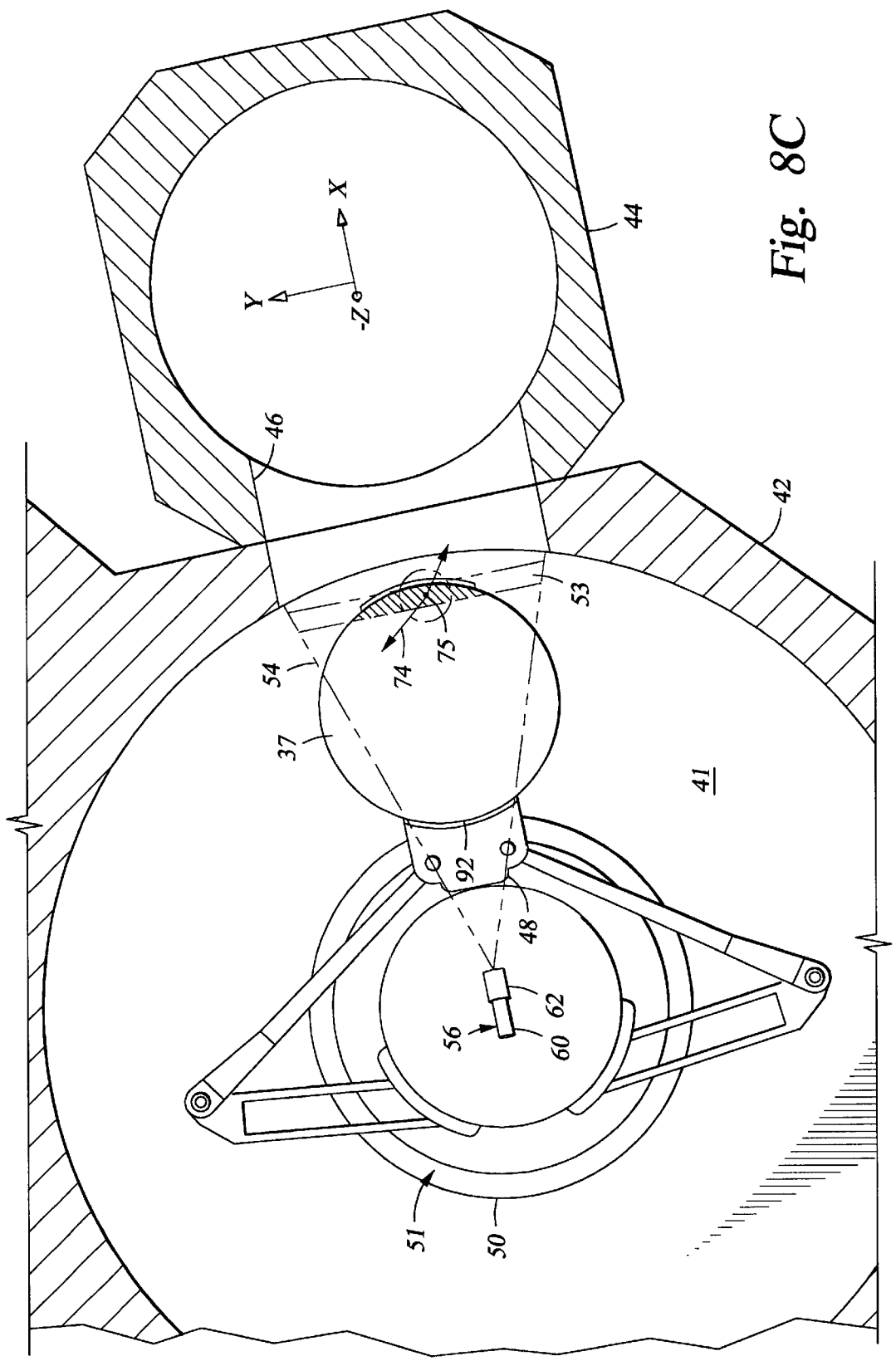

In another embodiment, process inspection is performed during retraction or extension of the robot 50 into or out of a processing chamber or service chamber, or load locks along inspection route 124. FIGS. 8A–C illustrate the operation of such a process inspection embodiment. FIGS. 8A–C are top views of the processing system 100 showing the blade 48 and substrate 37 in various positions during linear movement through the transfer chamber 42 out of chamber 44.

FIGS. 8A–C is a top view of the processing system 100 showing the blade 48 and substrate 37 disposed thereon during the extension of the blade 48 into the chamber 44 from the transfer chamber 42 via the aperture 46. The chamber 44 may be any type chamber such as, for example, a process chamber, a cooldown chamber, a metrology chamber, or a substrate orientation chamber. In FIG. 8A the blade 48 is shown immediately after initiating linear movement from the vacuum chamber 44 to the transfer chamber 42 so that the leading edge 92 of the substrate 37 is positioned in the path of the signal 54. Thus, a portion of the light projection 53, represented by the shaded area, is shown intercepting the leading edge 92 of the substrate 37.

In order to maximize the exposed surface area of the substrate 37, the signal 54 preferably intercepts the substrate 37 as the substrate 37 exits the chamber 42 at the aperture 46. Such a positioning ensures exposure of substantially the entire upper surface of the substrate 37 after full retraction of the blade 48, thereby maximizing the surface area of the substrate 37 which is scanned by the signal 54. During the continued linear movement of the blade 48, shown by FIGS. 8B–C, the light projection 53 scans the upper surface of the substrate 37.

The embodiments shown in FIGS. 4, 7A–C, and 8A–C are merely illustrative. In an alternative embodiment, a pair of transmitter units 56 and receiver units 58 may be used in combination to monitor a substrate during linear motion and rotational motion, respectively. Such an arrangement can improve the accuracy of detection. A person skilled in the art will recognize other embodiments. Further, while a single surface scan of the substrate provides a high degree of accuracy relative to perform the processing monitoring methods of the invention, additional methods may be employed to enhance process monitoring. For example, the robot blade 48 may be dithered, oscillated, or repositioned so that a given obstruction can be moved into the field of view of another CCD detector element in the array of elements or perhaps an auxiliary high resolution camera. Additionally, a multi-mode camera may be used where the focus, field of view, and the like may be changed automatically to enhance the view of the obstruction. Interpolating across multiple detector elements using the robot provides additional resolution for performing various monitoring methods.

Figure 9:
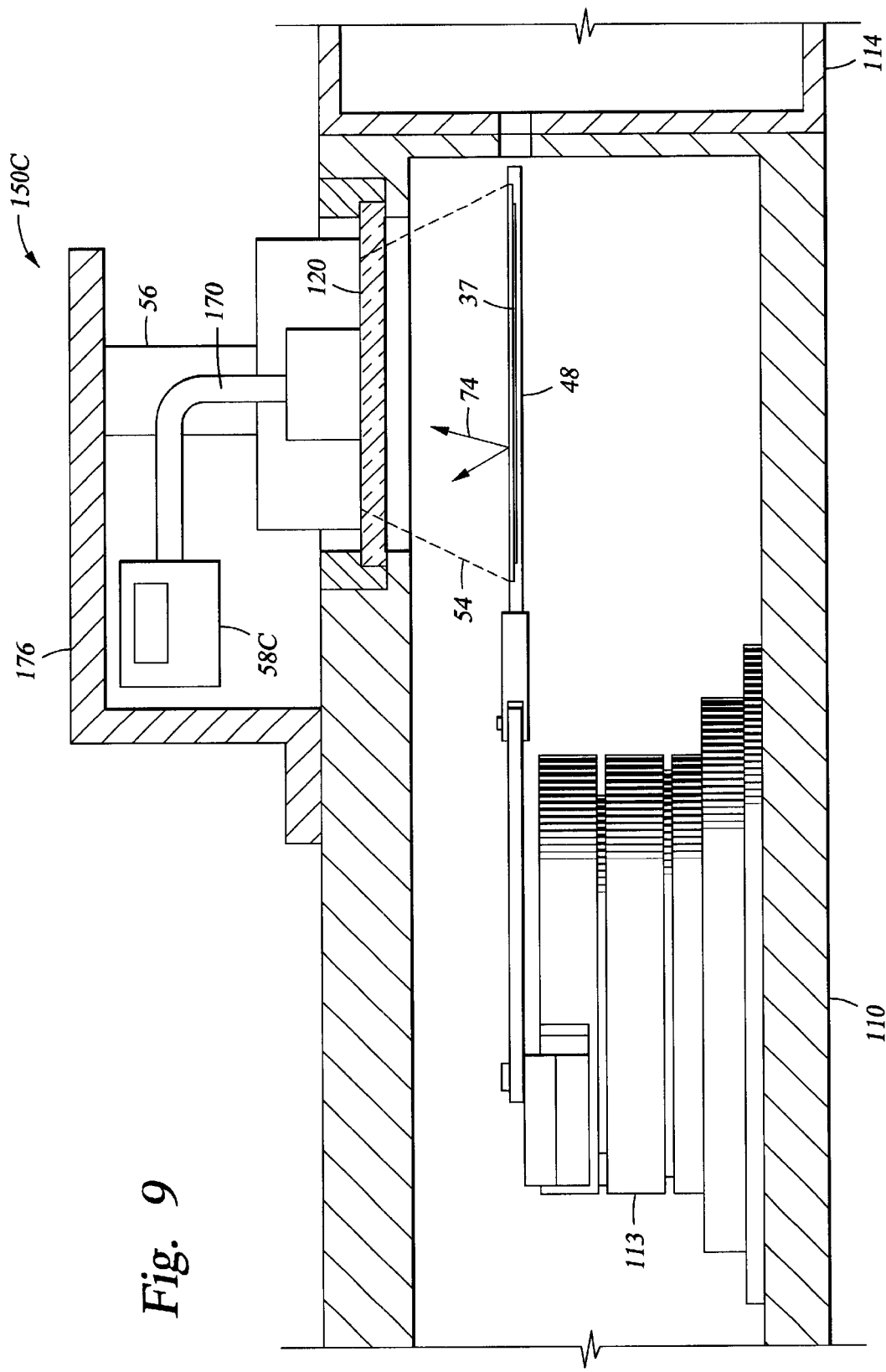
FIG. 9 is a cross sectional view of a chamber and a lid assembly illustrating one embodiment of an optical inspection system.
Figure 10:
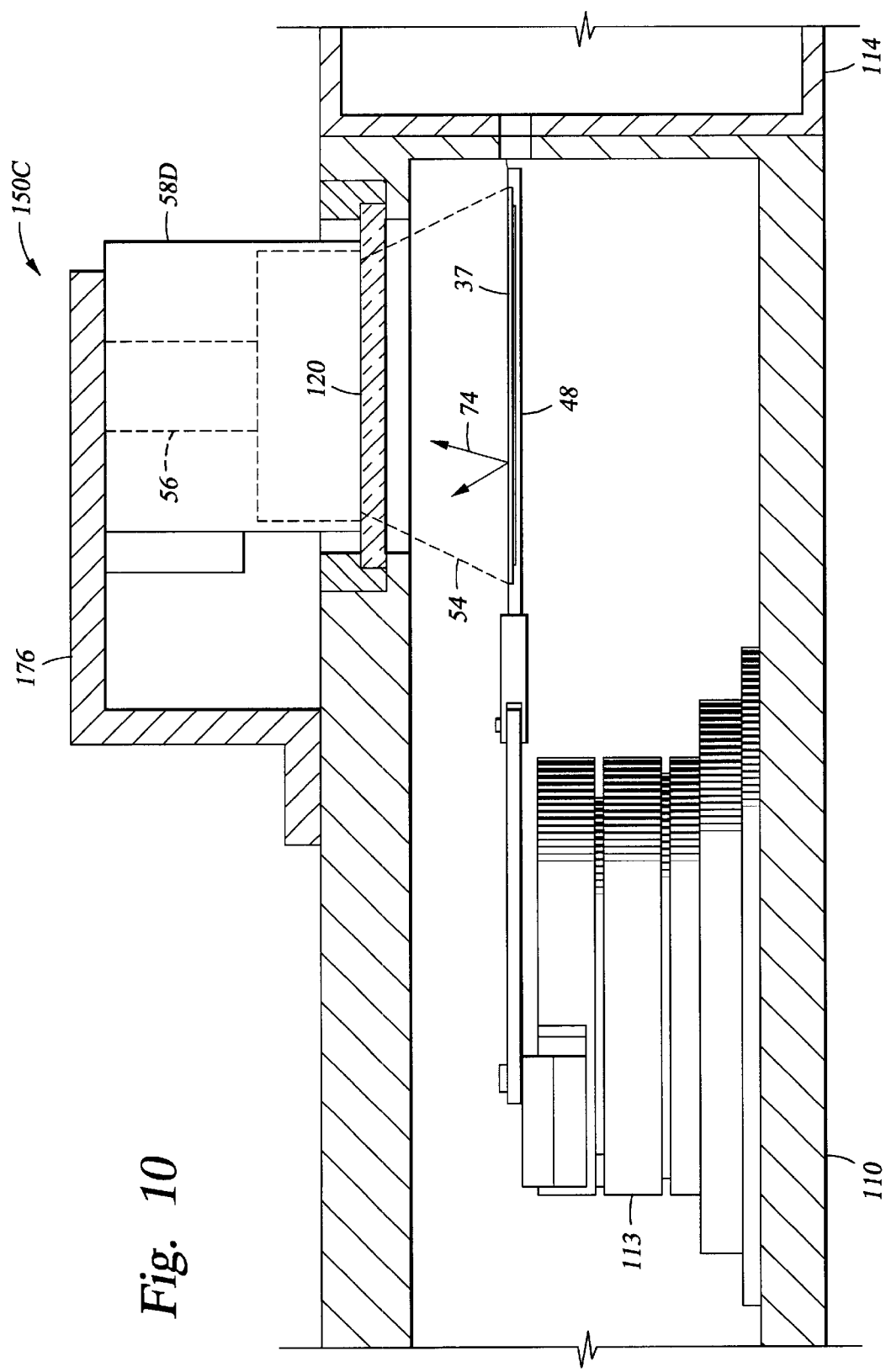
FIG. 10 is a cross sectional view of a chamber and a lid assembly illustrating one embodiment of an optical inspection system.

In another embodiment, the OIS 150 is configured to receive primarily reflected light (as opposed to scattered) in a gray-field configuration from the transfer chamber 110. Embodiments are shown in FIGS. 9 and 10. FIGS. 9 and 10 show a partial cross sectional view of the processing system 100 and, in particular, of a process chamber 114 and the transfer chamber 110. The robot 113 is shown carrying a substrate 37 and positioned adjacent to the entry of the process chamber 114. The receiver unit 58C in FIG. 9 and the transmitter unit 56 are mounted to member 176 and disposed in a view port 120 with a field of view of the substrate 37. In another embodiment, the receiver unit 58D in FIG. 10 and the transmitter unit 56 are mounted to member 176 and disposed in a view port 120 with a field of view of the substrate 37. The receiver units 58C or 58D are preferably any device adapted to receive spectral data.

When the substrate 37 is positioned below the OIS 150C as shown, light emitted from the transmitter unit 56 is reflected and/or scattered from the upper surface of the substrate 37. When the substrate 37 is positioned below the OIS 150D as shown in FIG. 10, light emitted from the transmitter unit 56 is reflected and/or scattered from the upper surface of the substrate 37. In some embodiments, the substrate 37 is scanned with an illumination source 56 in the manner described above. In other cases, all or substantially all of the substrate is illuminated with a broadband flash device or similar apparatus. In any case, the reflected portion is collected by the receiver unit 58C in FIG. 9, or 58D in FIG. 10, and transmitted to the PMC 86 for processing. In particular, the collected information is processed to identify spectral characteristics of the substrate 37. Details of spectral analysis are described below.

In one embodiment, as illustrated by FIG. 9, the receiver unit may be a spectrometer 58C designed to receive incoming energy/signal and output the distribution of spectral components and their intensities to determine the constituents of the energy. The spectrometer 58C is coupled to the view coupled to the view port 66 via an optics assembly 170 comprising a fiber-optic cable and/or Fish-Eye, and/or diffuser lens and other optics to focus, shape, and control the signal to allow the spectrometer 58C to view the substrate 37 as a whole and/or portions thereof.

In another embodiment, as shown in FIG. 10, the receiver unit 58 shown in FIG. 10 comprises an OCR camera 58D. The OCR camera 58D is configured to capture an image of characters located on the upper surface of the substrate 37 for identification purposes. It is contemplated that the characters may include bar codes and other symbolic identification markings. Such a device was described above and a detailed discussion is not needed.

While FIGS. 6, 7A–C, 8A–C, 9, and 10 illustrate embodiments wherein the transmitter unit 56 and receiver unit 58 are disposed on or in the transfer chamber, other embodiments may be used to advantage. In general, the transmitter unit 56 and receiver unit 58 may be positioned at any point on the processing system 100 where the signal 54 may be directed onto the upper surface of a moving, or non-moving, substrate and scattered and/or reflected signals 74 may be detected by the receiver unit 58. Multiple transmitters/receivers can be located throughout the system.

IV. Lid Assembly

FIGS. 11 and 12A–C show a lid assembly 1100 illustrating one embodiment of an OIS 150. The lid 1100 is adapted to be disposed on a (or otherwise be part of) a process chamber or service chamber. The lid assembly 1100 includes various devices and features which operate as parts of an OIS. The lid assembly 1100 generally includes a body defining three ports 1110, 1112, 1114 therein. In one embodiment, a first port 1110 provides line of sight for a receiver unit, or camera 1116, such as a charge coupled device (CCD) for receiving optical inputs from within the chamber. A second and third port 1112 and 1114 are formed within the lid 1100 to enable one or more transmitter units, or light sources 1118, 1120, to be coupled through each of the ports into the chamber and also to provide light traps (i.e., exits for reflected and/or scattered light from the substrate surface) for the light sources 1118 and 1120. In one embodiment, the light sources 1118 and 1120 are a combination fiber optic bundle and light source configured to form a horizontal light-line. The camera 1116 and the light sources 1118, 1120 are each secured to the chamber by mounting brackets 1152, 1153, 1154. In one embodiment, the light sources 1118 and 1120 can be halogen light sources or other light sources capable of operating in the 400 nm to 750 nm range. Each of the ports 1110, 1112, and 1114 has an energy transparent window 1122, 1124, and 1126 disposed therein to provide vacuum isolation within the chamber on which the lid assembly is disposed. In the particular embodiment shown, the lid assembly 1100 also includes optics assemblies 1121 and 1123 disposed between the windows 1124 and 1126 and the light sources 1118 and 1120, respectively. The optics assemblies 1121, 1123 can include any combination of filters, diffusers, lenses and the like.

The lid assembly 1100 mounting the windows 1122, 1124, and 1126 and the CCD or camera 1116 and light sources 1118, 1120 can be made of aluminum or other machineable materials that meets outgassing and porosity requirements of the vacuum environment. Each of the surfaces within the lid assembly 1100 are preferably machined or polished to provide a desired surface reflectivity. One embodiment allows the lid assembly 1100 to made of a metallic material comprising a surface 1130 having the appropriate roughness or polish. In each of the ports for the light sources 1118 and 1120 and the CCD 1116, the surfaces are polished. For example, the surfaces in the CCD port 1110 can be finished to 32RA, the surfaces in the first light source port 1114 can be finished to 16RA and the surfaces in the second light source port 1112 can be finished to 8RA. The surfaces are finished to a surface smoothness which minimizes scattering of secondary light back into the optical environment of the chamber.

The highly reflective surfaces are positioned so that reflected light is effectively directed out of the chamber through windows 1126 and/or 1124.

Figure 12A:
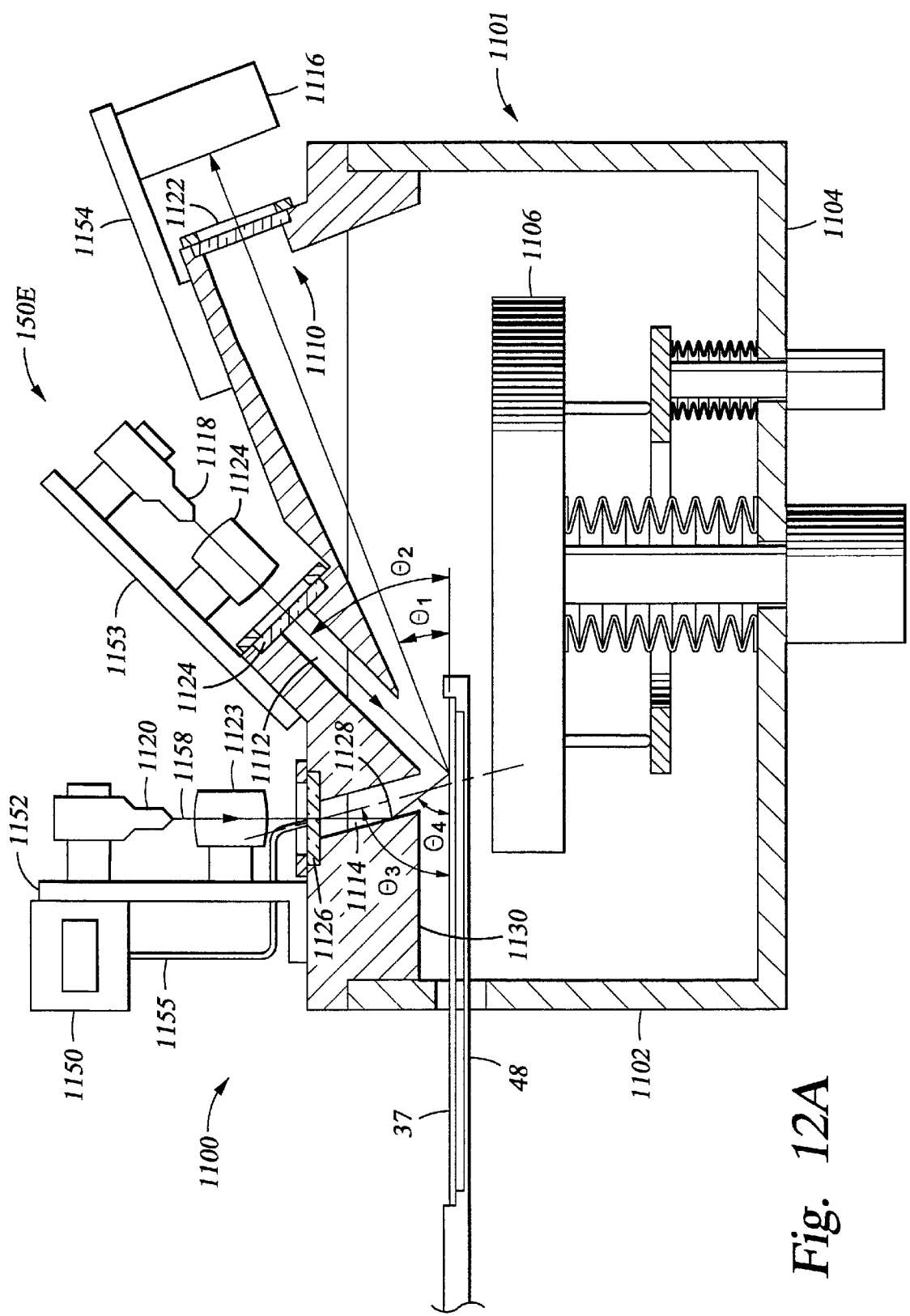
FIGS. 12A–C is a cross sectional view of a chamber and a lid assembly from FIG. 11 showing various positions of a substrate disposed on a blade during linear movement of the blade.
Figure 12B:
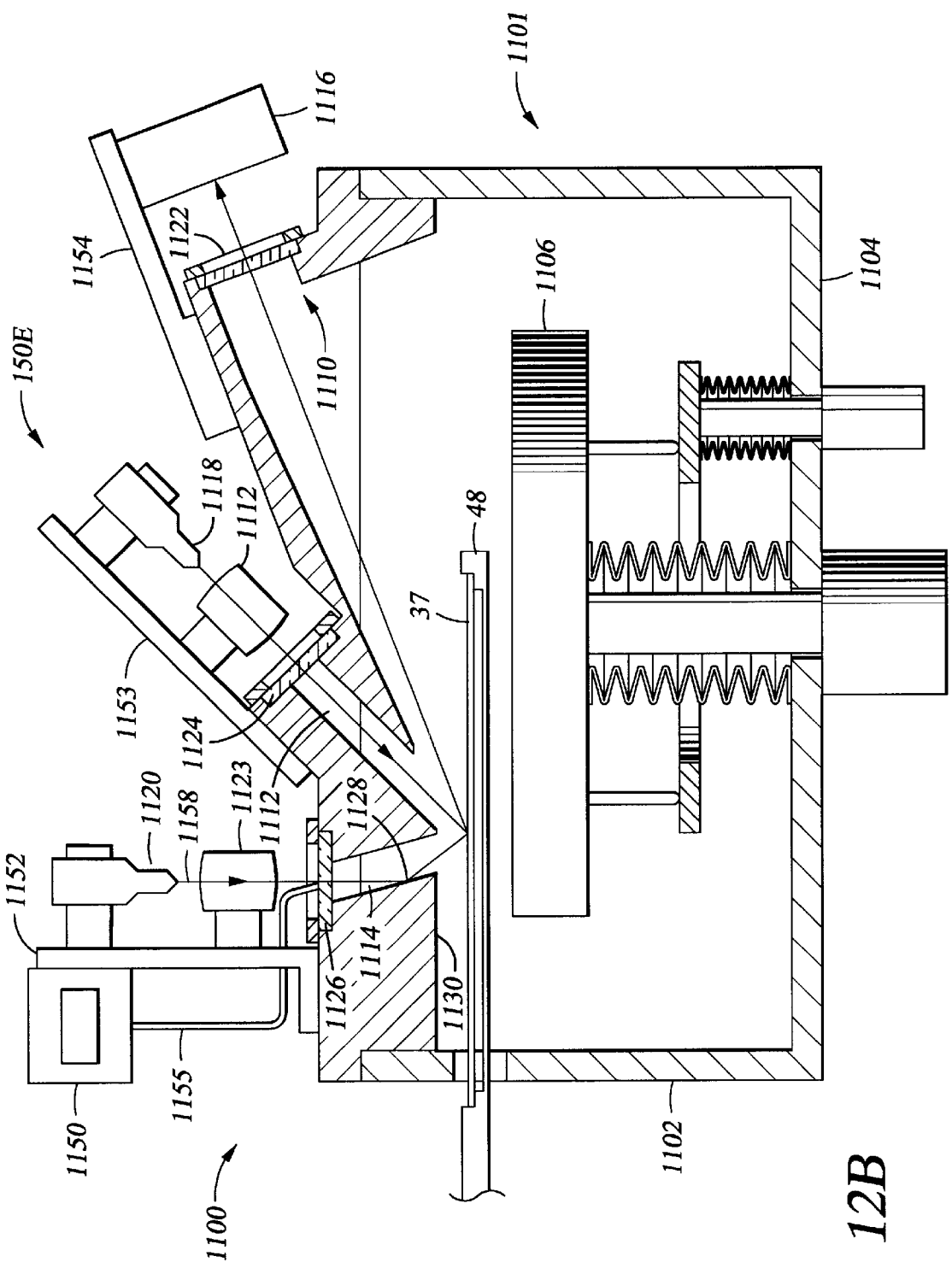
Figure 12C:
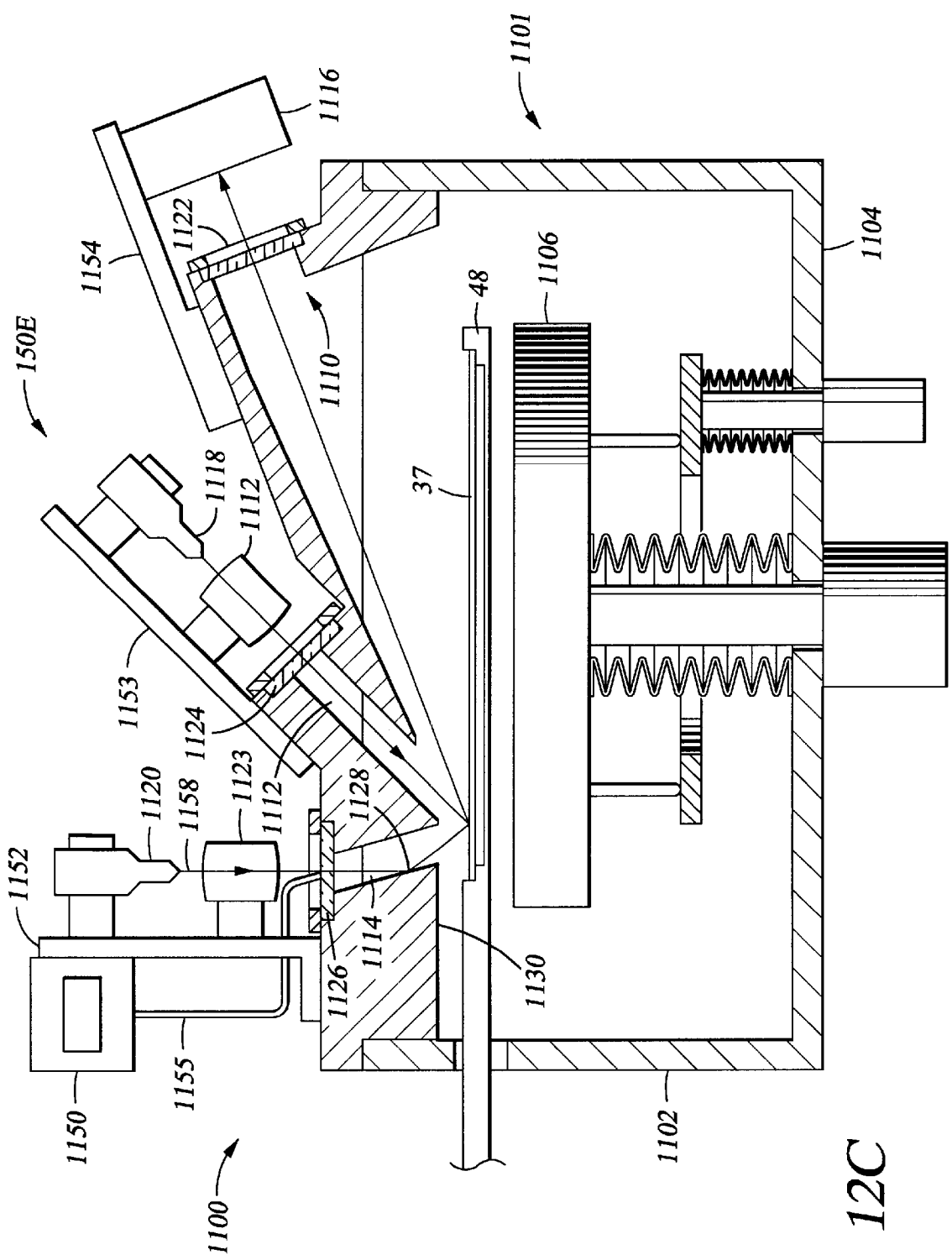

FIGS. 12A–C show a cross-sectional view the lid assembly 1100 located at an upper end of a processing chamber 1101, such as a cooldown chamber. The chamber 1101 generally includes a chamber body having sidewalls 1102 and a bottom 1104. A support member 1106 may be disposed through the bottom of the chamber to receive and support a substrate 37 introduced into the chamber 1101. The support member 1106 may include a cooling system, such as fluid channels and cooling fluid source, to provide substrate cooling for example. The lid assembly 1100 having an OIS 150E mounted thereon is disposed at the upper surface of the chamber walls and forms a seal therewith.

The port 1110 for the CCD 1116 is disposed at a first angle $\theta_1$ relative to a horizontal line in which the substrate 37 would be introduced into the chamber 1101 (i.e., a substrate transfer path). This angle enables the camera 1116 to have a line of sight view to the substrate 37 as the substrate 37 enters the chamber 1101 on a robot blade 48. Each of the ports 1110, 1112, and 1114 for the light sources 1118, 1120 are disposed at an angle such that a first light source 1118 provides front illumination of the substrate and a second light source 1120 provides rear illumination of a substrate 37 that is introduced into the chamber 1101 with respect to the CCD 1116. Front and rear illumination may occur on introduction or retraction from the chamber 1101 simultaneously or separately, e.g., one on introduction, the other on retraction. The port 1112 provided for the first light source 1118 is disposed at a second angle $\theta_2$ off set from the angle $\theta_1$ of the port 1110 and camera 1116. The port 1114 for the second light source 1120 (i.e., the rear illumination light source 1120) is disposed at yet a third angle $\theta_3$ relative to the transfer plane of the substrate and offset from both the first and the second angles $\theta_1$, $\theta_2$. A signal reflecting surface 1128 is disposed on one wall of the port 1114 to enable the second light source 1120 to be disposed at a steeper angle of incidence with respect of the substrate 37 while still providing a required incident of light upon the substrate 37. As shown in FIG. 12A, the angle of incidence of the optical beam emitted by the light source 1120 relative to the substrate 37 is $\theta_4$.

In some embodiments, the orientation of the camera 1116 and the light sources 1118, 1120 may be automatically adjusted (as opposed to manually). For example, although not shown, servos or similar actuators coupled to a control system may be used to move the various components adjust aperture size and focus from a remote location. In one embodiment, two cameras 1116 may be mounted side by side to enhance the view of the substrate and increase the resolution of the image if used in tandem.

Each of the ports 1112 and 1114 for the first and second light sources 1118, 1120 are positioned to act as a light trap for the other light source. That is, the port 1114 for the second light 1120 source acts as a light trap for the light from the first light source 1118 reflected and/or scattered off the substrate surface. Similarly, the port 1112 for the first light source 1118 acts as a light trap for light reflected from the second light source 1120. The polished surface of the lid 1130 adjacent to the light source port 1126 may also act effectively as a light trap by minimizing back scatter, of the light, within the CCD 1116 line of sight. The interior surface of the lid 1130 adjacent to the light source port 1126 may be polishing so as to minimize scatter of light back to the camera on its principal axis.

Each of the ports 1112, 1114, and 1110 for the CCD 1116 and the light sources 1118 and 1120 may also include optical filters such as polarizers, color spectrum filters, and other bandwidth selective mediums. The filters can be positioned on the atmospheric side of the windows 1126, 1122 and 1124 disposed in each of the openings in the ports 1112, 1114, and 1110. The filters may also be disposed within or integral to the windows 1122, 1124, and 1126.

Filters can be used to increase the contrast between a patterned background on the substrate 37 and obstructions on the substrate and minimize degradation of the image by rejecting longer wavelength improperly focused light, or by reducing the specular content of the light and increasing the scattering component. For example, in one embodiment, color spectrum filters can be used to enhance, or select, the images collected energy (i.e., signal energy) associated with obstructions. If material on the substrate, such as photoresist, is blue and obstructions are red, a red spectrum filter could be used on the source and on the camera to minimize the intensity of wavelengths associated with the photoresist and enhance the wavelengths associated with of the obstructions.

Linear polarizing filters can be used to discriminate between the specular and scattering components of the received light. For example, a patterned viewed through two linear polarization filters arranged so that they are 90° with respect to each other provide filtering of principally the scattering component of the light. Changes in the scattering component represent changes in substrate structuring pattern and/or contamination. Filters can be used to enhance optical recognition (i.e., OCR) for multiple purposes. For example, one filter may be used to enhance particle detection while another filter could be used to enhance character recognition, such as substrate identification characters. In one embodiment, light sources 1118, 1120 and the receiver CCD 1116 may comprise a plurality of different filters to provide a different image for multiple substrate scans to enhance process inspection. In another embodiment filters (not shown) are mounted between the CCD 1116 and port 1124 to allow the various filters to be installed independent of the CCD 1116 operation.

As can be seen in FIGS. 12A–C, the first light source 1118 for front illumination is directed at an angle away from the line of sight of the CCD 11 16. The angle of incidence of the light source 1118 on the substrate 37 is determined so that the reflections from the light source 1118 are into the light trap source formed by the port 1114 for the second light source 1120. Consequently, the CCD 1116 only collects the light, which is reflected and/or scattered back by obstructions on the surface of the substrate 37 from the illumination. The remaining reflected light will be absorbed or routed through the light traps 1112 and 1114 or reflected off surface 1130.

The second light source 1120 is disposed to project the light at an angle toward the CCD 1116. By illuminating the substrate 1108 at this angle, rear illumination is provided. As shown in FIGS. 12A–C, the second light source 1120 is disposed at an angle opposite to the direction in which the light source 1120 must be projected. The first light source 1118 impinges upon the inner surface 1128 of the signal port 1114 and is reflected down onto the substrate 37 at a desired angle. Reflective light along the normal projection of the second light source 1120 is reflected into the light trap formed by the first light source port 1112. Light reflected by irregularities on the surface of the substrate 37 maybe reflected along the line of sight of the CCD 1116.

FIGS. 12A–C illustrates both a first and a second light source 1118 and 1120. However, a single light source, i.e., the first light source 1120 or the second light source 1118, may be used to advantage depending upon needs of the specific process and substrate characteristics. For example, a detection of a smooth substrate may require illumination from a single light source. In contrast, a patterned substrate may best be inspected by using two light sources and polarizers. It is believed that embodiments having two light sources may be utilized to advantage by providing a contrast between images generated using both front and rear illumination. Information requiring receipt and interpretation by the detection system will be reflected along the line of sight of the camera or CCD to provide sufficient information to make the determination sufficient to the particular process. Moreover, a scan may be done on the insertion of the substrate 37 into the chamber using one of the light sources 1118 and 1120 and a different scan may be made as the substrate 37 is removed from the chamber 1101, offering two different views of the same substrate 37 for process monitoring purposes.

Taken together, the three positions of the blade 48 extending into the chamber 1101 shown in FIGS. 12A–C illustrate a scanning process whereby the upper surface of the substrate 1108 is scanned. In operation, the optical information collected by the receiver unit 1116 (e.g., OCR camera) is used to analyze characteristics of the substrate 37, such as particles, defects, surface damage, patterns, identifier information (e.g., alphanumeric characters). Methods for processing such information are discussed below.

In another embodiment, the lid assembly 1100 also includes a spectrometer 1150. Thus, FIGS. 12A–C show a spectrometer 1150 mounted adjacent the light source 1120 on mounting member 1152. The spectrometer 1150 is coupled to window 1126 via a fiber optic cable 1155. The fiber optic cable center is disposed off-center, but proximate to the major axis of the reflected light from either light source 1120 and/or 1118. In this configuration, the fiber optic cable 1155 captures large amounts of the broadband light source used to provide for other substrate inspections. In is contemplated that the spectrometer may be located and coupled to any window 1122, 1124, 1126 via a fiber optic cable.

V. Scanner

Figure 13A:
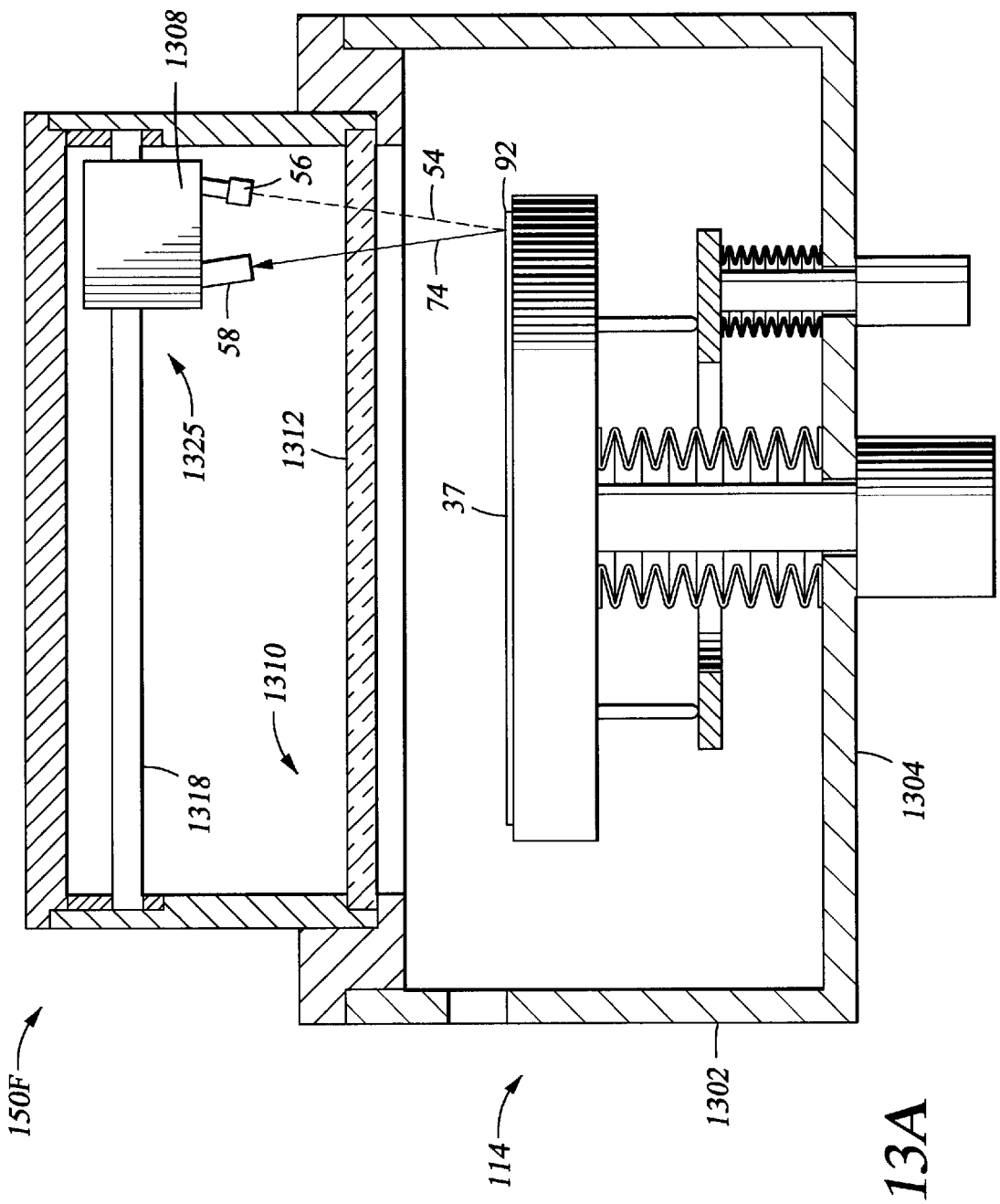
FIGS. 13A–C is a cross sectional view of a chamber and a lid assembly illustrating one embodiment of an optical inspection system showing various positions of a substrate disposed on a blade during a substrate surface scanning sequence.
Figure 13B:
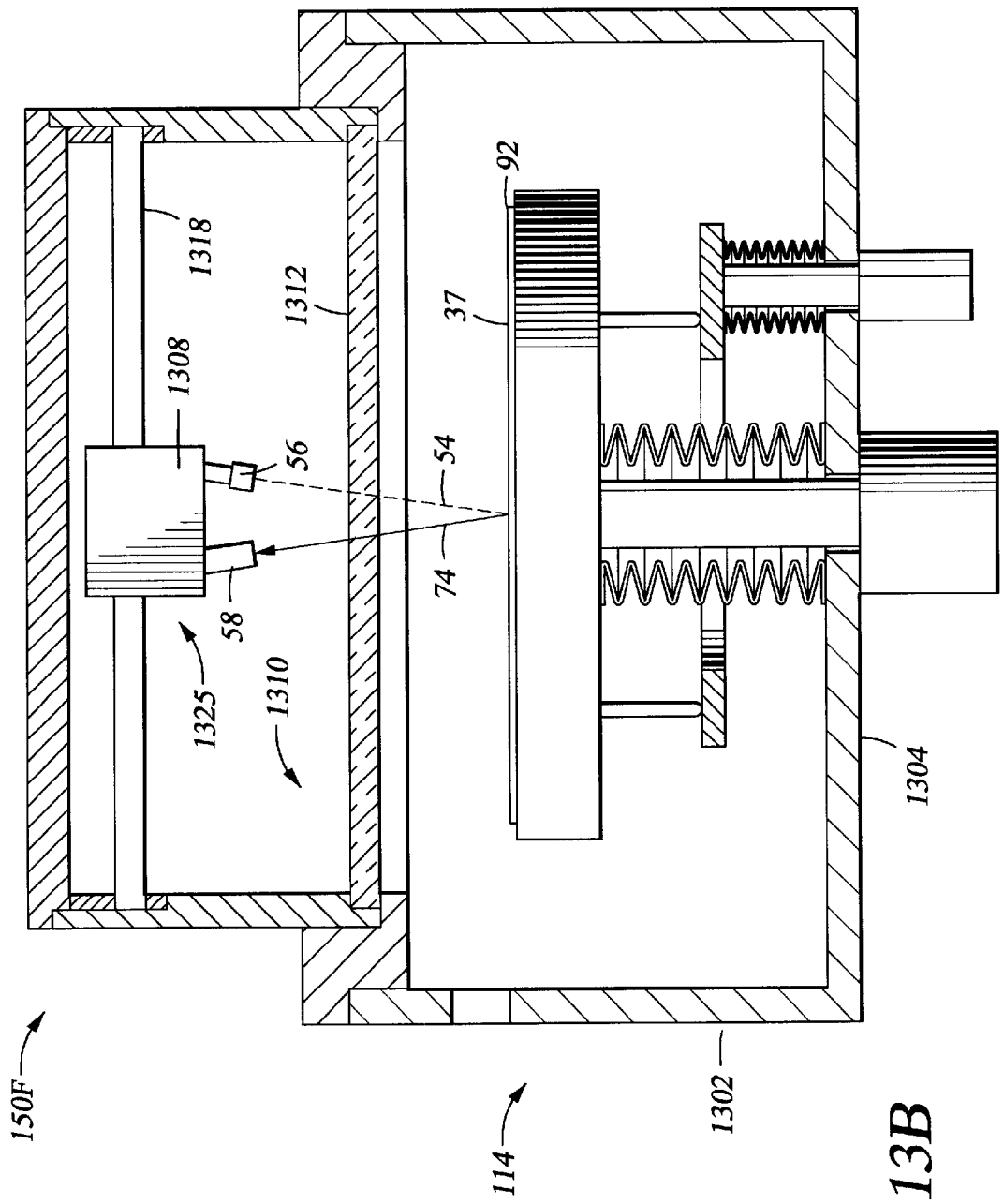
Figure 13C:
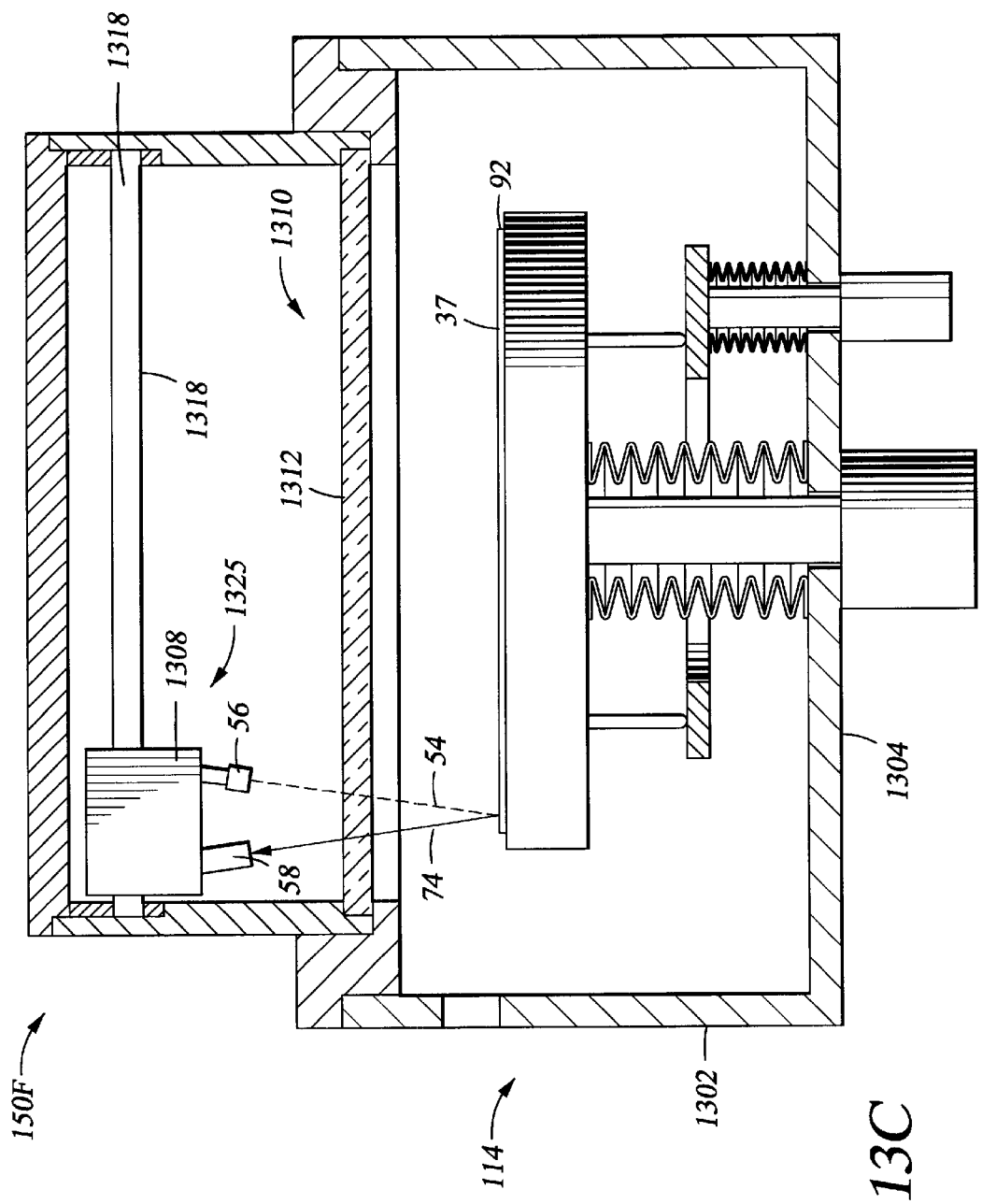

FIGS. 13A–C are cross-sectional views of a lid assembly 1300 illustrating one embodiment of an OIS 150, for a process chamber 114, such as a cooldown chamber. The chamber 114 generally includes a chamber body having sidewalls 1302 and a bottom 1304. A support member 1306 may be disposed through the bottom of the chamber to receive and support a substrate 37 introduced into the chamber 114. The support member 1306 may include a cooling system, such as fluid channels and cooling fluid source, to provide substrate cooling for example.

The OIS 150F, comprising receiver 58, transmitter 56, and connecting member 1308 is provided at the upper surface of the chamber walls and sealably seats thereon. The lid assembly generally includes a body defining a port 1310 therein to provide a line of sight for receiver 58 and transmitter 56. In one embodiment, the port 1310 is sealed with an energy transparent medium 1312 to allow the transmission of signals 54 from transmitter 56.

Receiver 58 and transmitter 56 are coupled to each other through connecting member 1308 forming a scan assembly 1325. Preferably, the transmitter 56 and receiver 58 are angled such that the reflected and/or scattered light 1307 enters receiver 58 to accentuate dark field illumination of light filed illumination. Scan assembly 1325 comprises a motor (not shown) and is adapted to traverse along the length and width of the lid assembly 1300 upon rod assembly 1318. Preferably, the rod assembly 1308 allows the support member 1308 to fully traverse the substrate 37.

FIGS. 13A–C illustrate the operation of a process inspection embodiment. FIGS. 13A–C are side views of the chamber 114 showing the scan assembly 1325 in various positions during movement along the processing chamber 114.

FIG. 13A is a side view of the assembly 1300 showing the support member 1308 and substrate 37 disposed thereon in the processing chamber 114. FIG. 13A shows the scan assembly 1325 immediately after initiating linear movement so that the leading edge 92 of the substrate 37 is within the path of the signal 54.

The processing chamber 114 may be any type chamber such as, for example, a cooldown chamber or a substrate orientation chamber. Further, the OIS 15OF may be located in any location upon tool 100 or in a dedicated inspection/metrology chamber to provide process monitoring.

The scan assembly 1325 continues to move from one side of the chamber 114 to an opposite side. To enhance resolution a series of scan can be performed with the OIS 15OF stepping incrementally to a new region of the substrate. Thus, the signal 54 is moved across substrate 37, thereby exposing the upper surface of the substrate 37 to the signal 54. Substrate obstructions (particles, patterns, dishing, and the like) disposed on the upper surface of the substrate 37 cause the signal 54 to scatter and/or be reflected, shown by arrow 74. The scattered portion 74 of the signal 54 is collected by the receiver unit 58, converted into an electrical signal and transmitted to the PMC 86 for processing. FIGS. 13B–C illustrate the continued linear motion of the scan assembly 1325, illuminated by signal 54 on the upper surface of the substrate 37.

Figure 11:
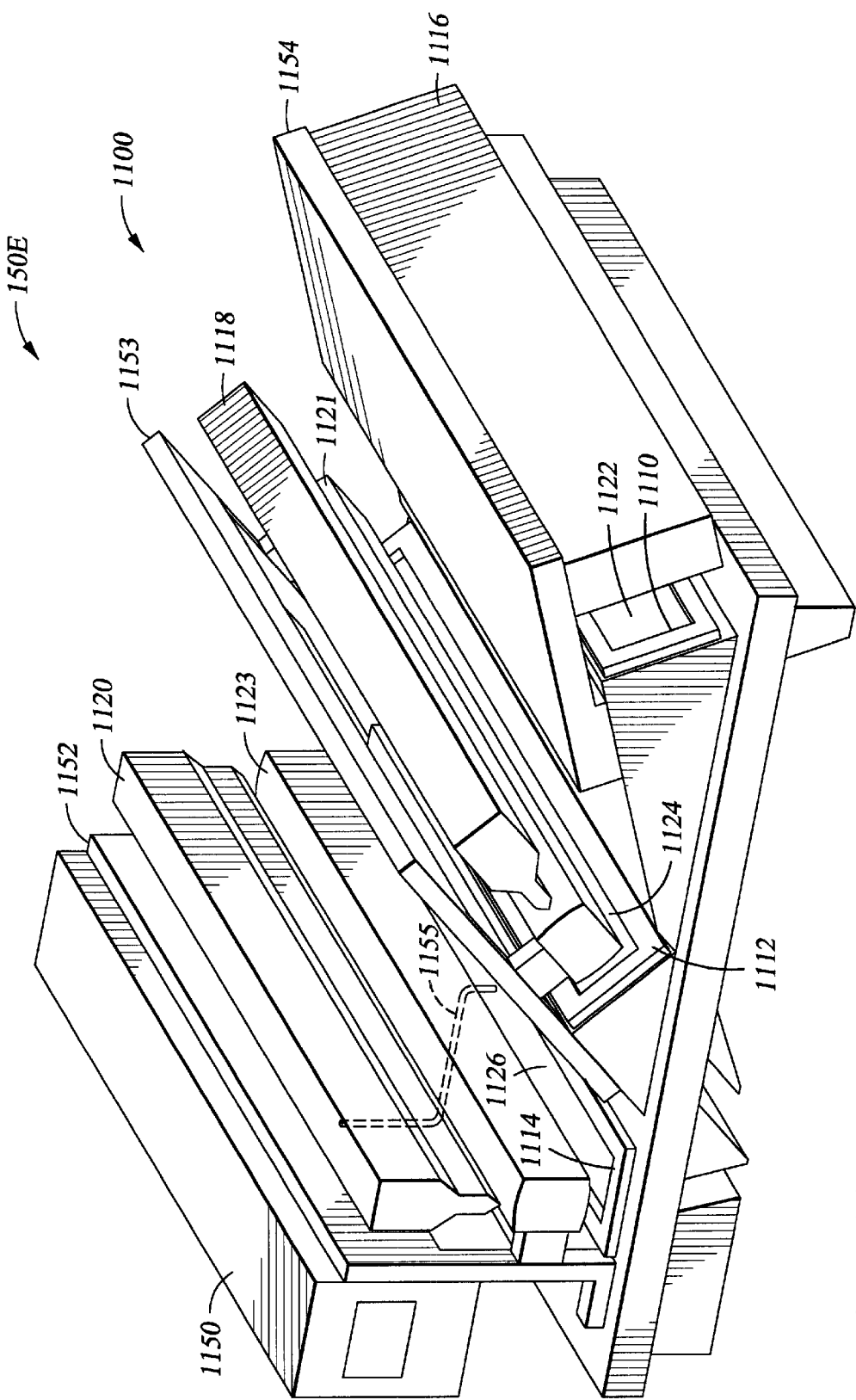
FIG. 11 is a perspective sectional view of a chamber and a lid assembly illustrating one embodiment of an optical inspection system.

While embodiments shown in FIGS. 11 and 13 are described with reference to a process chamber 114, embodiments may also be used in other areas of the tool such as the transfer chamber 110, load lock interfaces and/or factory interface 104. These locations will enable substrates to be inspected both before and after processing without impact to system throughput.

VI. Substrate Alignment and Detection

Determination of the location of a defect on the substrate can be made by identifying particular features on the substrate or blade. For example, in one embodiment the PMC 86 may be programmed to detect the leading edge, i.e., the substrate curvature which first enters the field-of-view of the receiver unit, and lagging edge, i.e., the last curvature to be detected by the receiver unit, during linear or rotational movement of the substrate. The substrate edges provide reference points which may then be used to generate one of two coordinates, i.e., X and Y because the acquisition rate and field of view of the CCD detector elements is known. The acquisition rate refers to the line acquisition frequency of the camera in generating the image during the movement of the substrate in the field-of-view of the CCD detector. Preferably, consecutive images are generated so that no overlapping or missing portion of the substrate results. Thus, the processed output of the CCD detector is a "photograph" of the complete substrate surface. The position of the defect/obstruction may be determined using the detector array of the CCD detector.

Figure 14:
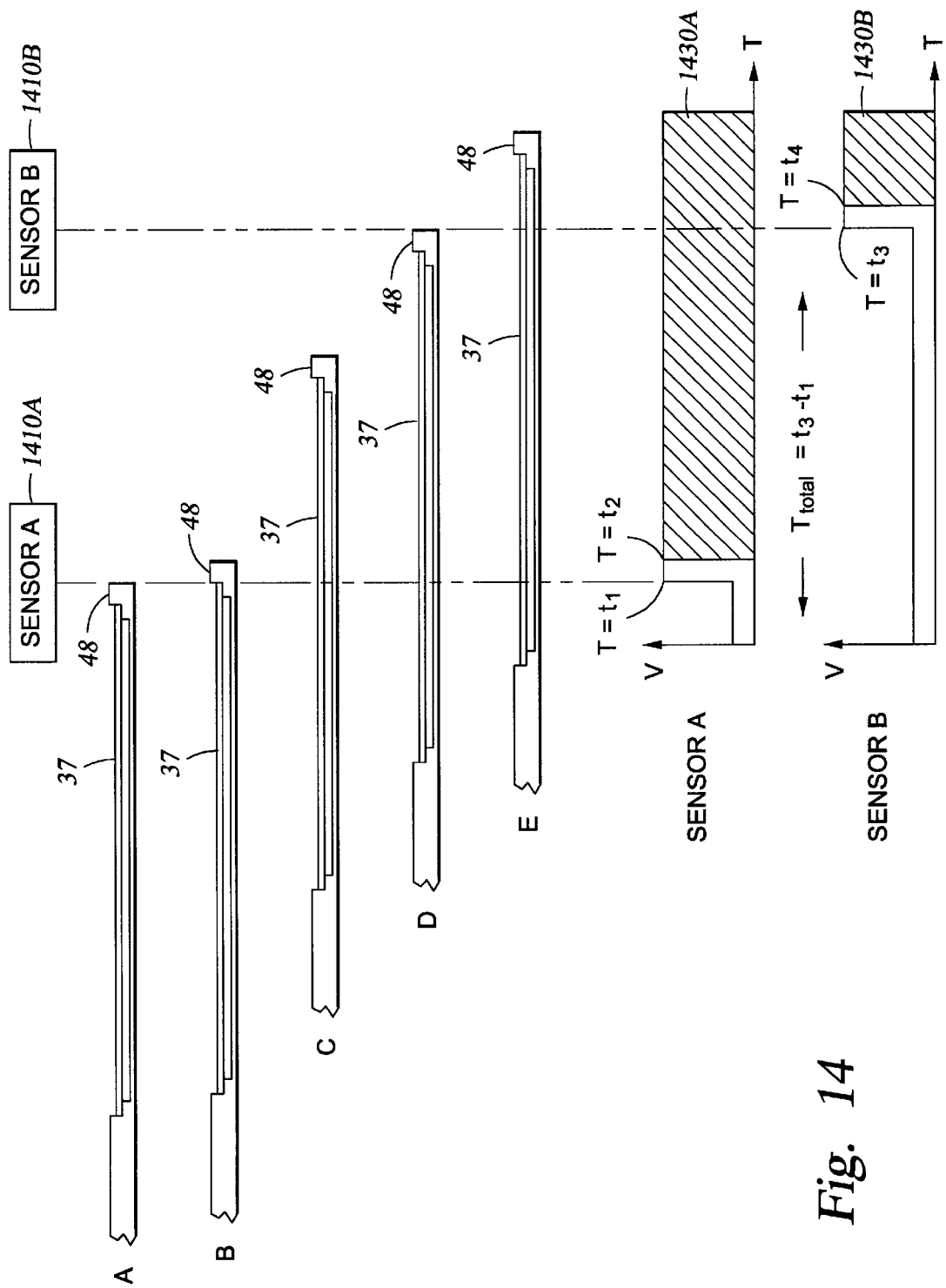
FIG. 14 is one embodiment of a moving view of a substrate detection system for use with the present invention.

FIG. 14 illustrates a substrate detection system 1400 comprising two or more sensors that detect the substrate. In one embodiment, the detection system comprises a first sensor 1410A and a second sensor 1410B. The sensors detect the edge of the blade 48 and the substrate as it moves across the sensors 14010A–B.

Operation of the detector is illustrated by FIG. 14. FIG. 14 shows the substrate 37 supported by a blade 48 and in motion toward sensors 1410A–B. As the substrate is moved into the optical path of the signals of the sensors 1410A–B, the waveform output changes. The resultant change in output may be used to determine the presence, position, and velocity of the substrate. In particular, the detector output is an electrical signal denoting a logic high as a positive detection criteria.

In position A the output signal is low going high at $T=t_1$, to show that substrate has just been detected. The output signal of 1410A is high illustrates a high at $T=t_1$ as the blade is detected by sensor 1410A. Position B illustrates the edge of the blade 48 crossing in front of sensor 1410A, the waveform at $T=t_2$ shows a high. The output for sensor 1410B is low indicating that the blade 48 has not yet been detected by detector 1410B. Position C and E illustrate the edges of the blade 48 moving toward and crossing in front of sensor 1410B. The waveform illustrates that at $T=t_3$ the signal goes high indicating the blade edge has been detected by the sensor 1410B.

At $T=t_2$ and $T=t_4$ the blade has fully crossed the detector and the substrate is being sensed. As the substrate has an uneven reflective surface false triggers may be seen by areas 1430A and 1430B. As $t_1, t_2, t_3$, and $t_4$ the areas 1430A–B are do not care regions. Discrimination of these potentially false signals is accomplished by verification and comparison to timing intervals unique to the blade edge velocity, width, sensor spacing and angles.

The direction of motion of the substrate may be obtained by processing which sensor 1410A or 1410B detected the substrate first. Speed is determined but knowing the distance between the two sensors and dividing by total time.

VII. Conclusion of Apparatus Discussion

The foregoing embodiments provide a detection apparatus and method capable of monitoring substrates on-the-fly and in situ to the processing system. In situ, on-the-fly inspection minimizes the need for conventional stand-alone inspection platforms comprising dedicated actuating mechanisms such as are routinely used in the art. In other embodiments, the inspection is performed while the substrate is stationary, such as in the cooldown chamber. Further, embodiments of the present invention also use to advantage components typically included in any conventional processing system, such as the robot 113 (shown in FIG. 1A), to enable a stageless inspection system. In any case, process monitoring can be performed at various positions in a processing system during normal and necessary operation sequences without transferring the substrates to a separate stand-alone inspection platform, thereby minimizing the impact on throughput. Consequently, each substrate moving through the process system can be inspected, thereby achieving an improvement over prior art systems and processes wherein only periodic sampling was possible due to the negative effect on throughput.

In production, embodiments of the invention provide viable means for determining whether production should be halted and a particular substrate should be examined more carefully for contamination, process related defects or routing errors. Thus, only selected substrates need undergo additional inspection. Substrates may not need further alignment or other positional adjustment if they are verified by the system. Further, the use of conventional features such as transfer chambers and view ports provided therein, process chambers such as cooldown or orientation chambers and transfer robots facilitates retrofitting existing systems with embodiments of the invention without the need for expensive time consuming retrofitting, cleaning and revalidation.

It should be noted that, although the embodiments of the invention facilitate on-the-fly inspection, other embodiments may be used to advantage in dedicated metrology platforms such as the inspection platform 135 (shown in FIG. 1A) described above. In particular, process monitoring methods described below, such as specular and/or scattering and spectral analysis, are not dependent on a specific mechanism and need not be performed on-the-fly.

VIII. Embedded Process Monitoring:

The inventors have discovered that the inspection devices described herein can be adapted to perform numerous inventive uses needed in processing systems, e.g., the determination of selected substrate characteristics including contamination, reflectivity, (specular or scattering) substrate type, discontinuity, orientation and centerfinding, as well as performing calibration of robots and the inspection equipment and monitoring robot behavior. The following discussion provides various embodiments for the present invention but is not intended to be exclusive, as those skilled in the art will readily recognize other possible embodiments.

The present invention also allows for process monitoring and subsequent further evaluation by the inspection system 135. As a substrate is processed each OIS 150 produces spectral signatures, colors, and the like representing the substrate condition/status. In one embodiment, at each process step the PMC 86 monitors the condition using the data obtained from each OIS 150. If a defect is detected in the condition the PMC 86 may make a determination as to whether the substrate should be sent to the inspection platform 135 for further analysis, or request operator intervention to remove the offending substrates within the system or continue on to its next scheduled processing step. In one embodiment, the inspection platform 135 is adapted to perform the identical tests as the OIS 150 but with much higher resolution. It can either inspect the full substrate or focus on specific regions(s). Unless there is a catastrophic process event that causes the process to stop, the metrology unit may examine the suspect substrate while the process continues, thereby avoiding a significant effect on throughput.

The inspection platform 135 is merely representative of one site for further inspection. In general, a system may include any number of inspection sites in addition to the OISs 150. Thus, secondary and even tertiary inspection platforms may be provided in some embodiments.

Accordingly, the invention provides an apparatus and method for generating realtime information about selected characteristics of a substrate. Substrate inspection is preferably performed before and after processing. A preferred operation of the invention may be understood with reference to FIG. 1A. Optical inspection of substrates may be initially accomplished by the OISs 150 located in the Factory Interface 104. Thus, substrates can be analyzed prior to entry into the processing system vacuum environment where process chambers, service chambers are located 110. Upon transfer of a substrate from the transfer chamber 110 into a process chamber 114 or service chamber 116 by the robot 113, embodiments of the invention preferably operate to scan the substrate or otherwise capture an image of a portion, or all, of the substrate. Following processing, the substrates may again be scanned during the retraction of the substrate from the processing or service chamber. Additionally, a determination may be made regarding the process results. For example, the collected substrate image scan may be used to generate information on process uniformity and confirm process endpoint in was achieved.

Accordingly, the substrate can be continually monitored at various stations in the processing system 100. In each instance, the resultant image produces information regarding process uniformity, smoothness, substrate type, orientation, centerfinding, discontinuity/edge defects (structural defects of the substrate due to thermal migration, for example, which may lead to portions of the substrate breaking off), specular and/or scattering signature, presence of particles and other process conditions. In one embodiment, the OIS 150 and PMC 86 operate to generate a map (e.g., two-dimensional or three-dimensional) of the substrate topology. The map can then be analyzed for texture characteristics such as planarity, uniformity and thickness. In addition, any substrate damage or defect, such as chips or fractures may be detected and mapped. Analysis can be enhanced by use of a color CCD detector and/or spectrometer.

Another substrate characteristic which may be determined, is the optical surface characteristics of the substrate. Information regarding optical surface characteristics can be used to determine whether certain process conditions have been successfully achieved, such as the endpoint of an etch process. Because the endpoint information is available in near real-time, i.e., substantially contemporaneously with the end of the process, and proximate the processing chamber, an under-processed substrate may be immediately returned for additional processing. Conventionally, substrates are taken to a remote location for endpoint examination. A subsequent determination that a substrate is under-processed typically results in the substrate being discarded because the time involved in returning the substrate for additional processing and possible growth of a native oxide is cost prohibitive. Furthermore, processing time is often extended to avoid potentially under processing substrates thereby reducing potential system throughput Thus, the invention provides near real-time pre- and post-processing information regarding characteristics of a substrate during a process. Because the information is near real-time an immediate cost efficient decision can be made about how to handle the defective substrates. Further, because each substrate is inspected nearly immediately after processing in the system, as opposed to selected substrates from a batch, the information can be used to quickly rectify identified problems with our further compromising additional substrates and the processing environment. Thus, the process monitoring is nearly real time allowing the process recipe to be optimized and kept very close to the process tolerances thereby increasing the throughput.

Accordingly, the apparatus acts as a processing system "gate-keeper" which make continual first level assignments for substrate and system characteristics. In the event that acceptance criteria are not met, additional analysis can be performed by the inspection platform 135 or similar inspection platform. Such a system increases the opportunities for identifying a broad spectrum of process and handling routing defects in situ without any adverse effect on throughput.

A. Specular Analysis

In one embodiment, specular and/or scattering information is utilized to analyze characteristics of substrates. Such embodiments have particular applicability with patterned substrates which include topography variances that can cause scattering of incident light. Where patterned substrates are to be examined, the invention utilizes the unique intensity distribution of the signature produced by illuminating the substrate. The unique signature is the result of the patterns/structures formed on the substrate. Because the topography due to patterns on substrates that undergo a particular process is substantially repetitive, the signature will be at about consistent for each of the substrates processed yet different from other substrates processed. Thus, the unique signature may be stored in memory and used to compare surface conditions of substrates during production. Additionally, an average signature of the last "n" processed substrates, where n is an integer greater than 1, may be used as a dynamic reference (or calibration) substrate.

Figure 15:
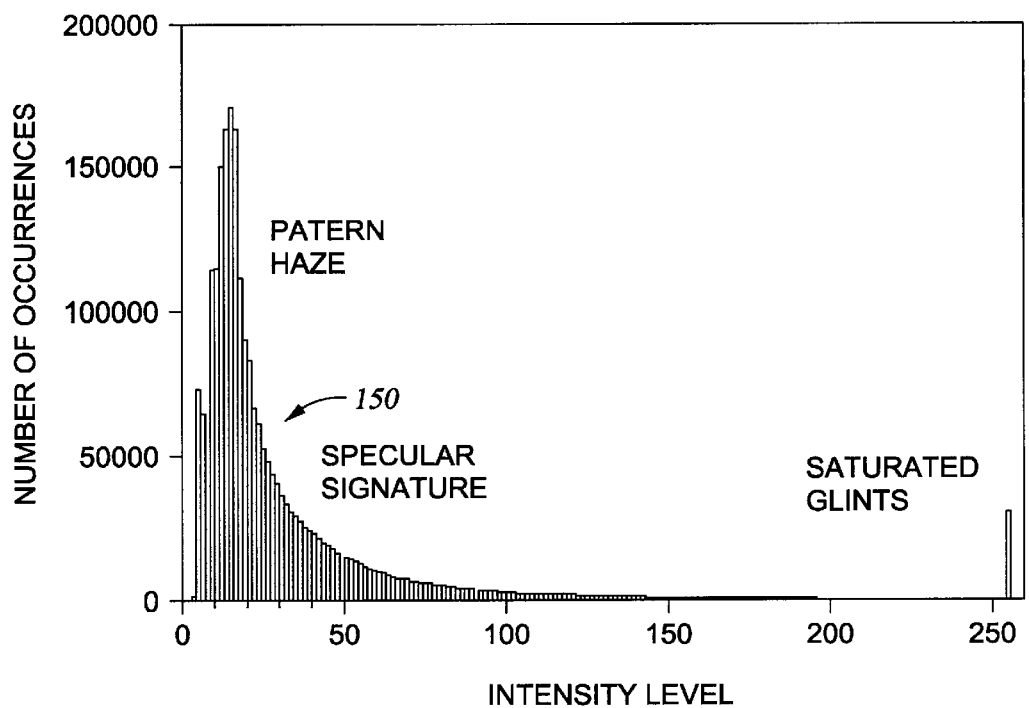
FIG. 15 is a graphical representation of specular intensity distribution of reflections from a patterned substrate illuminated by a light source.
Figure 16:
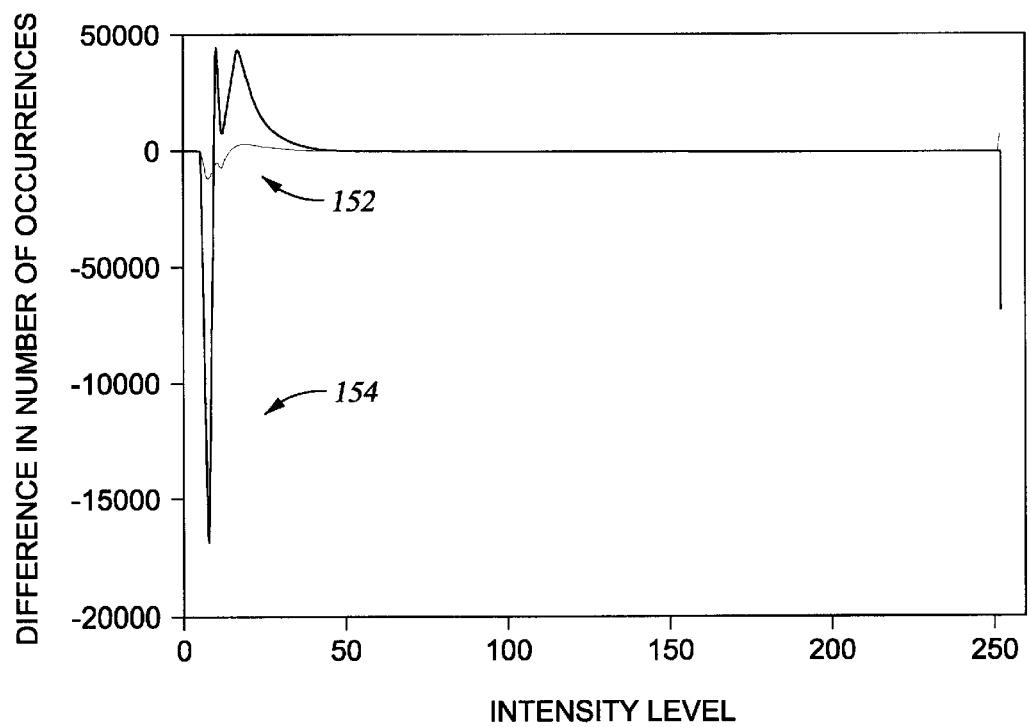
FIG. 16 is a comparative graphical representation of specular intensity distribution on patterned substrates.

FIG. 15 represents a substrate image scan of 3 million data points showing a specular and/or scattering signature 150 for a calibration substrate scanned according to the techniques described above. The number of occurrences (y-axis), or readings by the detection equipment, at a particular intensity (x-axis) level are plotted. Subsequently, two different test substrates were scanned in a similar manner resulting in two separate and distinct specular signatures. To determine the relative conditions of the surfaces of the substrates, the signatures for the two test substrates were compared to the signature 150 for the calibration substrate signatures 150. The graphs 152, 154 shown in FIG. 16 are the result of subtracting the number of occurrences at a given intensity or the calibration substrate from the number of occurrences at the same given intensity for the two test substrates. Thus, a first graph 152 represents the difference in the recorded intensity output of the detection equipment between the first test substrate and the calibration substrate and shows little variation. A second graph 154 represents the difference in the recorded output of the detection equipment between the second test substrate and the calibration substrate and shows a significant variation, indicating a difference in the surface conditions of the compared substrates.

Specular and/or scattering information can be collected, for example, using the above-described embodiments equipped with a line camera (e.g. the CCD 1116 shown in FIGS. 11 and 12A–C). In such embodiments, the line camera positioned so that it collects light scattered from the substrate. In the case of a CCD camera, the camera's CCD detector consists of, for example, 4096 pixel elements oriented in a linear array. These elements serve to provide light intensity values in the x-axis. Values for the y-axis are generated by collecting a succession of data sets (x values), while the robot moves the substrate into (or out of) the cooldown chamber. Each pixel value in the data set ranges from 0 to 255 units and represents the intensity level of the collected light for a specific portion of the substrate. In this case this scanning process results in a data array that exceeds 16.5 million intensity values for each substrate. Among other things, data array can be used for particle detection and process conformance verification using specular and/or scattering signature analysis.

Figure 17:
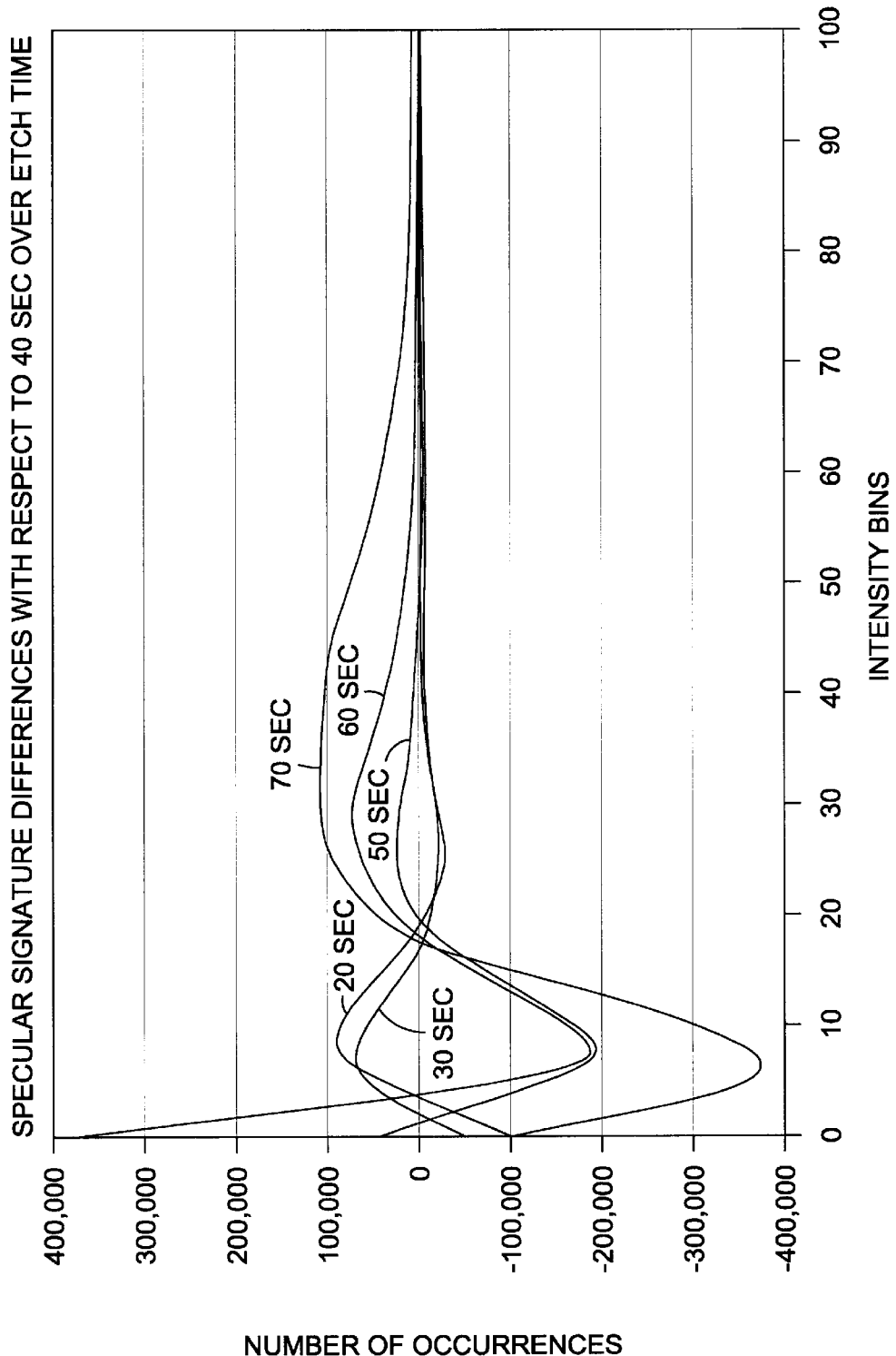
FIG. 17 is a plot showing specular signature differences with respect to a 40 second over etch time.

In one embodiment, the number of occurrences of the 0 to 255 intensity values can be expressed in an intensity distribution histogram. These intensity distribution histograms are directly associated with the structures on the substrate's surface, so they can be thought of as a unique specular and/or scattering signature of a substrate type that has been processed in a specific way. Given the amount of data involved, even subtle changes on the substrate's surface can cause substantial changes to the specular and/or scattering signature. These changes can be plotted to show the differences between specular and/or scattering signatures with respect to same reference. The reference signature which is subtracted from the other signatures should represent the ideal/desired processing target. In the event that a certain failure mode is known to exist for a specific process that signature can be used as a reference. The resulting difference plots represents changes in the structure on the substrates surface. FIG. 17 contains a series of over etch specular and/or scattering signature differences with respect to a nominal over etch time of 40 seconds.

Figure 18:
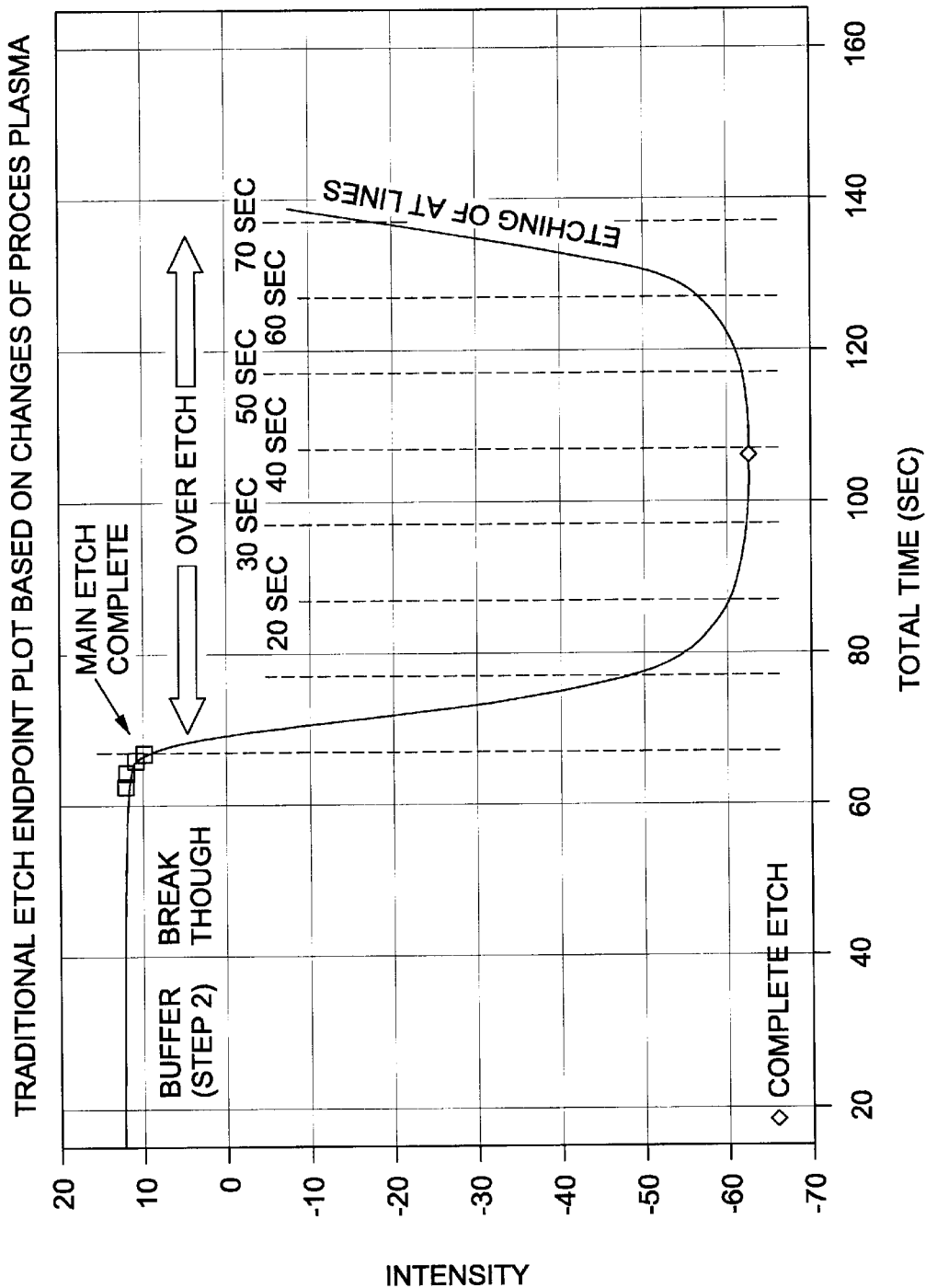
FIG. 18 is a etch endpoint plot based on changes in process plasma intensity.

For clarity, the first 100 out of the 255 intensity bins/ranges are shown. As indicated in FIG. 17, the changes in the specular and/or scattering signatures are substantial and due to different processing conditions. For example, at intensity bins below 18, etch times under the nominal 40 seconds exhibit about 260,000 more occurrences than the etch times above 40 seconds. While at intensity bins above 18, etch times under the nominal 40 seconds exhibit hundreds of thousands of occurrences less than the etch times above 40 seconds. These signature changes are the result of features/structures changing on the substrate as a result of processing in other words. Below 40 seconds, the structures have not fully emerged and above 40 seconds the etch process is attacking the photoresist and the aluminum lines. For clarity, FIG. 18 represents a conventional endpoint plot with the over etch intervals marked.

Figure 19:
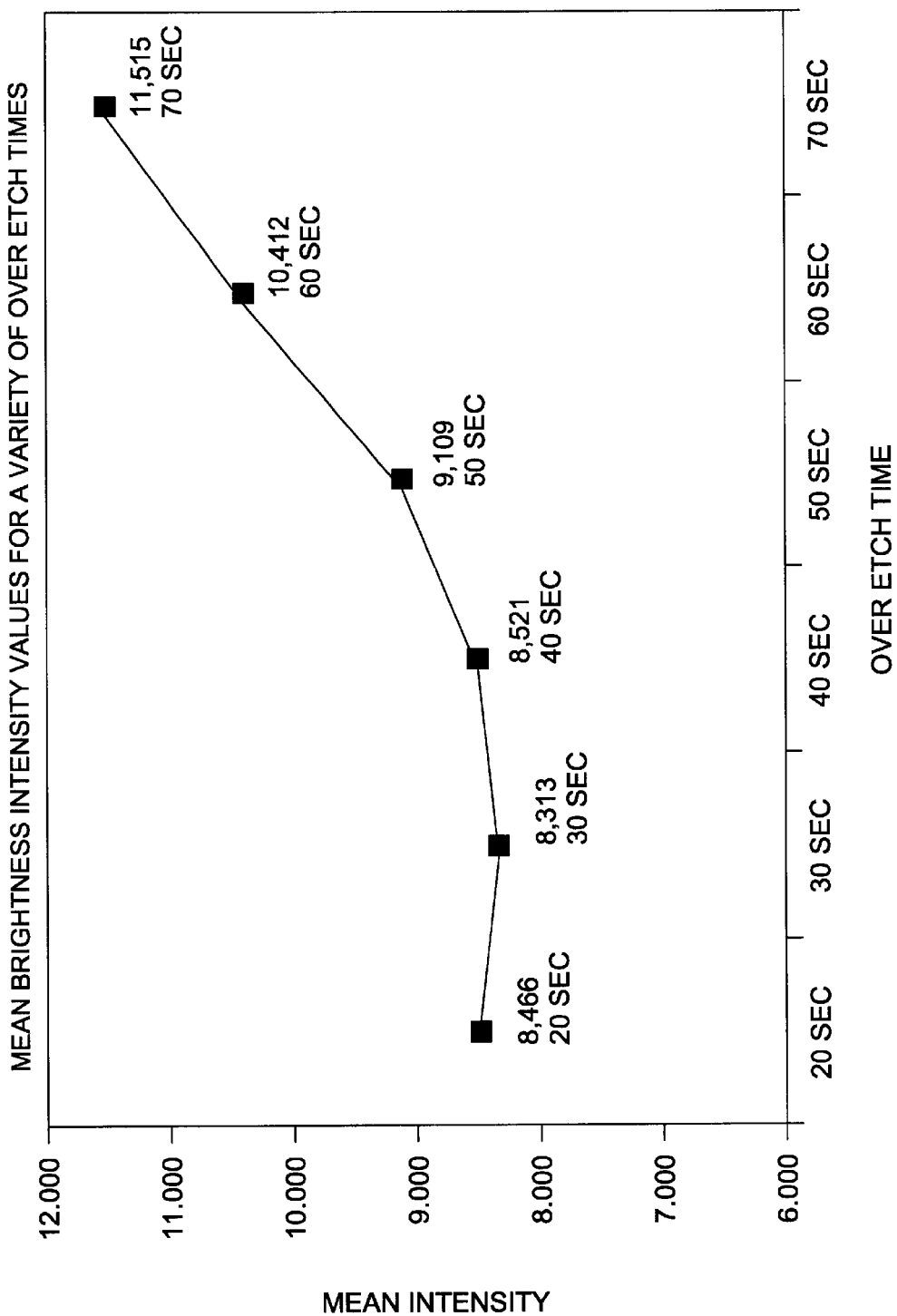
FIG. 19 is a plot illustrating changes in mean intensity values for various over etch times.

The specular and/or scattering signature approach can be expressed as mean brightness values (FIG. 19) to simplify the display provided to the user. The system operator would observe a succession of mean values as the system processes the substrates. Warning and alarm regions would be marked providing the user with quick feedback on process integrity.

Figure 20:
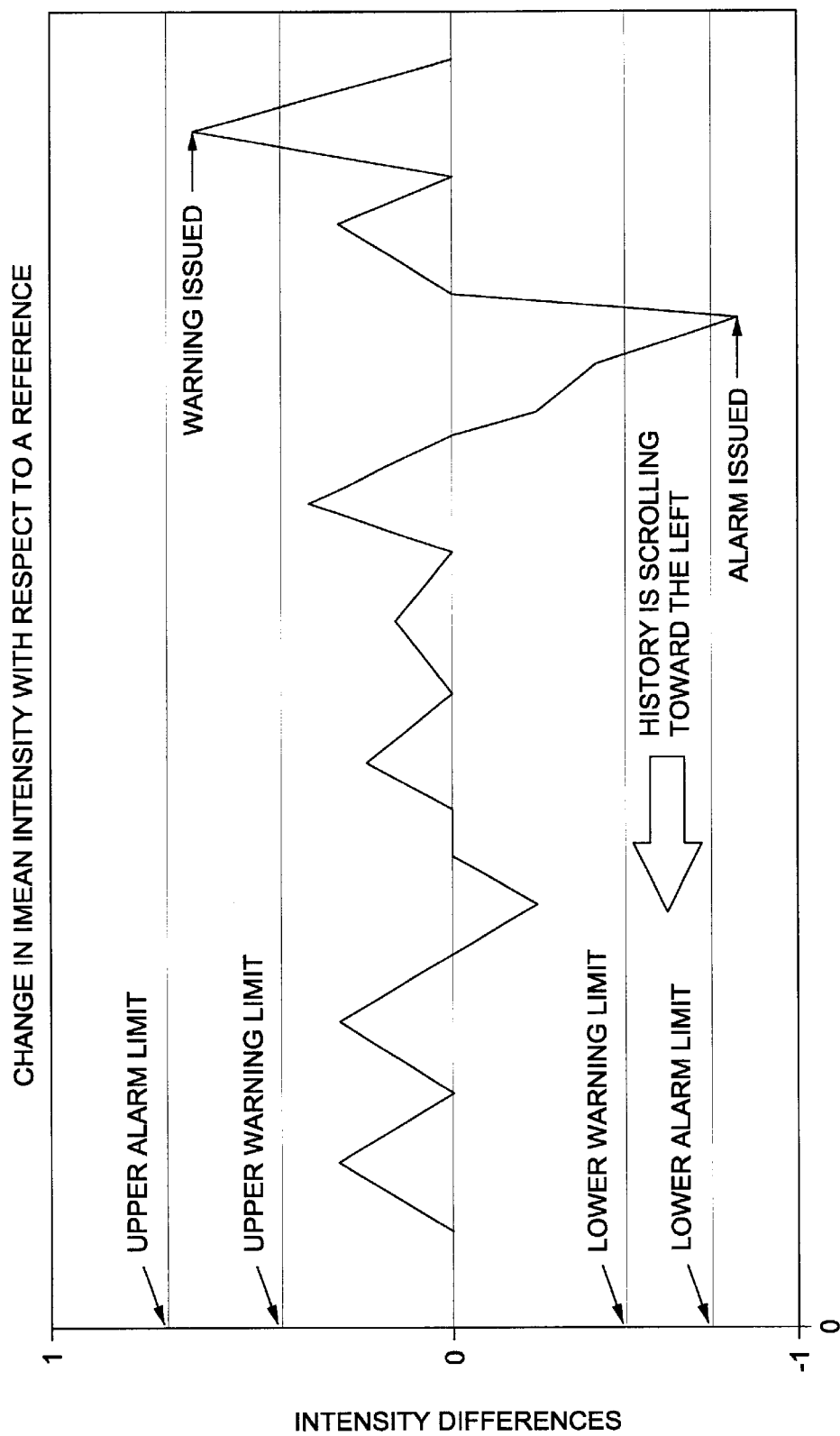
FIG. 20 is a plot illustrating delta-mean intensity values for a succession of inspected substrates.

FIG. 20 illustrates the mean intensity values of substrates calculated as a delta-mean for a reference specular and/or scattering signature. The delta-mean value represents the average weighted mean brightness value associated with the intensity distribution of a substrate with respect to a reference mean brightness values. FIG. 20 represents a succession of delta-mean values for substrates with respect to a reference substrate mean value. As mentioned above, warning and alarm control limits would be marked providing the user with quick feedback on process integrity.

Figure 21:
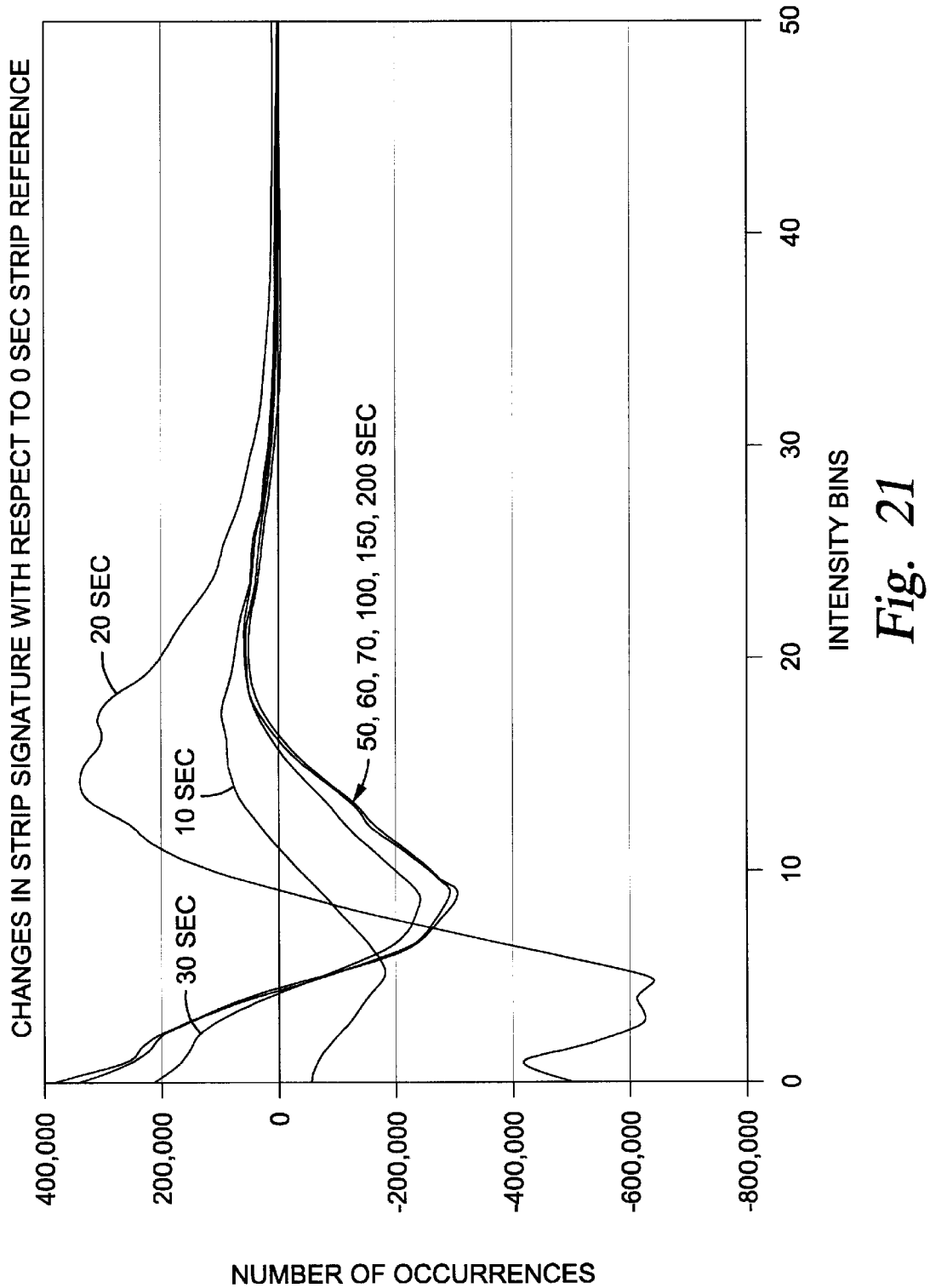
FIG. 21 is a plot showing changes in etch photo resist strip time specular signatures.

Although this discussion has focused on specular and/or scattering signatures from etch processing, which already has a runtime endpoint system, embodiments of the invention are equally applicable to monitoring other process steps involving changes to structures on the substrate. For example, FIG. 21 reflects changes in specular and/or scattering signatures as strip time is increased.

EXAMPLE

Substrates were processed on a Centura system equipped with a DPS Metal Etch Chamber and an ASP strip/passivation chamber, both available from Applied Materials, Inc., located in Santa Clara, Calif. After etch and strip processing, this hot substrate is cooled to near room temperature in a cooldown chamber which includes an apparatus system according to an embodiment of the invention.

Processed substrates consisted of EPIC-generated substrates, utilizing Applied Materials equipment for all steps except for lithography. The photoresist/metal stack on the substrates was: 8000 A DUV photoresist/250 A TiN ARC/5500 A Al—Cu0.5%/250 A TiN/200 A Ti/3000 A thermal oxide. A dense pattern covered about 50% of the substrate, consisting of 0.25 μm lines/spaces.

All substrates were etched using a typical recipe. This etched the metal stack entirely, leaving approximately 5200 A of photoresist on most patterned features (3700 A at the shoulder of patterned lines).

As chip geometries shrink, a greater diversity is observed between the thin Metal 1 stack and the (especially on logic) highest level of metal. Communication chips are the most extreme, with 4000 A aluminum Metal 1 and a sometimes 4 um thick aluminum top metal. The capability of ASP chambers thus must match all metal stacks, while yield becomes more sensitive to corrosion and photoresist remaining on substrates.

An ASP recipe was employed for the purposes of this experiment. This recipe consisted of only one process step flowing only $H_2O$ at lower pressures than typically used in the ASP chamber. The new recipe: One step of 250 C temperature, 0.5 Torr pressure, 750 sccm H2O flow, 1400 W microwave power, variable time as specified in matrix.

Figure 22:
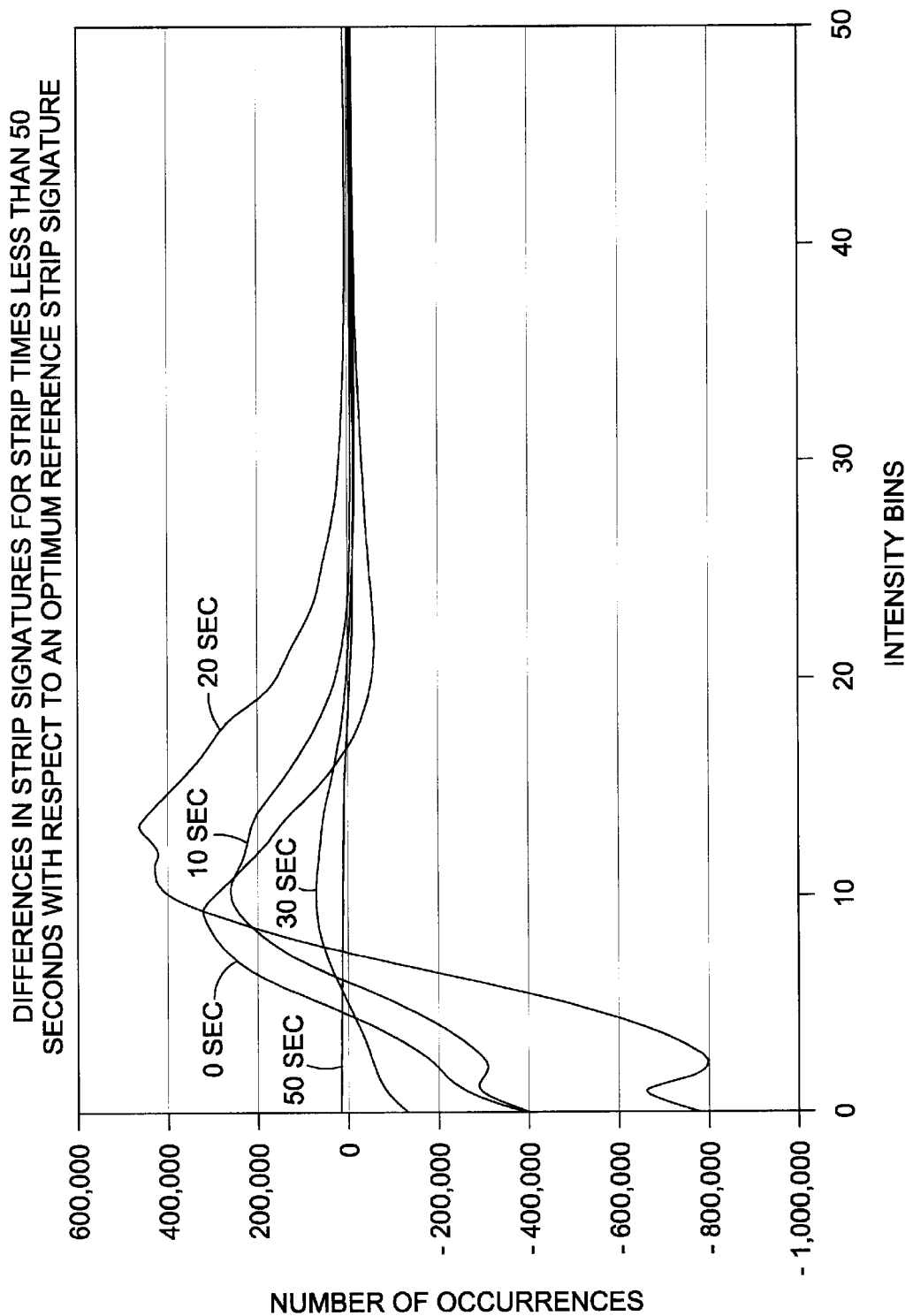
FIG. 22 is a plot illustrating intensity plots for strip times with respect to a reference substrate.
Figure 23:
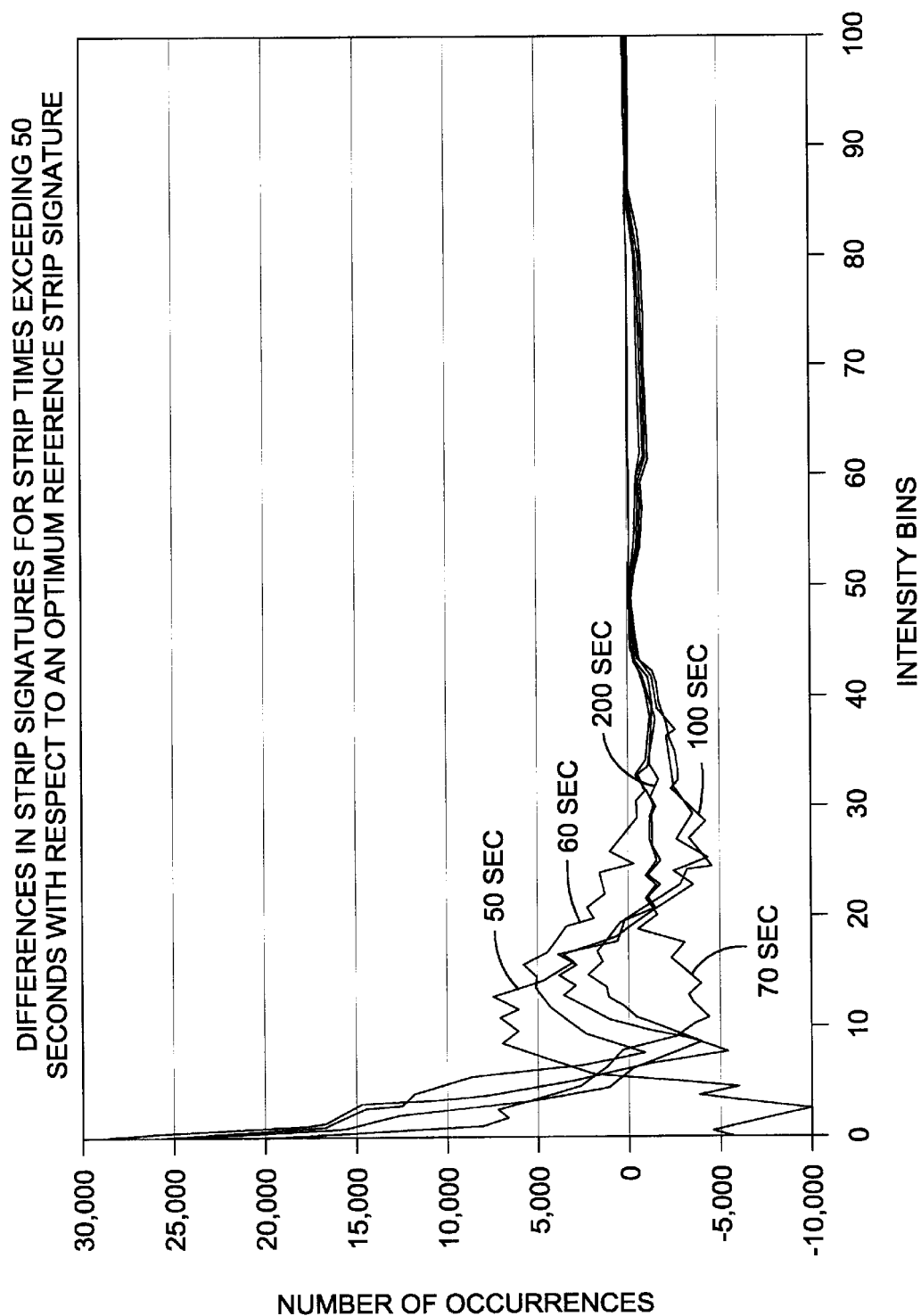
FIG. 23 is a plot illustrating intensity scans for strip times after photo resist has been removed.

Etched substrates were run measured with an embodiment of the invention various ASP processing times: 0, 10, 20, 26, 40, 50 seconds and longer up to 200 seconds. FIG. 22 shows that the intensity scans change for the various times up to 50 seconds of ASP processing. Since strip times longer than 40 seconds look the same as 40–50 seconds on the FIG. 22 scale, these are re-plotted to another graph, FIG. 23. This indicates complete photoresist removal at 40 seconds.

Figure 24:
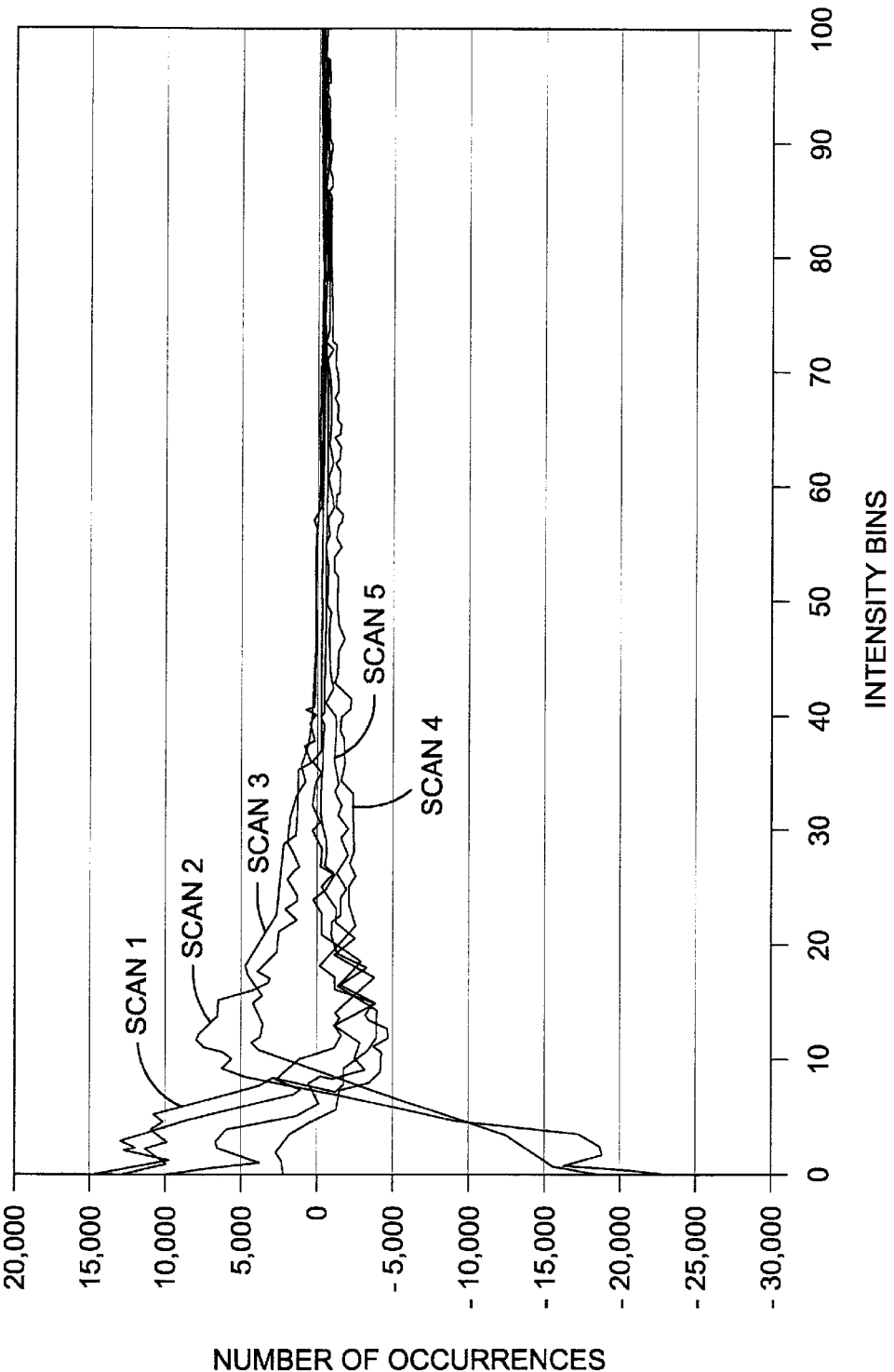
FIG. 24 is a graph of repeatability difference plots to determine system noise.

No obvious trends are evident in these curves, so these are suspected of being noise. To verify the noise level, a single stripped substrate is inspected six times in succession to determine repeatability. This information is shown in FIG. 24. Given the repeatability scans look similar to the FIG. 23 scans, thus it can be concluded that the substrates were completely stripped at 40 seconds, and that the noise level is confined to an envelope which is about 15,000 counts at the zero intensity and decaying for brighter intensity values. This envelope can be multiplied by 3 to provide a 3-sigma envelope. Anything beyond this envelope represents statistically valid data. In a production facility, sigma would be measured for each product type, and include a systematic study of sources of variation.

In any case, it can be seen that the 26 second strip time shows a peak at intensity bin 10 of 70,000 which is more than double the projected 3-sigma envelope. This is a reference measurement of the remaining photoresist. The photoresist should be detectable on a 35-second stripped substrate, since this signal would be>3 sigma. Thus, 700 A of photoresist can be detected on a substrate.

In another embodiment, a moving average (i.e., box car average) of the mean values may be used. An average of successive mean values obtained during the production process may be obtained by summing a quantity of previous mean values and then dividing by the number of successive mean values summed. Once the average mean value has been obtained, the average mean value may be used as a moving reference to compare against a new substrate mean values. If the new substrate mean value is within tolerance values about the average mean value, a new reference average mean value is calculated by replacing one of the previous mean values with a current mean value from a current substrate and calculating as above. Warning an alarm control limits would be maintained to ensure the average mean value does not "creep" up or down possibly exceeding the process tolerances.

By using an optimally processed substrate as a reference signature, it is possible to quickly conduct a series of recipe experiments and observe the results without having to remove the substrate for independent verification. The scan may be done until the signature differences are relatively close.

In addition, images of patterned substrates which contain useful information obtained according to embodiments of the invention can be used for measuring other process-related parameters on substrates. For example, photoresist remaining on patterned substrates following metal etch and strip/passivation processing can be detected.

In metal etch processes, substrates are etched and stripped in-situ. In-situ stripping and passivation is required in order to prevent corrosion of the etched aluminum structures on the processed substrates. All photoresist must be removed from substrates because the photoresist, contains chlorine, that will cause corrosion of the aluminum following venting of the substrates to the manufacturing atmosphere containing some humidity. In a typical manufacturing situation, substrates will be exposed to air from one (1) hour to one (1) day before subsequent processing, where corrosion would be halted.

In a production environment, an OIS 150 of the invention could be used as a photoresist detector to prevent any substrates having residual photoresist thereon from being vented to atmosphere, where corrosion could occur. Embodiments of the invention could be used to measure a large number of substrate condition, such as large particles, residual photoresist, oxide thickness in the corners of substrates, etc. Other detection processes could be achieved using embodiments of the invention, limited only by the extent to which there are structure changes on the substrate surface.

In one embodiment, a number of processing systems 100 having inspection devices associated therewith could be networked together and could track individual substrates' data to detect process integration issues. For example, oxide thickness could be tracked using spectral scans of the corners of substrates from oxide deposition, through oxide etch/strip to metal etch/strip. Metal stack changes in thickness and uniformity could similarly be tracked. Large particles could be tracked through various process steps so that the particle-generating hardware could be accurately and quickly identified. A networked inspection web could form the capability for process integration monitoring of substrates through the production line from start to finish of the manufacturing process.

At least one embodiment of the invention uses a two-tier particle detection method. The first tier uses various blob analysis techniques to determine approximate size and position of particles as represented by pixel occurrences. This information can also be used to determine the proximity of these pixel occurrences. The second tier uses the number of pixel occurrences above an intensity threshold to determine warning and alarm conditions. This approach allows approximate size and position of particles to be determined and individual pixel intensity thresholds to initiate an alarm.

In one embodiment, maximizing the contrast of the obstructions may be accomplished by selecting a polarized light source and linear polarization filters configured to select light that has been rotated at about 90 degrees from the polarization direction of the polarized light source. This "cross polarization" filtering method results in scattered light being the principal component entering the receiver. Signal scattering represents signals that have been rotated in a random fashion. Rotation occurs when the signal illuminates features/structures on the surface of the substrate.

Using cross polarization allows for the selective removal of specular components of the reflected light pattern from substrates having and accentuating the scattered light to increase the contrast of obstructions. This approach serves to emphasize light contribution from structures of a patterned substrate thereby increasing sensitivity to intensity variations caused by process problems, substrate layer or thickness problems and/or routing errors.

In another embodiment, detecting changes in the intensity of the reflected signal is used to accentuate the reflected light caused, in some cases, by micro-mirrors formed by a "dished" substrate surface. The dished surface directs signal away from and towards the receiver.

B. Spectral Analysis

In other embodiments, spectral data acquired from a substrate is image is used to advantage. Spectral data may be collected using a spectrometer, color CCD camera or other devices known in the art. Illustrative embodiments using color acquisition devices were described above. For example, FIG. 9 and FIGS. 12A–C shows an OIS 150 using a spectrometer.

In one embodiment, the spectral data collected from a given substrate is used to generate a spectral signature, in much the same manner a specular signature (discussed earlier) is generated. The spectral signature represents the color constituents and intensity of the substrate. As described with regard to specular signatures, this color signature may then be compared to a reference color signature to determine characteristics such as the substrate type and residual materials in processing.

Figure 25:
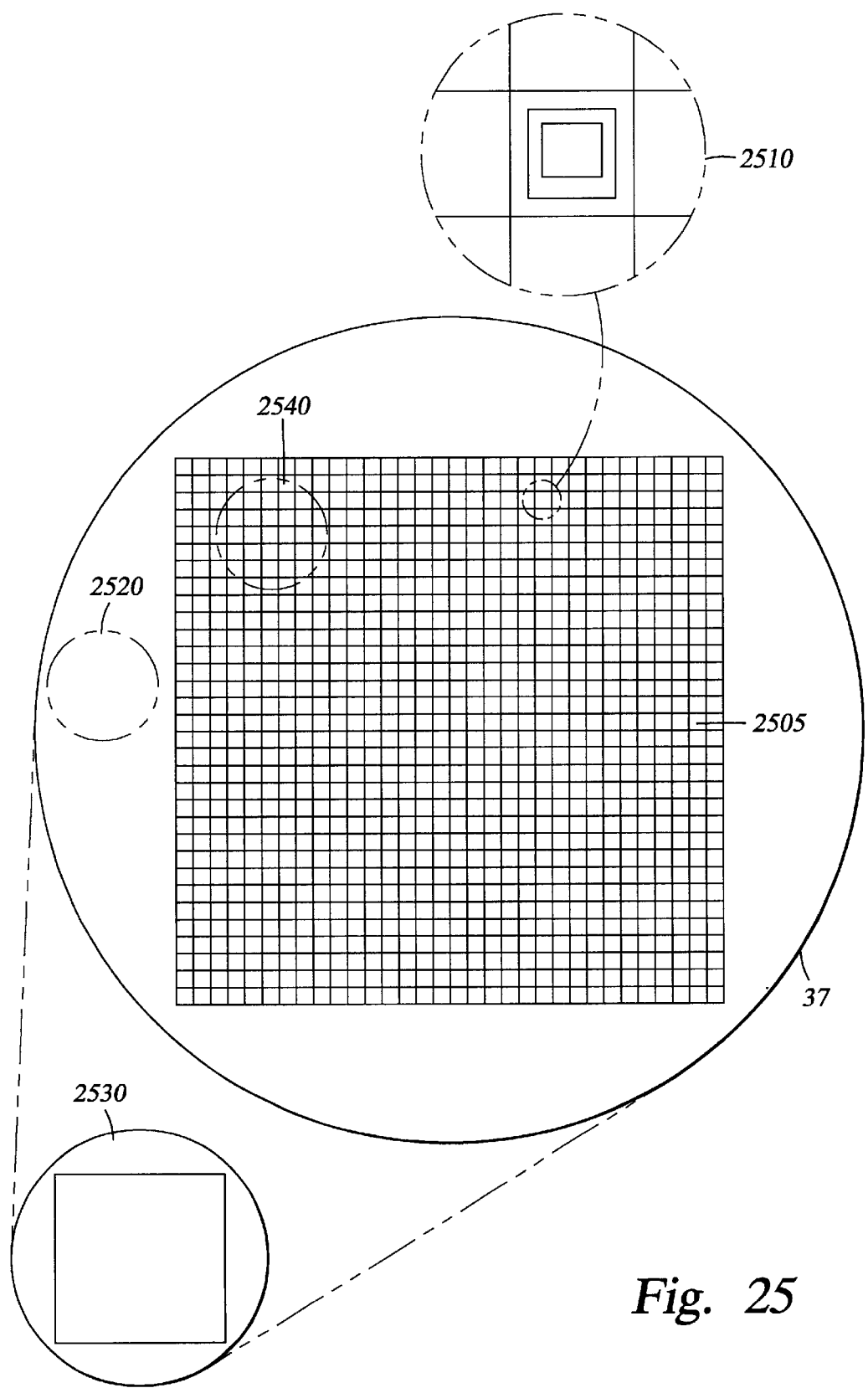
FIG. 25 is a top down substrate surface view for spectral analysis.

FIG. 25 illustrates the various regions of a substrate 37 were spectral data may be used to discern process issues. For example, substrate region 2505 is defined by a hashed area indicating various electronic devices etched and processed into the substrate during processing. Substrate region 2510 is a magnified view of a processed area of the substrate. Substrate region 2520 is an open area of the substrate 37 processed but without any etched circuitry. Substrate area 2530 is the overall view of the substrate 37 from a micro view, capturing all of the substrate in one view. Substrate region 2540 illustrates an area of substrate 37 that may be viewed by a receiving device of an OIS 150 as described above.

All of these regions provide spectral information when illuminated by a signal such as a light source. Differing color/spectral signatures may be used to determine regional and global process anomalies. For example, consider the case where the substrate region 2520 is normally a green color when viewed by a spectrometer. During the process inspection by the OIS 150 the spectrometer captures a view of the substrate region 2520 for a new substrate and discovers that the coloration has a blue component. As it is known that as substrate thickness varies, so does the color, the change from green to blue-green may indicate that there is a process issue, or perhaps, that the substrate layer thickness was incorrect.

Each area viewed 2510, 2520, 2530, and 2540, represent different process monitoring points and potential issues. For example, the coloration of the substrate region 2520 may indicate a change in the plasma density during processing. Over etching may also produce a different spectral signature.

In one embodiment, a succession of color scans of the same substrate are overlaid to provide a color contour map of the substrate. The color contour map enhances the process inspection by effectively illustrating color changes across the substrate. For example, a substrate having a uniform smooth surface normally would have little change in color variation. A substrate color contour map illustrating variations in color may relate to changes in substrate thickness and/or uniformity of the plasma process step.

In another embodiment, the amount of energy received is a function of the size of the fiber optic cable. For example, as shown in FIG. 9, a fiber optic cable 170 is used to direct the reflected light from light source 56. The fiber optic cable is made from a plurality of strands of fiber optic filaments. Increasing the number of strands increases the amount of collected signal energy that is transmitted to the spectrometer 58C.

In one embodiment, the angle of the detector or fiber optic cable is moved relative to the major axis of reflected light to enhance a particular color spectrum. Different spectrums relate to topographical and/or material differences in substrates such as substrate thickness, obstructions, type of substrate material, and the like.

C. Substrate Type Identification and Routing

In one embodiment, the invention determines the substrate type. As noted above, the pattern of substrates provides a unique specular and spectral signature. Accordingly, the invention may be used to recognize substrates based on their signature by scanning the substrate in the manner described above and transmitting the received signal to the PMC 86 for processing. As mentioned above with reference to FIG. 9 the receiver 58 receives the reflected and scattered portion of the light and determines the color of the substrate surface. The scanned pattern is then compared to stored color and/or specular signatures to determine the substrate type. Such an application provides the ability to detect a substrate that may have been misrouted through the system. For example, the OIS 150 could detect and reject a substrate with photoresist which has been mistakenly routed to a physical vapor deposition (PVD) chamber, thereby preventing potential damage to a process chamber and the substrate. In addition, recognition of the substrate pattern can be used to automatically change the process recipe according to the substrate type. Furthermore, substrate recognition allows the apparatus to automatically select the appropriate test/ monitoring criteria for warning and alarm conditions.

D. 3D Imaging

The invention also enables monitoring of obstructions in three dimensions (3D). In one embodiment, referring again to FIG. 2, the substrate is scanned in two or more directions with light source 56A and then scanned in two or more directions with light source 56B. Receiver 58 captures the reflected and/or scattered signals from sources 56A–B comprising two or more different images. As the sources 56A–B are angled at about orthogonal from each other the light illumination impinges on the substrate surface obstructions from two differing angles (i.e. perspectives). Therefore, the image from light source 56A therefore obtains information pertaining to one side of obstructions while the image from light source 56B offers information pertaining to the opposite side of the obstruction.

It is contemplated that using light source 56A and 56B scanning may be done in any plane and substrate movement in any direction. For example, a substrate may be moved in one direction to be scanned by light source 56A, and then moved in the same, or different direction, to be scanned by light source 56B. In another embodiment, a plurality of light sources may be used at differing angles to scan the substrate.

Using data summation and image processing techniques, an approximate three-dimensional representation of the surface of the substrate may be obtained. This image enables the process monitoring system to ascertain the magnitude, height, and/or depth of a particular, obstruction, or patterned feature. Thus, three-dimensional imaging enables mapping of the surface topology of the substrate for comparison to other substrate topologies and determination of the relative uniformity of the surface.

E. Optical Character Recognition

In another embodiment, the invention provides for Optical Character Recognition (OCR). OCR refers to the detection and processing of alphanumeric characters through video imaging. Substrates are often identified by characters which are typically inscribed on the substrate surface. As illustrated in FIG. 10, the transmitter unit (shown hidden) and the receiver unit 58 of the present invention provide an apparatus capable of illuminating and detecting the characters and then directing a signal to the PMC 86 for processing. The receiver unit 58 is positioned to receive reflected and/or scattered light. In operation, a substrate is scanned in the manner described above. During the scan the signal 54 will strike the characters on the substrate and be reflected/scattered according to the geometry of the characters. As described above, the reflection/scattering is unique to the particular arrangement and configuration of the characters. OCR technology generally utilizes pattern recognition algorithms adapted to recognize and read images (e.g., characters, symbols, bar codes, and the like).

F. Orientation and Center-Finding

In another embodiment, the invention is used to determine a substrate's orientation and center. Orientation and center-finding are necessary to ensure proper positioning of the substrate in a chamber for processing. For example, etching often involves the use of a mask, guard-ring or clamp to cover certain portions of the substrate surface. In order to position the mask, guard-ring or clamp on the appropriate portions of the substrate the center of the substrate must be place accurately in the process chamber. Accordingly, the curvature of the substrate edge can be used to center/orient the substrate. Further, the flat or notch (typically provided on substrates) can be used to verify the orientation.

Substrate center-finding currently employs the use of one or more sensors to determine the center of a substrate. Use of the present invention enables substrate center-finding capability, thereby minimizing the need for additional sensors. In particular, the substrate can be scanned in the FI 104 for process monitoring and particle detection. Accordingly, the information received during the scan can be processed to determine the center and/or orientation.

In one embodiment, the center and/or orientation is found while the substrate is moving. As described above, a substrate can be illuminated and scanned by the OIS 150 (i.e., the transmitter unit 56 and the receiver unit 58) during the retraction, extension, and/or rotation of the blade. Thus, in one embodiment, the diameter and, therefore, the center, of the substrate can be determined by the PMC 86. For example, as the substrate is moved into the path of the signal, the leading edge of a substrate is detected due to reflected light. Once the substrate passes through and beyond the signal, the receiver unit 58 ceases to detect a signal. The time between initial detection of a signal and ceasing detection is recorded. For a known robot speed, the recorded time may be used to calculate the diameter of the substrate. If the substrate is determined not to be centered relative to a calibrated value, an adjustment is made to the destination coordinate of the robot to correct the offset. It is understood that the particular method of calculating the substrate center is not limiting of the invention and people skilled in the art will recognize other possibilities. For example, in another embodiment, detection of the leading and lagging edges of the substrate may be associated with the encoder value of the robot at the time of detection. The encoder values can then be compared to calibrated values for substrates of the same diameter to determine any offset that must be accommodated.

In another embodiment, a substrate's orientation and center can be found while the substrate is positioned in a chamber (i.e., while the substrate is stationary), such as a cool down chamber, a degas chamber, or any other chamber of a processing system such as the one shown in FIG. 1A. Center-finding and orientation can be simultaneously done by positioning the substrate in the field of view of the receiver unit 58. FIGS. 13A–C shows one embodiment of an OIS 150 adapted for orientation and center-finding in cases where the substrate is not moving. The surface of the substrate is illuminated by the movement of the OIS components, rather than the movement of the substrate. Alternatively, with reference to FIGS. 9 and 10 the transmitter unit may be configured to illuminate a sufficient portion of the substrate without any movement of either the OIS components or the substrate (such as where the transmitter unit comprises a flash device and any respective optics). In this manner, the chamber acts both as an area for analysis of the substrate as well as performing a processing function such as cooling or degassing. As a result, analysis can proceed without affecting the throughput of the processing system.

G. Device Calibration

In addition to inspecting a substrate, the invention is also adapted for calibration. In one embodiment, the invention may be used to calibrate the detection devices. Because the illumination and detection optics of the invention may not be uniform, the operation must be normalized. In one embodiment, normalization is accomplished in the following way. When the OIS 150 (the transmitter unit and the receiver unit) is first installed, a substrate will be placed upside down on a robot blade to provide a scattering surface. The robot blade will then move the substrate under the OIS 150. During the rotation or linear movement of the blade, both peak-to-peak and root-mean-square (RMS) measurements are made across the surface of the substrate taken by the OIS 150 and transmitted to the PMC 86. A comparison is then made between the average reading of each OIS 150 measurement to determine the correction factors necessary to normalize the system. Subsequently, the substrate is removed and the solid portion of the robot blade (i.e., excluding holes and edges) is then scanned in a similar fashion. The peak-to-peak and average intensity values on the blade is then compared to the normalized correction factors to determine appropriate blade correction factors across its stroke. With the blade normalization factors in place, the blade can act as a resident calibration reference. Thus, the OIS 150 in conjunction with the PMC 86 can monitor the empty blade during normal operation to determine if the receiver and transmitter are functioning properly. If the receiver and transmitter are contaminated, or degraded, it will be detected by the foregoing background test. Also, the planarity and consistency of the blade are monitored and confirmed.

H. Blade Contamination

Additionally, contamination disposed on the surface of the blade is also detected by the test described in the foregoing embodiment. Contamination on the blade indicates that the backsides of substrates are being scratched at some point during the handling of the substrate and/or residual process byproducts have collected on the substrate. Thus, if contamination is detected on the blade, the system can be halted for inspection, thereby preventing further contamination to the processing environment.

I. Robot Calibration

In another embodiment, the OIS 150 facilitates robot calibration. The processing system robots, such as the transfer chamber robot 113, periodically require calibration in order to ensure proper orientation and alignment. Because the OIS 150 is mounted at a fixed location on a processing system, the OIS 150 can provide a point of reference for the transfer chamber robot calibration to the PMC 86. Once the blade normalization factors have been determined, as described above, the blade features can be detected to verify the robot position. Velocity and vibration can be monitored to monitor/adjust proportional, integral and differential (PID) values of the motion control system. Sufficient variance between the detected position values and the calibrated position values stored by the PMC 86 indicates misalignment of the blade. The misalignment can therefore be corrected automatically.

J. Robot Behavior

The invention also enables monitoring of robot behavior. For example, as the robot blade is rotated through the optical path 61 (shown in FIG. 6) of the receiver unit 58, the blade edge nearest to the center of rotation will enter into the optical path first. This edge will then enter the field-of-views (FOVs) of each detector element successively at a rate which is determined by the blade velocity. This allows the OIS 150 to independently monitor the behavior of a robot including characteristics such as settling time, accelerations and stability can be measured/monitored. The collected data can be used to manually or automatically set the PID parameters of the robot 113.

Various other possible applications are not discussed here in detail. For example, the invention may be used to detect the presence of a substrate on a robot blade as well as determining whether the substrate is in a blade clamp used to secure the substrate during the movement of the blade. Those skilled in the art will recognize other applications contemplated by the present invention.

Thus, the invention facilitates the integration of numerous functions currently achieved by different components in a typical processing tool. One or more OIS units 150 advantageously positioned, such as in a transfer chamber, can perform multiple process monitoring functions. Accordingly, the invention provides a multi-purpose apparatus capable of achieving a relatively higher level of system integration and reducing the system operating costs.

K. First Wafer Effect

One common condition in semiconductor processing is known as "first wafer effect." First wafer (i.e. substrate) effect is the impact of clean chamber conditions on substrate processing. Chambers must be cleaned periodically to remove residue build-up which accumulates over time on the internal the chamber surfaces. However, it was discovered that the pre-cleaning substrate processing results differed from the post-cleaning processing results. In particular, the first N number of substrates after a cleaning cycle exhibited different characteristics from subsequently processed substrates. Accordingly, a cleaned chamber is typically subjected to a seasoning process whereby the chamber is allowed to reach an equilibrium under which substrates are substantially uniformly processed. The seasoning involves operating the chamber under processing conditions (or modified processing conditions in order to accelerate the desired result) to allow the chamber surfaces to be coated with material. However, one problem with a seasoning process is determining when the chamber is sufficiently seasoned.

One embodiment of the invention allows for an end-point detection of a seasoning process. Specifically, substrates are processed in a cleaned chamber during the seasoning of the chamber. Each substrate is then inspected by one or more OIS 150. Once a processed substrate exhibits predetermined characteristics, the chamber is known to be sufficiently seasoned.

L. Throughput Monitoring

In another embodiment, throughput is monitored. Throughput can be monitored by determining when a given substrate enters the processing system and when the substrate exits the processing system (or completes a particular processing phase within the system). In addition, the time the substrate is resident in the cooldown chamber can also be observed and recorded. The data collected according to this method for multiple substrates can then be used to determine peak throughput, average throughput, frequency of arrival, variability of frequency and other related information.

M. Process Monitoring Normalization

In one embodiment, process monitoring differences are normalized. The process system 100 may contain a plurality of OIS 150 each monitoring a different area of the process. Each of the OISs 150 contributes a baseline process reading that fluctuates as substrates are processed. Overtime, the fluctuations maybe different enough between each OIS 150 to cause a false process degradation reading and alarm. To ensure minimal false alarms, a normalization substrate is sent through the process system and measured by each OIS 150. Any variation between OISs 150 are normalized to the normalization substrate.

In one embodiment, the reference wafer may be used to calibrate other processing systems 100. For example, if processing system 100 has known values based on a reference substrate, the same, or similar values, are expected at another identical processing system.

IX. Data Processing Systems

A program product readable by the PMC 86 determines which tasks are performable on a substrate. Preferably, the program product is software readable by the PMC 86 and includes code to generate at least substrate positional information, substrate reflectivity information, specular and/or scattering information, substrate defect information, substrate damage information, particle contamination information for smooth and patterned substrates, particle contamination information for the robot blade, alphanumeric character information, robot behavior information, calibration information for the robot and the detection devices and any combination thereof.

In one embodiment, the invention may be implemented as a computer program-product for use with the control PMC 86. The program(s) defining the functions of the embodiments described herein can be provided to a computer via a variety of signal-bearing media, which include but are not limited to, (i) information permanently stored on non-writable storage media (e.g. read-only memory devices within a computer such as read only CD-ROM disks readable by a CD-ROM or DVD drive; (ii) alterable information stored on a writable storage media (e.g. floppy disks within diskette drive or hard-disk drive); or (iii) information conveyed to a computer by communications medium, such as through a computer or telephone network, including wireless communication. Such signal-bearing media, when carrying computer-readable instructions that direct the functions of the present invention, represent alternative embodiments of the present invention. It may also be noted that portions of the product program may be developed and implemented independently, but when combined together are embodiments of the present invention.

Figure 26:
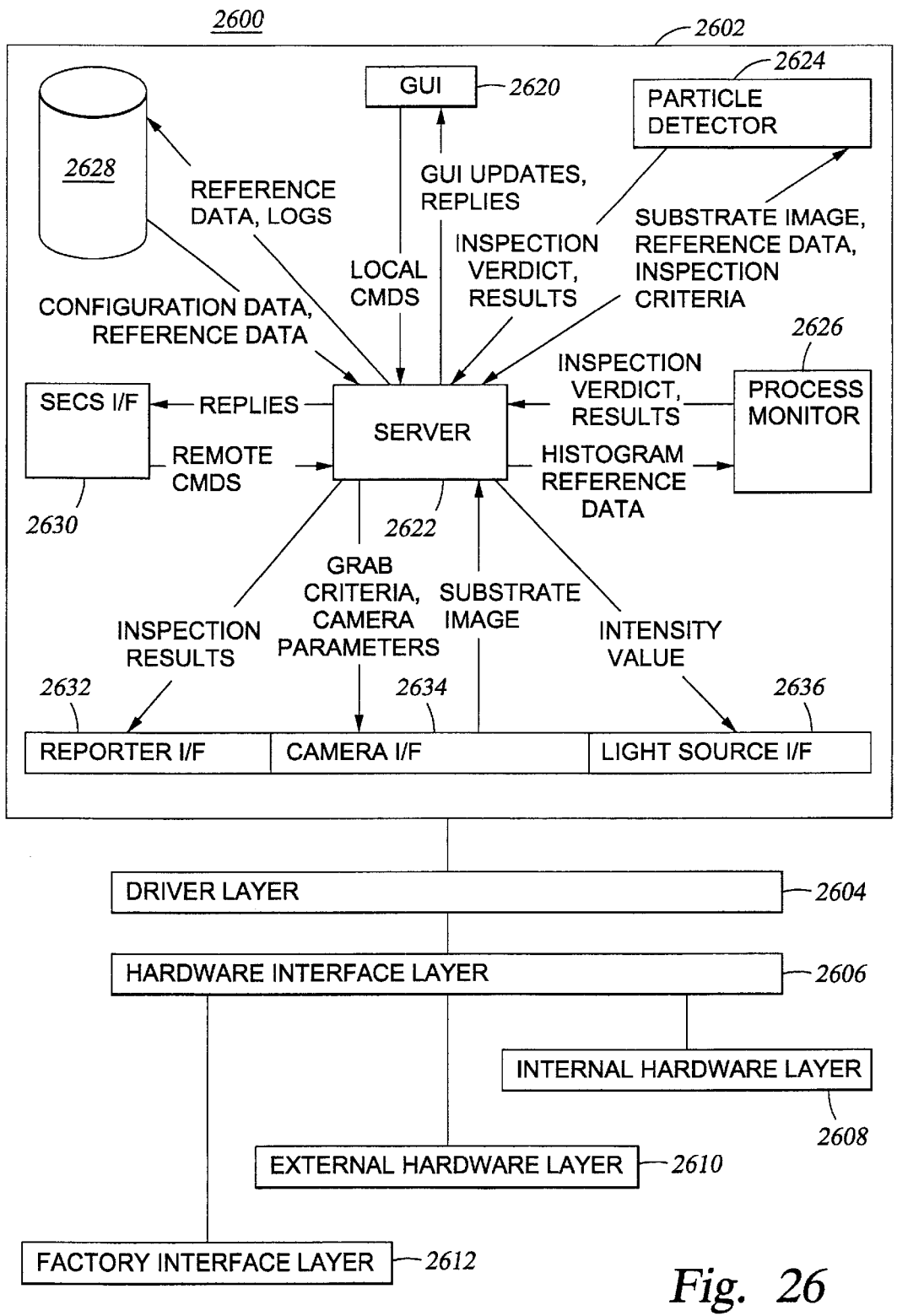
FIG. 26 is a high-level architecture of one embodiment for a system configured to perform particle detection and other process monitoring methods.

FIG. 26 is a high-level architecture of one embodiment for a system 2600 configured to perform particle detection and other process monitoring methods. Although described separately from the PMC 86, the system 2600 may be an embodiment of the PMC 86 or may be integrated with the PMC 86.

The system 2600 generally includes an application layer 2602, a driver layer 2604, a hardware interface layer 2606, an internal hardware layer 2608, an external hardware layer 2610 and a factory interface layer 2612. Each layer of the system 2600 may include any combination of hardware and software adapted to support particular functionality. In general, the application layer 2602, driver layer 2604, hardware interface layer 2606 and internal hardware layer 2608 are components of the Optical Inspection Systems (OIS) 150 described above. The external hardware layer 2610 represents any system in which an OIS 150 has been implemented. For example, the external hardware layer 2610 may be the cluster tool described above with reference to FIG. 2. The factory interface layer 2612 represents the access point between peripheral devices and the OIS 150 and the external hardware layer 2610. In one embodiment, the factory interface layer 2612 includes a host and a data collection server.

The application layer 2602 comprises a GUI (graphical user interface) 2620, a server process 2622, a particle detection process 2624, a process monitoring process 2626 and a database 2628. The GUI 2620 is a task configured to interface a user and the server process 2622. In some embodiments, the GUI 2622 comprises dialog boxes (displayable on a monitor) which convey or request information from the user. In particular, the GUI 2622 operates to generate local requests in response to user issued commands. The commands may be input to any input device such as a keyboard, keypad, light-pen, touch-screen, trackball, or speech recognition unit, audio/video player, and the like.

The local requests generated by the GUI 2620 are sent to the server process 2622 for processing. In addition to receiving requests from local clients such as the GUI 2622, the server process 2622 may also receive requests from remote clients. In FIG. 26, the remote clients are represented by the external hardware layer 2610 and the external interface layer 2612.

In response to the various client requests, the server process 2622 takes steps to generate a reply or otherwise handle the request. For example, the user-issued command from the GUI 2620 may cause the server process 2622 to call the particle detection process 2624 or the process monitoring process 2626, both of which are described in more detail below. Additionally, the server process 2622 is responsible for communicating with the other layers of the system 2600. The server process 2622 is further adapted to perform the initialization of the system 2600. Initialization may include reading a configuration file containing information for the configuration of system 2600. The configuration file may be stored in the database 2628. Thus, the server process 2622 operates as a central information managing entity for the application layer 2602.

In general, the particle detection process 2624 supports the inspection of substrate images for particles and the generation of reports. To this end, the particle detection process 2624 implements one or more particle detection algorithms. Examples of algorithms include "Blob" analysis algorithms and "pixel" analysis algorithms. The substrates inspected by the process 2624 may be smooth (unpatterned) or patterned.

The process monitoring process 2626 implements one or more process monitoring algorithms such as mean intensity analysis. In general, the process monitoring process 2626 supports the inspection of histograms and the generation of comparison plots. Embodiments of the particle detection process 2624 and the process monitoring process 2626 are described below with reference to FIG. 27–28.

The application layer 2602 communicates with the other layers of the system 2600 through one of various interfaces. Illustratively, the application layer 2602 includes a Semiconductor Equipment Communications Standard (SECS) interface 2630, a reporter interface 2632, a camera interface 2634, and a light source interface 2636.

The SECS interface 2630 reformats and communicates information between the server process 2622 and remote clients. The remote clients are represented by the external hardware layer 2610 and the external interface layer 2612.

The reporter interface 2632 is an interface task responsible for generating reports each time a substrate is inspected and then storing the reports to a local or remote disk storage facility. In one embodiment, the disk storage facility is a part of the factory interface layer 2612.

The camera interface 2634 is an interface task configured to support the operation of the receiver units (and other detecting devices, such as the substrate sensors) described above and represented by the internal hardware layer 2608. In general, the camera interface 2634 assists in the acquisition of substrate images, performing process monitoring and particle detection and setting up the receiver units. Setting up the receiver units may include downloading the receiver settings, focusing the receiver and adjusting the position (orientation) of the receiver. In addition, the camera interface 2634 initiates a request for report generation (handled by the reporter interface 2632). In operation, the camera interface 2634 receives instructions for the operation of the receiver units from the server process 2622. The instructions are then sent to the internal hardware layer 2608 via the driver layer 2604 and hardware interface layer 2606. Command responses are subsequently received by the camera interface 2634 (from the driver layer 2604) and transmitted to the server process 2622. In one embodiment, the driver layer 2604 comprises a National Instruments Image driver (NI IMAQ) driver and the hardware interface layer 2606 comprises a Frame Grabber Card with RS232 and TTL ports, each adapted to support the messages routed between the camera interface 2634 any internal hardware layer 2608.

The light source interface 2634 is an interface task configured to support the operation of the transmitter units described above and represented by the internal hardware layer 2608. In general, the functions of the light source interface 2634 include determining the current light intensity and adjusting the light intensity. In operation, information received from the server process 2622 is transmitted via the light source interface 2634 to a driver in the driver layer 2604 and then to a card in the hardware interface layer 2606. In one embodiment, the driver is an Omega ADLIB driver and the card is a DI/DO card. Responses from the internal hardware layer 2608 are routed to the light source interface 2634 in reverse order.

Although shown as a single system, the components of application layer 2602 may be distributed in a networked environment. For example, the GUI 2620 may be located on a workstation networked to a remotely located server computer on which the server process 2622, particle detector application and process monitoring application reside.

Figure 27:
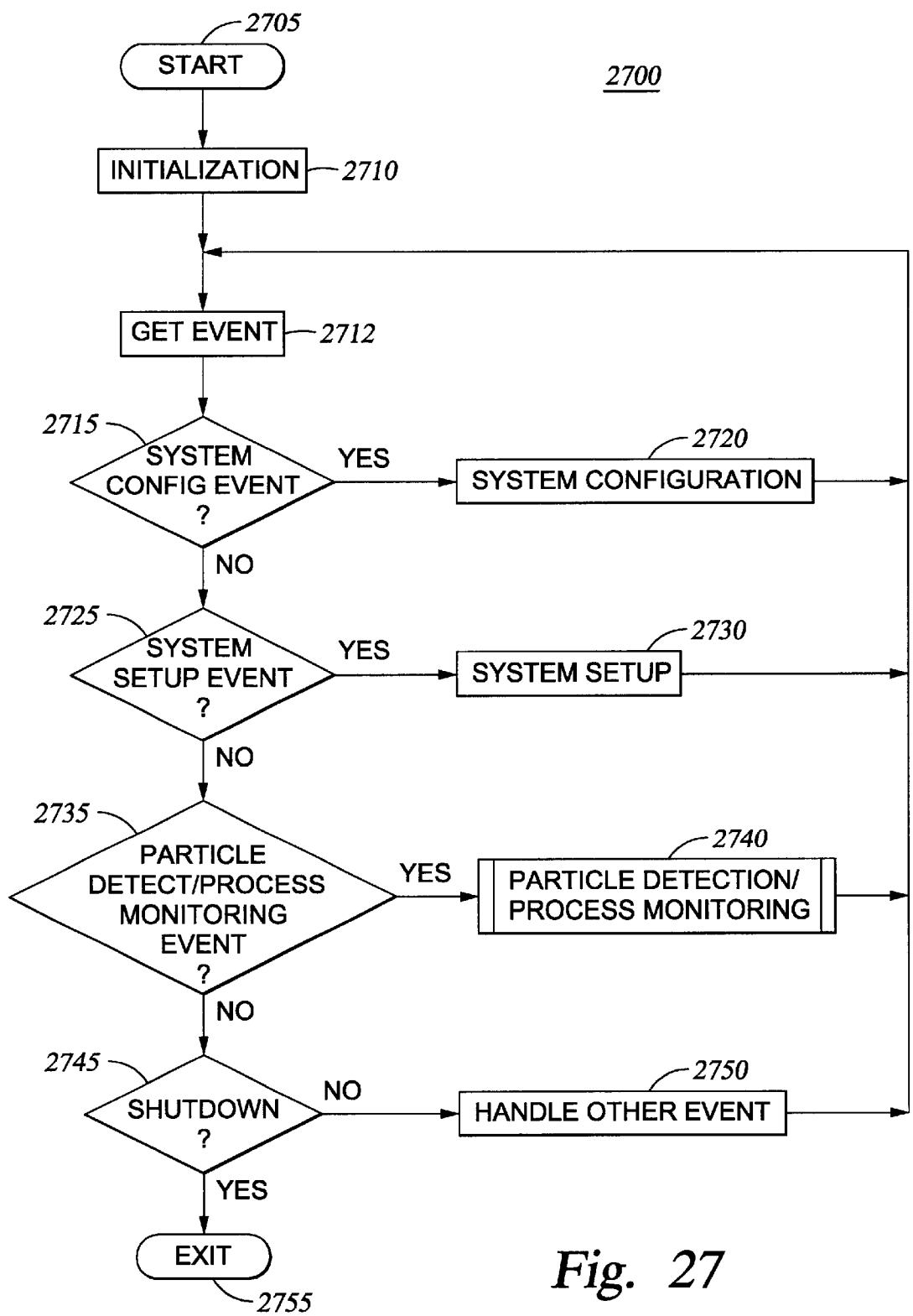
FIG. 27 is a flow diagram for a method for program control of process monitoring and particle detection using the system.

FIG. 27 is a flow diagram for a method 2700 for program control of process monitoring and particle detection using the system 2600. For brevity, the process monitoring is limited to specular analysis. However, persons skilled in the art will recognize application to other process monitoring embodiments of the invention, including spectral analysis.

Method 2700 is entered into at step 2705 when the system 2600 is activated. At step 2710, the system 2600 is initialized and is ready to receive program input events. At step 2712 method 2700 receives an event.

At step 2715, the method determines whether a system configuration has occurred. System configuration events include configuring data storage directories, establishing defect maps, setting alarms, defect count thresholds, and other program settings. If a system configuration event has not occurred, method 2700 proceeds to step 2725 described below. If a system configuration event has occurred, method 2700 proceeds to step 2720 to obtain and set the system configurations. At step 2720, the behavior of the program can be tuned, runtime counters set to track the operation of the program, and other system configurations set via system parameters contained within one or more data structures. In one embodiment, the data structures containing the system configurations may be stored within the database 2628 (shown in FIG. 26).

At step 2725, method 2700 determines whether a system set up event has occurred. If not, method 2700 proceeds to step 2735. System set-up events include receiver calibration (e.g., alignment and focus), setting receiver sampling rates, setting receiver parameters, and other system adjustments. If a system set up event has occurred, method 2700 proceeds to step 2730 to setup the system. Illustratively, step 2730 includes allowing the user to view and adjust specular images and respective statistical information of the signal pattern, thereby providing the user with meaningful feedback for adjusting the receiver 616 alignment characteristics. In addition, at step 2730, the receiver sampling rate is set. In one embodiment, step 2730 includes allowing the user to align and adjust the transmitter units independently to achieve a desired illumination of the substrate.

At step 2735, method 2700 determines whether the event is for particle detection or process monitoring. If not, method 2700 proceeds to step 2745. If the event is for particle detection, method 2700 proceeds to step 2740 to detect contamination on the substrate. One embodiment of a method for particle detection/process monitoring is described below with reference to FIG. 28.

At step 2745, the method 2700 queries whether the event is a termination event, such as when a user closes the active application. If so, the method 2700 is exited at step 2755. Otherwise, the method 2700 handles the event at step 2750 and then returns to step 2712 to get the next event.

Figure 28:
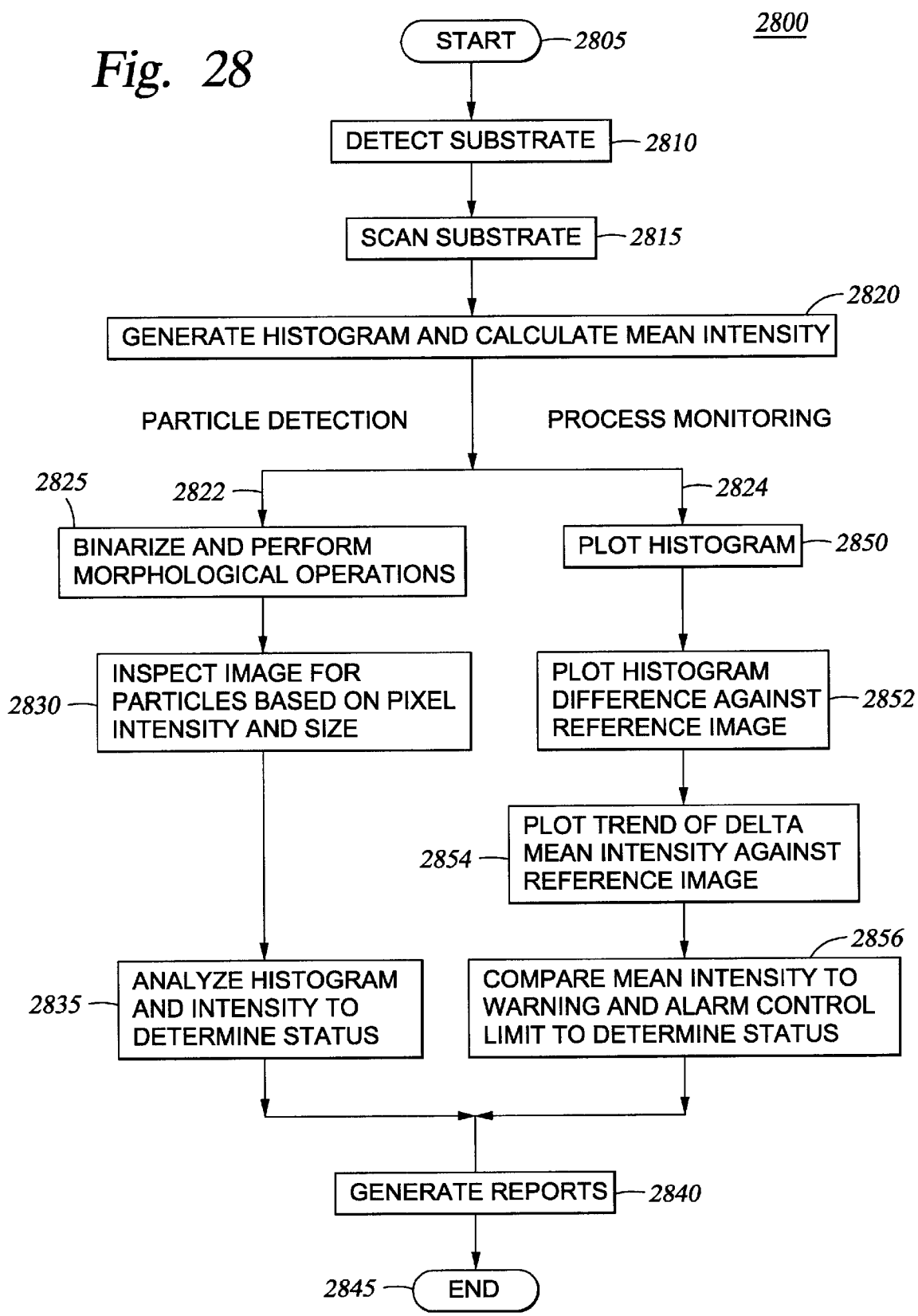
FIG. 28 is a flow diagram for process monitoring and process report generation.

FIG. 28 is a flow diagram illustrating a method 2800 for particle detection and process monitoring. Method 2800 is entered into at step 2805 from step 2740. At step 2810, the PMC 86 operates to detect the incoming substrate. One method for detecting a substrate is described above with reference to FIG. 14. At step 2815, the substrate is scanned or otherwise illuminated and the resultant signal patterns are stored. Illustrative methods of scanning/illuminating the substrate are described above.

At step 2820, method 2800 generates a histogram (also referred to herein as the current histogram) of pixel intensity based on information collected at step 2815. In addition, a mean intensity value for the substrate is calculated.

The method 2800 then proceeds along two logic paths according to the desired processing. In the case of particle detection, the method 2800 proceeds via logic path 2822 to step 2825. In the case of process monitoring, the method 2800 proceeds via logic path 2824 to step 2850.

If method 2800 proceed via path 2822, the information is binarized at step 2825. Binarization is the binary representation of a gray-scale substrate image which is represented as an array of pixel values, illustratively between 0 and 255, where 0 is black and 255 is white. A gray-scale image is binarized by selecting a threshold intensity such that each value below the threshold is black and each value above the threshold is white. The value of the threshold can be determined empirically according to a particular application.

Further, at step 2825, morphological operations are performed to manipulate and enhance the captured image by filtering noise and other extraneous signal information. Noise may be due to substrate deformations and vibration (e.g. the substrate is not perfectly flat or motionless at all times) which inadvertently causes variations (e.g., power modulation) in the scattering/reflection of the signal. Moreover, changes and contamination within the chamber such as particles floating in the chamber, optical degradation of window, heat flow within the chamber, and the like, are also time-variant and thus impart noise. Additionally, electrical noise (e.g., electronic noise, white noise, pink noise and the like) is also imparted by both the transmitter unit 56 and the receiver 58.

Methodologies to filter the signal noise are well known but depend upon the type of noise being filtered. Some methodologies include filtering the received signal using digital signal processing (DSP), electronic filters (e.g., low pass, high pass, band pass, and the like), signal sampling, averaging, and the like.

Image enhancement is accomplished using known spectral selection algorithms that can enhance image contrast and color, or by spectral filters to block unwanted spectrums. Moreover, image enhancement may be accomplished through DSP and other digital enhancement techniques well known in the art.

At step 2830, method 2800 searches the substrate image for particles based on illumination intensity and size. Blob analysis utilizes pixel intensity and proximity as a means to identify the size and location of particles in an area on the substrate. Taken together steps 2825 and 2830 constitute "blob" analysis.

The results determined by the "blob" analysis are then analyzed at step 2835. In addition, a status of the substrate is rendered at step 2835. In one embodiment, the substrate status includes a passing status, a warning status, and failing status. The user may then be notified of the status, for example, by an audible or visual signal. Upon analyzing the histogram data and particle data, method 2800 proceeds to step 2840 to generate reports including an output substrate image, a histogram data report, and defect summary to the end user. The method then exits at step 2845 and returns to method 2700.

Returning to step 2820, if selection is made to proceed via logic path 2824, the method 2800 proceeds to step 2850. At step 2850, the current histogram data generated at step 2820 is plotted. At step 2852, the histogram plot is compared to a reference histogram and the result is plotted to represent the difference between the current histogram and the reference histogram. At step 2854, method 2800 plots a trend of the mean intensity of the current histogram against the reference histogram. An example of a graph illustrating this trend is described above with reference to FIG. 20. The results of steps 2852 and 2854 are analyzed to determine a status of the substrate at step 2856. In one embodiment, the substrate status includes a passing status, a warning status, and failing status. The method 2800 then proceeds to step 2840 to generate reports which can be viewed by an end user. The reports may include an output substrate image, a histogram data report, and defect summary.

In one embodiment, an alarm is issued to the user upon the occurrence of predetermined events indicative of a defective substrate. A user is allowed to define alarm criteria based on number of occurrences that take place above a user-defined intensity threshold. Accordingly, the alarm detection thresholds can be moved closer to the noise floor established by a patterned substrate. Occurrences of intensities, which exceed the threshold are totaled and compared to a user-defined count value threshold. If the totaled occurrences exceed the count value an alarm is issued. For example, the intensity threshold level may be set so that 3,500 counts (+/-50 counts) are accumulated across the image. Upon encountering a contaminated wafer and obtaining 3,555 counts, the 5 counts above the 3,550 would cause an alarm condition to occur. As the count number increases above the count threshold the confidence in alarming increases accordingly. This represents a secondary decision quality score and can be used to establish confidence intervals.

In another embodiment, an automated mode is implemented for defining the alarm and warning thresholds. The automated mode utilized statistical values such as the mean and standard deviation of intensity across one or multiple reference substrates. The alarm thresholds are then based on some multiple of the standard deviation that could be selected by the user or predetermined based on empirical data. The standard deviation for smooth wafers would be much smaller than patterned wafers so the detection threshold would be much nearer to the mean. Such an automated approach avoids any undesirable effect resulting from subjective input from a user setting the alarm and warning thresholds.

While the foregoing is directed to the preferred embodiment of the present invention, other and further embodiments of the invention may be devised without departing from the basic scope thereof, and the scope thereof is determined by the claims that follow.

What is claimed is:

1. A method for inspecting a plurality of substrates, comprising:
   providing a plurality of fiber optic cables adapted to transmit a plurality of optical signals received from a surface of the substrates positioned at different locations;
   multiplexing, at a signal switching unit, between the plurality of optical signals transmitted by the plurality of fiber optic cables in order to allow transmission of a multiplexed portion of the optical signals;
   detecting, at a detector unit, the multiplexed portion of the optical signals received from the signal switching unit; and
   determining, at a signal processing unit, a topographical condition of the substrate according to optical information contained in the multiplexed portion of optical signals via comparison of the optical information to references optical information, wherein the optical information contained in the multiplexed portion of optical signals and the reference optical information are indicative of a plasma uniformity on a surface of the substrate.

2. The method of claim 1, wherein each of the plurality of fiber optic cables is disposed along an individual substrate transfer path.

3. The method of claim 1, wherein the detector is a spectrometer configured to receive the multiplexed portion of optical signals comprising at least one of scattered light, reflected light, and any combination thereof.

4. The method of claim 1, further comprising:
   determining whether a difference between the optical information contained in the multiplexed portion of optical signals and the reference optical information exceeds a predetermined value; and
   if the difference exceeds the predetermined value, determining that an unacceptable topological condition exists or a surface of the substrate.

5. The method of claim 4, wherein the optical information contained in the multiplexed portion of optical signals comprises substrate reflectivity information, specular information, spectral information, substrate defect information, substrate damage information, particle contamination information, alphanumeric character information, and any combination thereof.

6. The method of claim 4, wherein the optical information contained in the multiplexed portion of optical signals and the reference optical information comprise a plurality of intensity values.

7. The method of claim 6, wherein the intensity values comprise gray-scale values.

8. The method of claim 6, wherein determining the topographical condition comprises determining a first number of data readings at a given intensity of the multiplexed portion of optical signals for a range of signal intensity values.

9. The method of claim 8, wherein the reference optical information comprises a second number of data readings at the given intensity for the range of intensity values and wherein comparing comprises determining a difference in the first number of data readings from the second number of data readings.

10. A detection system for inspecting substrates in a substrate processing system, comprising:
    a plurality of fiber optical cables each configured to transmit an optical signal received from the surface of a substrate disposed in the substrate processing system;
    a multiplexor connected to the plurality of fiber optical cables; and
    a signal processing unit configured to process a multiplexed portion of optical signals received from the multiplexor and determine the presence of contamination particles on the substrate via comparison of the multiplexed portion of the optical signals to stored signals corresponding to a substantially particle free substrate surface.

11. The detection system of claim 10, further comprising a light source configured to emit the optical signal onto the surface of the substrate.

12. The detection system of claim 10, wherein the processing system is configured to generate signal signature information representing at least one of spectral and specular characteristics of the optical signals received from the surface of the substrate.

13. The detection system of claim 10, wherein the signal processing unit comprises a spectrometer configured to detect the multiplexed portion of optical signals comprising at least one of scattered light, reflected light, and any combination thereof.

14. The detection system of claim 10, wherein the signal processing unit is configured to determine the topographical condition based upon information carried by the multiplexed optical signals, the information comprising substrate reflectivity information, specular information, spectral information, substrate defect information, substrate damage information, particle contamination information, alphanumeric character information, and any combination thereof.

15. The detection system of claim 10, further comprising a light source configured to emit the optical signal onto the surface of the substrate, wherein the light source and at least one of the plurality of fiber optic cables are disposed on the substrate processing system along a transfer path of the substrate.

16. The detection system of claim 15, wherein the substrate processing system comprises a transfer chamber and wherein the light source and the at least one fiber optic cable are disposed on a lid of the transfer chamber.

17. A system comprising a substrate processing system comprising a transfer chamber, at least one processing chamber connected to the transfer chamber and an optical inspection system, the optical inspection system comprising:
(i) a plurality of light sources disposed on the substrate processing system and configured emit optical energy to illuminate a substrate disposed in the substrate processing system;
(ii) a plurality of fiber optical cables each disposed at different locations on the substrate processing system and each configured to transmit an optical signal received from the surface of a substrate disposed in the substrate processing system, wherein the optical signal comprises the optical energy provided from the plurality of light sources;
(ii) a multiplexor connected to the plurality of fiber optical cables configured to allow transmission of a portion of optical signals received from the plurality of fiber optical cables; and
(iii) a signal processing unit configured to process a multiplexed portion of optical signals received from the multiplexor and determine a topographical condition of the substrate by comparing the multiplexed portion of the optical signals to predetermined reference signals that correspond to acceptable topographical conditions.

18. The system of claim 17, wherein the multiplexed portion of optical signals received from the multiplexor comprises signal information from a single fiber optic cable of the plurality of fiber optical cables.

19. The system of claim 17, wherein the signal processing unit comprises a spectrometer.

20. The system of claim 17, wherein the multiplexed portion of optical signals comprises substrate reflectivity information, specular information, spectral information, substrate defect information, substrate damage information, particle contamination information, alphanumeric character information, and any combination thereof.

21. The system of claim 17, wherein the multiplexed portion of optical signals comprises at least one of scattered light, reflected light, and any combination thereof.

22. The system of claim 17, further comprising a transfer chamber lid having a plurality of ports formed therein and wherein each of the plurality of the fiber optical cables are disposed on separate ones of the plurality of ports.

23. The system of claim 21, wherein the substrate processing system further comprises:
a load lock chamber connected to the transfer chamber; and
a transfer robot disposed in the transfer chamber.

24. The system of claim 17, wherein an input end of each of the plurality of the fiber optical cables comprises at least one lens.

25. The system of claim 24, wherein the lens comprises a fish-eye, a diffuser, and any combination thereof.

26. The system of claim 24, wherein each of the plurality of fiber optic cables comprises a plurality of fiber optic filaments.

27. A method for inspecting substrate surfaces in a processing system, comprising:
receiving a plurality of optical signals, wherein each of the plurality of optical signals represents an individual substrate surface;
multiplexing between the plurality of optical signals; and
determining a topographical condition of the individual substrate surfaces by comparing the multiplexed optical signals to stored optical signals, wherein the optical signals are indicative of process uniformity on the substrate surfaces.

28. The method of claim 27, wherein the stored optical signals comprise a unique signature corresponding to a surface area of a substrate having acceptable topographical conditions.

29. The method of claim 28, wherein the stored optical signals comprise a unique signature corresponding to an entire substrate surface that is substantially free of contaminants.

30. The method of claim 27, wherein receiving the plurality of optical signals further comprises positioning a plurality of fiber optic cables proximate a substrate travel path.

31. A method for inspecting substrate surfaces in a processing system, comprising:
positioning a plurality of fiber optic cables proximate a semiconductor substrate travel path, wherein the plurality of fiber optic cables are positioned in portholes formed on an outer wall of a processing chamber having the substrate therein;
receiving a plurality of optical signals, wherein each of the plurality of optical signals represents an individual substrate surface;
multiplexing between the plurality of optical signals; and
determining a topographical condition of the individual substrate surfaces by comparing the multiplexed optical signals to stored optical signals that are representative of known topographical conditions.

32. The method of claim 31, wherein the processing chamber is a vacuum processing chamber.

* * * * *